(12) United States Patent
Hua

(10) Patent No.: US 7,935,726 B1
(45) Date of Patent: May 3, 2011

(54) TRICYCLIC PYRONES

(75) Inventor: Duy H. Hua, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 1141 days.

(21) Appl. No.: 10/834,482

(22) Filed: Apr. 29, 2004

Related U.S. Application Data

(63) Continuation-in-part of application No. 09/712,612, filed on Nov. 13, 2000, now Pat. No. 6,916,824.

(60) Provisional application No. 60/165,151, filed on Nov. 12, 1999.

(51) Int. Cl.
*A01N 43/16* (2006.01)
*A61K 31/35* (2006.01)
(52) U.S. Cl. .................................................. 514/455
(58) Field of Classification Search ........................ None
See application file for complete search history.

(56) References Cited

U.S. PATENT DOCUMENTS

| 5,958,970 | A | 9/1999 | Hua et al. ...................... 514/455 |
| 6,384,045 | B1 | 5/2002 | Hua et al. |
| 6,426,341 | B1 | 7/2002 | Mylari |

OTHER PUBLICATIONS

Hua et al., Tetrahedron, 2003, 59, 4795-4803.*
Aggarwal et al., "A formal synthesis of (+)-pyripyropene a using a biomimetic epoxy-olefin cyclisation: Effect of epoxy alcohol/ether on cyclisation efficiency," J. Chem. Soc., Perkin Trans I:3315-3321, 1999.
Barbuch, R. et al., "Purification of 9N-[(1'R,3'R)-trans-3'-hydroxycyclopentanyl]adenine HCl: A combination of theory and experiment," Tetrahedron 53(21):7181-7190, 1997.
Billheimer, J.T., "Cholesterol acyltransferase," Methods Enzymol. 111:286-293, 1985.
Borcherding, D. R. et al., "Synthesis of analogues of neplanocin A: Utilization of optically active dihydroxycyclopentenones derived from carbohydrates," J. Org. Chem. 52:5457-5461, 1987.
Carson, J. A. et al., "β-amyloid catabolism: Roles for neprilysin (NEP) and other metallopeptidases?" J. Neurochem. 81:1-8, 2002.
Cervera, M. et al., "4-Amino-6-methyl-2H-pyran-2-one. Preparation and reactions with aromatic aldehydes," Tetrahedron 46(23):7885-7892, 1990.
Chida, N. et al., "Pd-catalyzed coupling reaction of glycosylamines with 6-chloropurines: Synthesis of 6-(β-D-Mannopyranosylamino) 9H-purine and its β- D—gluco isomer, N-glycoside models for spicamycin and septacidin," Tetrahedron Lett. 40:2573-2576, 1999.
Corey, E.J. et al., "Oxidative hydrolysis of 1,3-dithiane derivatives to carbonyl compounds using N-halosuccinimide reagents," J. Org. Chem. 36(23):3553-3560, 1971.
De Clercq, E., "Antiviral and antimetabolic activities of neplanocins," Antimicrob. Agents Chemother. 28(1):84-89, Jul. 1985.
Ellman, G.L. et al., "A new and rapid colorimetric determination of acetylcholinesterase activity," Biochem. Pharmacol. 7:88-95, 1961.

Gundersoen, L.-L et al., "6-halopurines in palladium-catalyzed coupling with organotin and organozinc reagents," Tetrahedron 50(32):9743-9756, 1994.
Hua, D.H. et al., "A one-pot condensation of pyrones and enals. Synthesis of 1H,7H-5a,6,8,9-tetrahydro-1-oxopyrano[4,3–b][1]benzopyrans," J. Org. Chem. 62(20):6888-6896, 1997.
Hua, D.H. et al., "Syntheses and bioactivities of tricyclic pyrones," Tetrahedron 59:4795-4803, 2003.
Jin, L.-W. et al., "Novel tricyclic pyrone compounds prevent intracellular APP C99-induced cell death," Journal of Molecular Neuroscience 19:57-61, 2002.
Kim, Y.K. et al., "Pyripyropenes, novel inhibitors of acyl-CoA:Cholesterol acyltransferase produced by *Aspergillus fumigatus* II. Structure elucidation of pyripyropenes A, B, C and D," J. Antibiotics 47(2):154-162, Feb. 1994.
Leonard, N. J. et al., "The synthesis of 7-substituted adenines through the use of a blocking group at the 3-position. Site of alkylation of 7-substituted adenines," J. Am. Chem. Soc. 85:3719, 1963.

(Continued)

*Primary Examiner* — Sharmila Gollamudi Landau
*Assistant Examiner* — Kyle Purdy
(74) *Attorney, Agent, or Firm* — Greenlee Sullivan, P.C.

(57) ABSTRACT

Provided are compounds of formula IA or IB:

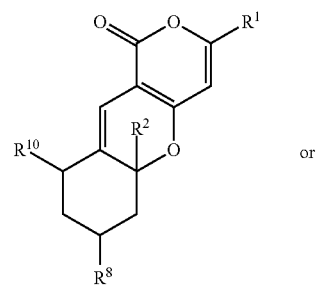

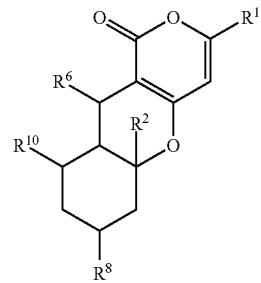

wherein R1 and R8 are independently optionally substituted hydrocarbyl groups; wherein
 (a) R1 contains a carbonyl group and a phenyl group,
 (b) R8 contains an optionally substituted adenine group, or
 (c) R8 contains an alkenyl group with from two to six carbon atoms;
$R^{10}$ is H, —OH, —OR or =O; R6 is selected from the group consisting of: H, OH, alkyl, alkenyl, alkynyl, an aromatic ring system, amino, sulfhydryl, sulfonyl, $NH_2$ and OCOR; R2 is selected from the group consisting of: H, —OH and lower alkyl; R is H or an optionally substituted hydrocarbyl group, and pharmaceutically acceptable salts or esters of the foregoing, as well as isomers thereof.

3 Claims, 4 Drawing Sheets

OTHER PUBLICATIONS

Main, A.R. et al., "The purification of cholinesterase from horse serum," Biochem. J. 143:733-744, 1974.

Marzetta, C.A. et al., "Pharmacological properties of a novel ACAT inhibitor (CP-113,818) in cholesterol-fed rats, hamsters, rabbits, and monkeys," J. Lipid Res. 35:1829-1838, 1994.

Narasimhan, N.S. et al., "Mechanism of acylation of dilithium salts of β-ketoesters: An efficient synthesis of anibine," J. Org. Chem 48:3945-3947, 1983.

Obata, R. et al., "Chemical modification and structure-activity relationships of pyripyropenes. 1. Modification at the four hydroxyl groups," J. Antibiotics 49(11):1133-1148, 1996.

Omura, S. et al., "Pyripyropenes, highly potent inhibitors of Acyl-CoA; Cholesterol acyltransferase produced by *Aspergillus fumigatus*," J. Antibiot. 46:1168-1169, 1993.

Omura, S. et al., "Arisugacin, a novel and selective inhibitor of acetylcholinesterase from *Penicillium* sp. FO-4259," J. Antiobiot. 48(7):745-746, Jul. 1995.

Perchellet, E.M., "Tricyclic pyrone analogs: A new synthetic class of bifunctional anticancer drugs that inhibit nucleoside transport, microtubule assembly, the viability of leukemic cells in vitro and the growth of solid tumors in vivo," Anti-Cancer Drugs 10:489-504, 1999.

Perchellet, J.-P. et al., "Antitumor activity of novel tricyclic pyrone analogs in murine Leukemia cells in vitro," Anticancer Research 17:2427-2434, 1997.

Puglielli, L. et al., "Acyl-coenzyme A: cholesterol acyltransferase modulates the generation of the amyloid β-peptide," Nature Cell Biol. 3:905-912, Oct. 2001.

Ralston, J.S. et al., "Acetylcholinesterase from fetal bovine serum," J. Biol. Chem. 260(7):4312-4318, Apr. 10, 1985.

Rinne, W.W. et al., "New methods of preparation of 2-methylcyclohexen-1-one," J. Am. Chem. Soc. 72:5759-5760, 1950.

Sambamurti, K. et al., "Advances in the cellular and molecular biology of the beta-amyloid protein in Alzheimer's disease," Neuro Mol. Med. 1:1-31, 2002.

Sopher, B. L. et al., "Cytotoxicity mediated by conditional expression of a carboxyl-terminal derivative of the β-amyloid precursor protein," Mol. Brain Res. 26:207-217, 1994.

Stotter, P.L. et al., "α-halocarbonyl compounds. II. A position-specific preparation of α-bromo ketones by bromination of lithium enolates. A position-specific introduction of α,β-unsaturation into unsymmetrical ketones," J. Org. Chem. 38(14):2576-2578, 1973.

Suckling, K. E. et al., "Role of acyl-CoA:cholesterol acyltransferase in cellular cholesterol metabolism," J. Lipid Res. 26:647-671, 1985.

Tall, A. R., "Plasma cholesteryol ester transfer protein," J. Lipid Res. 34:1255-1274, 1993.

Tomoda, H. et al., "Purpactins, new inhibitors of acyl-CoA:cholesterol acyltransferase produced by *Penicillium purpurogenum*," J. Antibiot. 44:136-143, Feb. 1991.

Tomoda, H., et al., "Relative and absolute stereochemistry of pyripyropene A, A potent, bioavailable inhibitor of Acyl-CoA:cholesterol acyltransferase (ACAT)," J. Am. Chem. Soc. 116:12097-12098, 1994.

Tomoda, H. et al., "Erabulenols, inhibitors of cholesteryl ester transfer protein produced by *Penicillium* sp. FO-5637. I. Production, isolation and biological properties" J. Antibiot. 51(7):618-623, Jul. 1998.

Ukai, T. et al., "Chemistry of dibenzylideneacetone-palladium(0) complexes. I. Novel tris(dibenzylideneacetone)dipalladium(solvent) complexes and their reactions with quinones," J. Organomet. Chem. 65:253-266, 1974.

Villa, P. et al., "Caspases and caspase inhibitors," Trends Biochem. Sci. 22:388-393, Oct. 1997.

Yaginuma, S. et al., "Studies on neplanocin A, new antitumor antibiotic. I. Producing organism, isolation and characterization," J. Antibiot. 34(4):359-366, Apr. 1981.

Aiello et al., (Mar. 1999), "Amelioration of Abnormal Retinal Memodynamics by a Protein Kinase C β-Selective Inhibitor (LY333531) in Patients with Diabetes: Results of a Phase I Safety and Pharmacodynamic Clinical Trial." IOVS 40:S192.

Cervera et al., (1990), "4-Amino-6-Methyl-2H-Pyran-2-One. Preparation and Reactions with Aromatic Aldehydes." Tetrahedron 46:7885-7892.

Dess, D.B. and Martin, J.C. (1983), "Readily accessible 12-[-5$^1$ Oxidant for the Conversion of Primary and Secondary Alcohols to Aldehydes and Ketones," J. Org. Chem. 48:4155-4156.

Hua et al., (1997); "(5aS,7S)-7-[sopropeny]-3-methyl-5a,6,8,9-tetrahydro-1H,7H-pyrano[4.3-b][1]benzopyran-1-one," Acta Cryst C53:1995-1997.

Hua et al., (1997), A One-Pot Condensation of Pyrones and Enals. Synthesis of 1H,7H-5a,6,8,9-Tetrahydro-1-oxopyrano[4,3-b][1]benzopyrans. J. Org. Chem. 62:6833-6396.

Urzhumtsev et at., (1997), "A 'specificity' pocket inferred from the crystal structures of the complexes of aldose reductase with the pharmaceutically important inhibitors tolrestat and sorbinil." Structure 5:601-612.

Vedejs et al., (1973), "Transition-Metal Peroxide Reaction. Synthesis of α-Hydroxycarbonyl Compounds from Enolates." J. Org. Chem. 43:183-196.

Williamson et al., (Mar. 1999), "Ocular and Cerebral Vascular Dysfunction Induced by Diabetes and by LY333531, a β-Selective Inhibitor of Protein Kinase C." IOVS 40:S369.

* cited by examiner

TRICYCLIC PYRONES

CROSS-REFERENCE TO RELATED APPLICATIONS

This application is a continuation-in-part of U.S. application Ser. No. 09/712,612, filed Nov. 13, 2000, which application claims priority to U.S. Provisional Patent application Ser. No. 60/165,151, filed Nov. 12, 1999, which applications are hereby incorporated by reference to the extent not inconsistent with the disclosure herein.

BACKGROUND OF THE INVENTION

Diabetes has many long-term complications, including nephropathy, neuropathy and retinopathy. Retinopathy is primarily a vascular disease brought on by high glucose and resulting damage to vascular tissue with subsequent damage to retinal tissues. Aldose reductase catalyzes the reduction of aldehyde sugars to their alcohol forms; D-glucose is reduced to sorbitol and galactose to galactitol. Under normal conditions the sorbitol pathway plays a minor role in glucose metabolism. However, in hyperglycemia associated with diabetic cells, which have high aldose reductase, glucose and sorbitol levels increase. Due to poor transport out of the cells, the sorbitol accumulates and causes osmotic damage to cells. The lens, retina and peripheral nerves are particularly affected. This has led to the development of drugs, which inhibit aldose reductase activity. Although aldose reductase inhibitors (ARI's) have been used to treat nephropathy and neuropathy, there is no known pharmaceutical treatment for retinopathy. The ineffectiveness of ARI's in treating retinopathy may arise from the insolubility of the drugs in water and the short lifetime (about one half hour in the human body) of these drugs. Current treatment options for retinopathy include surgery and better control of blood glucose, neither of which is completely successful in preventing blindness.

TABLE 1

Known ARI's

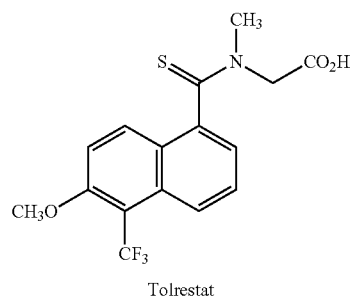

Tolrestat

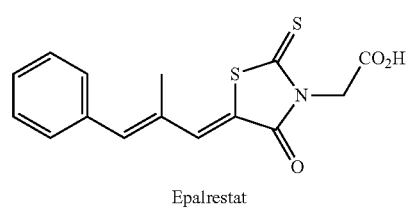

Epalrestat

TABLE 1-continued

Known ARI's

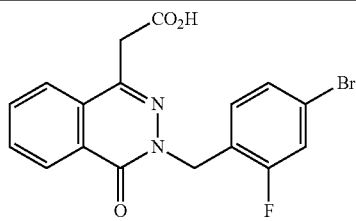

Ponalrestat (Statil)

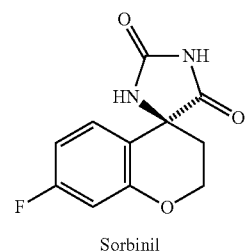

Sorbinil

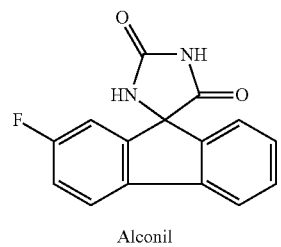

Alconil

In addition to the osmotic damage from sorbitol accumulation, the additional flux of glucose through metabolic pathways leads to increased production of diacylglycerol. This leads to cellular changes in the enzyme protein kinase C (PKC). There are various forms of PKC. The PKCβ isoform is abundant in vascular tissue where it plays a role in the maintenance of the normal growth of vascular endothelial cells and pericytes. On the other hand, this isoform is not found in vascular tissue such as lens. In lens and peripheral nerves, a major isoform is PKCγ, an isoform which decreases during diabetes and which functions to control gap junction communication.

Currently, there are five active ARI's reported: Tolrestat, Epalrestat, Ponalrestat, Sorbinil, and Alconil (Table 1). Tolrestat is currently marketed for neuropathy in humans. Currently there are no drugs available for use in dogs.

Because protein kinase C level in diabetes is abnormally high, selective inhibition of protein kinase C-β (PKC-β) has been studied in animals and found to result in normalized retinal blood flow. However, Phase I trials of the drugs used indicate that they may have undesirable side effects. (Aiello, L. et al. Amelioration of Abnormal Retinal Memodynamics by a Protein Kinase C β-Selective Inhibitor (LY33531) in Patients with Diabetes: Results of a Phase I Safety and Pharmacodynamic Clinical Trial. *IOVS.* 1999, 40, S192; Williamson, J. et al. Ocular and Cerebral Vascular Dysfunction. Induced by Diabetes and by LY33531, a β-Selective Inhibitor of Protein Kinase C. *IOVS.* 1999, 40, S369).

There is a need for drugs that are cell permeable, water soluble and more effective than currently available treatments for the complications of diabetes.

The pathogenetic events leading to Alzheimer's disease (AD) may reside in the production and deposition of amyloid-β (Aβ) peptides (Sambamurti, K.; Greig, N. H.; Debomoy, K. Neuro Mol. Med. 2002, 1, 1-31; Carson, J. A.; Turner, A. J. J. Neurochem. 2002, 81, 1-8). Aβ peptides are 39-42-amino acid hydrophobic polypeptides derived from a transmembrane glycoprotein, amyloid β precursor protein (APP). Pyripyropene A is a potent ACAT (acyl-coenzyme A: cholesterol O-acyltransferase) inhibitor (Omura, S.; Tomoda, H.; Kim, Y. K.; Nishida, H. J. Antibiot. 1993, 46, 1168-1169). It has been reported that ACAT has a modulating effect on the generation of Aβ peptides (Puglielli, L.; Konopka, G.; Pack-Chung, E.; Ingano, L. A. M.; Berezovska, O.; Hyman, B. T.; Chang, T. Y.; Tanzi, R. E.; Kovacs, D. M. Nature Cell Biol. 2001, 3, 905-912). Arisugacin has been reported to be an acetylcholinesterase inhibitor (Omura, S.; Kuno, F.; Otoguro, K.; Sunazuka, T.; Shiomi, K.; Masuma, R.; Iwai, Y. J. Antiobiot. 1995, 48, 745-746).

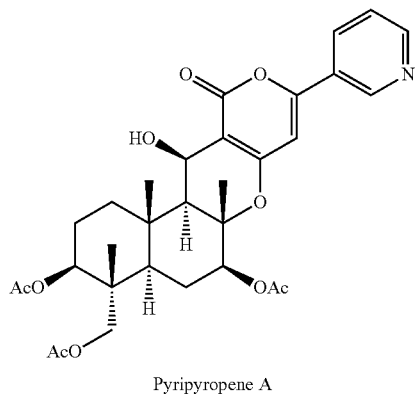

Pyripyropene A

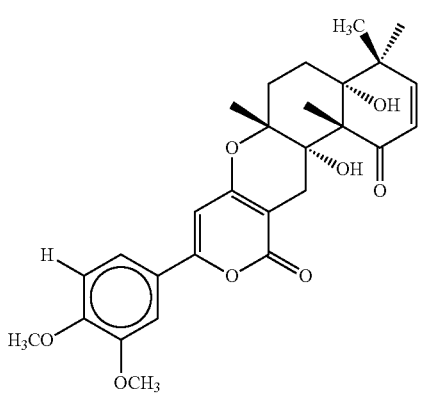

Arisugacin

There is a need for improved drugs for prevention and treatment of Alzheimer's disease (AD).

SUMMARY OF THE INVENTION

This invention provides tricyclic compounds having hydrocarbyl substituents which are useful in treating the complications of diabetes.

Preferably, the invention provides tricyclic compounds of the formula:

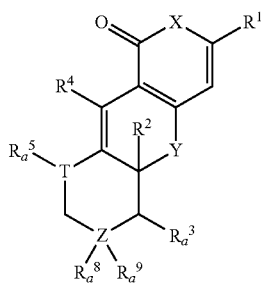

or

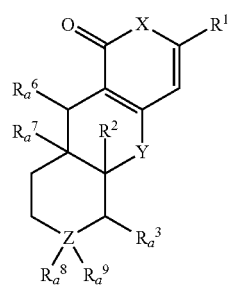

wherein:
T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

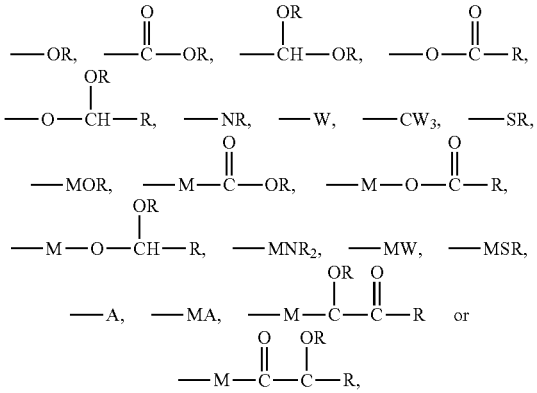

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;
$R^2$, $R^8$ and $R^9$ are independently R as defined above; and
$R^6$ is independently R, $NH_2$, OH, or OCOR where R is as set forth above;
$R^7$ is independently OH or H; or
$R^6$ and $R^7$ taken together are O;
and pharmaceutically acceptable salts or esters of the foregoing, as well as optical isomers thereof.

Also provided are compounds of formula:

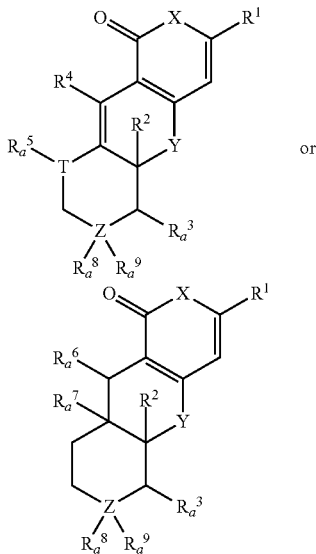

or
where
T is independently CR, NR, C, N, S or O;
X is independently O, NR, N or S;
Y is independently O, NR, N or S;
Z is independently C, N, S or O;
a is 0 or 1,
$R^1, R^3, R^4, R^5, R^8,$ and $R^9$ are independently selected from the group consisting of: —H, —OH, =O, —OR and optionally substituted hydrocarbyl groups;
wherein either:
  (a) R1 contains a carbonyl group and a phenyl group,
  (b) R8 contains an optionally substituted adenine group or
  (c) R8 contains an alkenyl group with from two to six carbon atoms;
$R^6$ is selected from the group consisting of: H, OH, alkyl, alkenyl or alkynyl, an aromatic ring system, amino, sulfhydryl, sulfonyl, $NH_2$ and OCOR;
R7 is either —H or —OH;
$R^2$ is selected from the group consisting of: H, —OH and lower alkyl; wherein R is H or an optionally substituted hydrocarbyl group, and pharmaceutically acceptable salts or esters of the foregoing, as well as optical isomers thereof.

In a preferred class of compounds of the invention, X and Y are O and T and Z are C. One class of compounds of the invention are compounds of formula IA or IB:

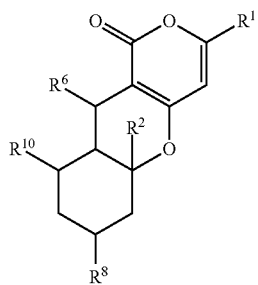

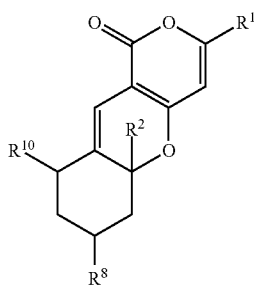

wherein R1 and R8 are independently optionally substituted hydrocarbyl groups; wherein
  (a) R1 contains a carbonyl group and a phenyl group;
  (b) R8 contains an optionally substituted adenine group; or
  (c) R8 contains an alkenyl group with from two to six carbon atoms;
$R^6$ is selected from the group consisting of: H, OH, alkyl, alkenyl, alkynyl, an aromatic ring system, amino, sulfhydryl, sulfonyl, $NH_2$ and OCOR; R10 is selected from the group consisting of: —H, =O, —OH, and —OR, wherein R is H or an optionally substituted hydrocarbyl group; $R^2$ is selected from the group consisting of: H, —OH and lower alkyl; and pharmaceutically acceptable salts or esters of the foregoing, as well as isomers thereof.

In one class of compounds of the invention, R6 is selected from the group consisting of: H, OH, and =O. In one class of compounds of the invention, R10 is selected from the group consisting of: H, =O and —OH. In one class of compounds of the invention, R2 is H.

In classes of compounds of the invention, more than one of items (a), (b), and (c) above may be present. For example, in one class of compounds of the invention, R8 contains an alkenyl group with from two to six carbon atoms and R1 contains a carbonyl group and a phenyl group.

In one class of compounds of the invention, $R^8$ contains a halogen substituted adenine group. In one class of compounds of the invention, $R^8$ contains an iodine substituted adenine group. In one class of compounds of the invention, $R^8$ contains a $^{125}I$ substituted adenine group.

Another class of compounds of the invention are compounds of formula IA or IB above, wherein $R^1$ is a lower alkyl group, $R^{10}$ is H or =O, $R^8$ is an alkenyl group with from two to six carbons, and $R^8$ can optionally contain one or more heteroatoms, $R^6$ is H or OH; R2 is selected from the group consisting of: H, —OH and lower alkyl; and pharmaceutically acceptable salts or esters of the foregoing, as well as isomers thereof. One class of compounds are of formula IB above, wherein R6 is OH or H.

One class of compounds of the invention are those of formula IA or IB wherein R8 is an optionally substituted alkyl or alkenyl group and R1 contains a carbonyl group and a phenyl group. One subclass of these compounds are those wherein R8 is an optionally substituted lower alkyl or alkenyl group. One subclass of these compounds are those wherein R1 contains a carboxyl group and a phenyl group. One subclass of these compounds are those wherein R1 contains an amide group and a phenyl group. One subclass of these compounds are those wherein R1 contains an aspartate substituent.

Another class of compounds of the invention are those of formula IA or IB wherein R8 contains an optionally substituted adenine group and R1 is an optionally substituted alkyl or alkenyl group. One subclass of these compounds are those wherein R1 is an optionally substituted lower alkyl or alkenyl group. One subclass of these compounds are those wherein R8 contains a halogen-substituted adenine group.

Another class of compounds of the invention are those of formula IA or IB wherein R1 is

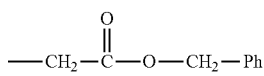

or

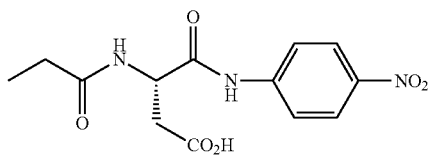

and R8 is

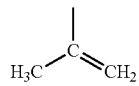

or

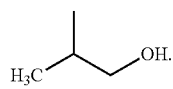

A specific compound of the invention is a compound of formula IA, wherein R2 is H; R10 is H; R1 is

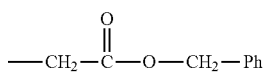

and R8 is

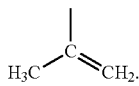

A specific compound of the invention is a compound of formula IA, wherein R2 is H; R10 is H; R1 is

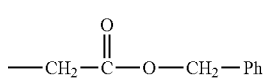

and R8 is

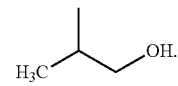

A specific compound of the invention is a compound of formula IA, wherein R2 is H; R10 is H; R1 is

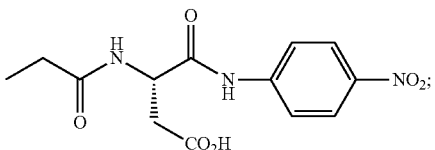

and R8 is

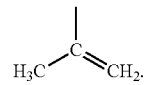

A specific compound of the invention is a compound of formula IB, wherein R1 is

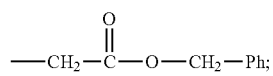

R8 is

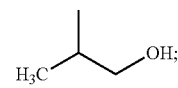

R6 is —OH; R10 is H; and R2 is H.

A class of compounds of the invention are those of formula IA or IB, wherein R1 is a lower alkyl group and R8 is

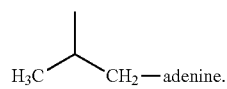

A specific compound of the invention is a compound of formula IA, wherein $R^1$ is —$CH_3$; R10 is H; R2 is H; R8 is

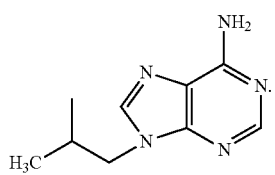

A specific compound of the invention is a compound of formula IA, wherein $R^1$ is —$CH_3$; R10 is H; R2 is H; R8 is

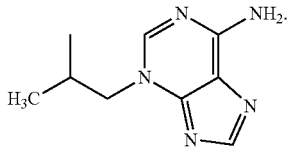

A specific compound of the invention is a compound of formula IA, wherein $R^1$ is —$CH_3$; R10 is H; R2 is H; R8 is

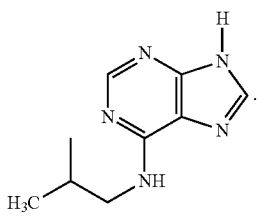

A class of compounds of the invention are those of formula IA or IB wherein $R^1$ is $CH_3$, $R^2$ is H, $R^{10}$ is H, OH or =O, and $R^8$ is selected from the group consisting of:

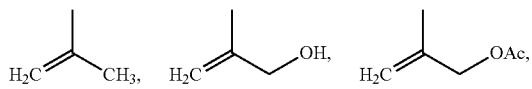

and

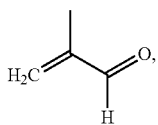

A class of compounds of the invention are those of formula IA or IB wherein $R^1$ is $CH_3$, $R^{10}$ is =O, $R^2$ is H, and $R^8$ is selected from the group consisting of:

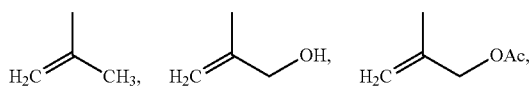

and

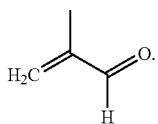

A class of compounds of the invention are those of formula IA or IB, wherein $R^1$ is a lower alkyl group and $R^8$ is

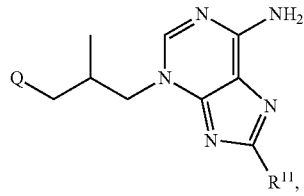

wherein $R^{11}$ is H or I or $^{125}I$ and wherein Q is H, OH, OAc or $CO_2H$ and the other variables are as defined for formulas IA or IB above. A subclass of these compounds are those wherein R2 is H. A subclass of these compounds are those wherein R10 is H, OH, =O or OR, where R is as defined for formulas IA or IB above. A subclass of these compounds are those wherein $R^1$ is $CH_3$.

A class of compounds of the invention are those of formula IA above, wherein $R^1$ is $CH_3$, $R^2$ is H, $R^{10}$ is O-t-$BuMe_2Si$, and R8 is

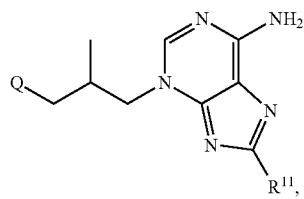

wherein Q is OAc and $R^{11}$ is H or I or $^{125}I$.

A specific compound of the invention is a compound of formula IA, wherein R2 is H; R1 is —$CH_3$; and $R^8$ is

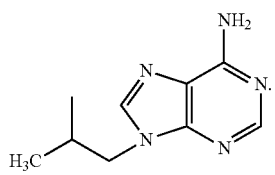

A specific class of compounds of the invention are those compounds of formula IA, wherein R2 is H; $R^1$ is —$CH_3$; $R^8$ is

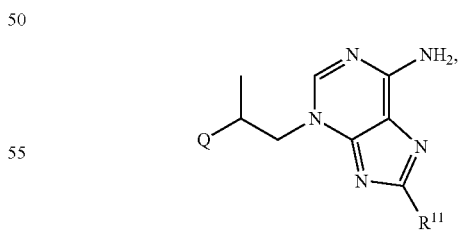

wherein $R^{11}$ is H or a halogen and wherein Q is H, OH, OAc, $CO_2H$, OR, a lower alkyl, $CH_2OH$, $CH_3$, $CH_2OAc$, $CH_2CO_2H$, $CH_2OR$, wherein R is an optionally substituted hydrocarbyl, preferably a lower alkyl or alkenyl. In a particular class of compounds, $R^{11}$ is I. In a particular class of compounds, $R^{11}$ is $^{125}I$. All stereochemical options of including $^{125}I$-1R and $^{125}I$-1S are independently included in the disclosure.

A specific compound of the invention is a compound of formula IA, wherein R2 is H; R1 is —CH$_3$; R$^8$ is

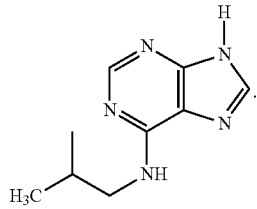

In the substituents shown (such as R1, R2, etc.), a line indicates where the substituent is attached to the compound unless otherwise noted. For example, in the substituent R$^8$ directly above, the line attached to the CH group shows where the substituent is attached to the rest of the compound.

Some specific compounds of the invention are listed in Scheme 11:

Scheme 11

101

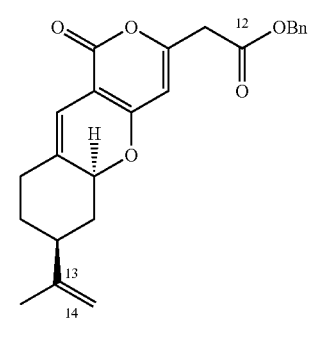

102

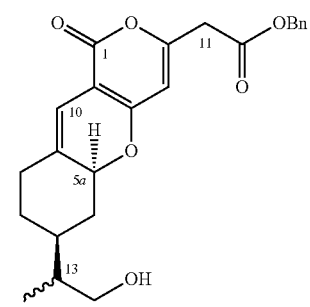

103

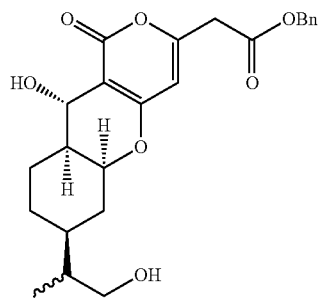

104

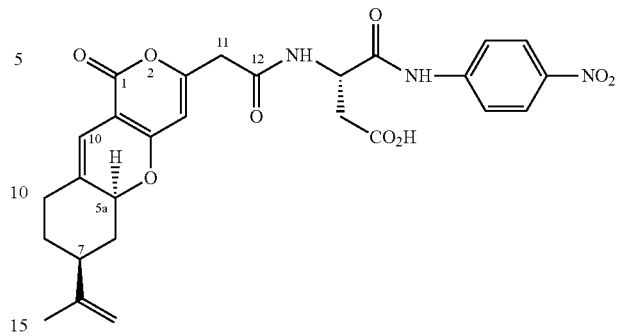

105

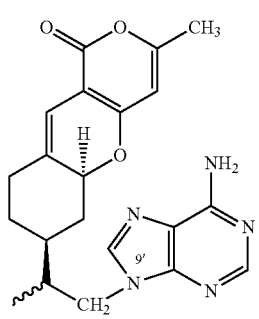

106

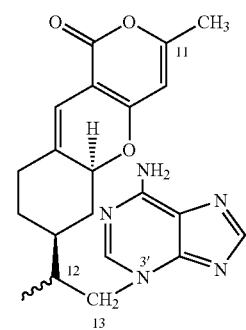

107

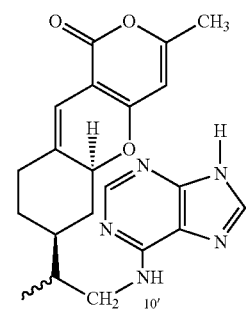

Bn = CH$_2$Ph

Scheme 11A shows additional specific compounds of the invention.

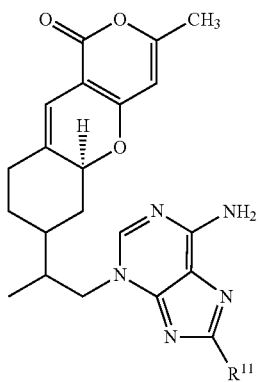

202: $R^{11} = H$
$^{125}$I-1R and -1S $R^{11} = {}^{125}I$

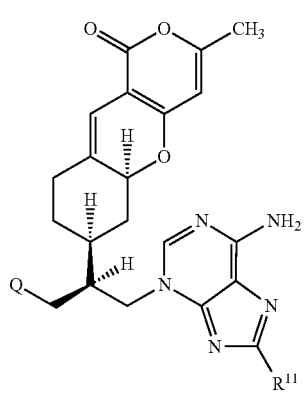

209a: Q = OH, $R^{11} = H$
209b: Q = OH, $R^{11} = {}^{125}I$
210a: Q = OAc, $R^{11} = H$
210b: Q = OAc, $R^{11} = {}^{125}I$
211a: Q = $CO_2H$, $R^{11} = H$
211b: Q = $CO_2H$, $R^{11} = {}^{125}I$

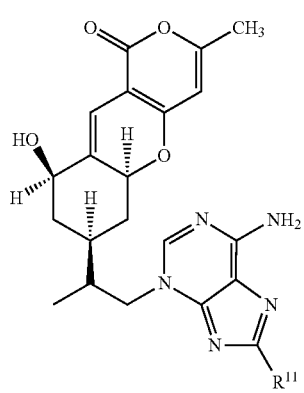

212a: $R^{11} = H$
212b: $R^{11} = {}^{125}I$

-continued

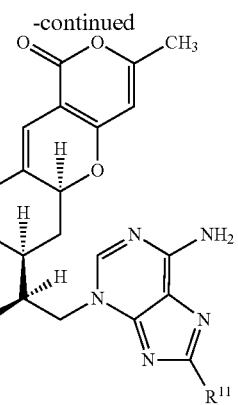

213a: Q = OH, $R^{11} = H$
213b: Q = OH, $R^{11} = {}^{125}I$
214a: Q = OAc, $R^{11} = H$
214b: Q = OAc, $R^{11} = {}^{125}I$
215a: Q = $CO_2H$, $R^{11} = H$
215b: Q = $CO_2H$, $R^{11} = {}^{125}I$

In the schemes and structures provided herein, a "wavy" bond indicates all stereochemistry is possible. Except when specifically mentioned, all isomeric alternatives and stereochemical alternatives are independently included in the disclosure herein for all compounds, even if not specifically shown or described.

Also provided are methods of making compounds of formula

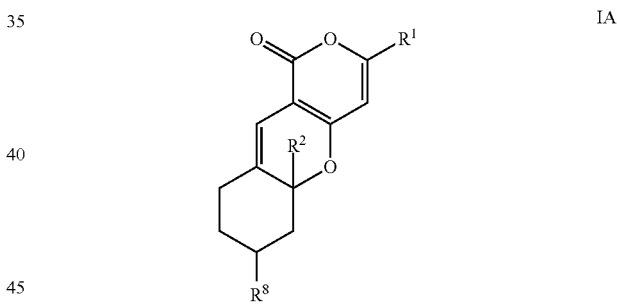

IA wherein R1 and R8 are independently optionally substituted hydrocarbyl groups; wherein R8 contains an adenine group; $R^2$ is selected from the group consisting of: H, —OH and lower alkyl; and pharmaceutically acceptable salts or esters of the foregoing, as well as isomers thereof, comprising: contacting a compound of formula:

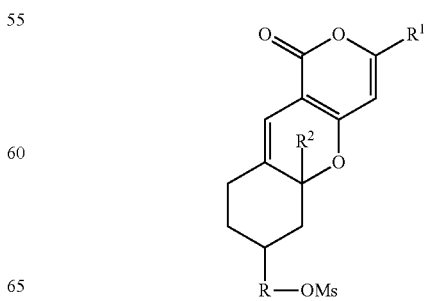

with adenine under reaction conditions, wherein R is an optionally substituted alkyl or alkenyl group having from 1 to 6 carbon atoms and OMs is a mesylate group.

Alternatively, provided are methods of making compounds of formula:

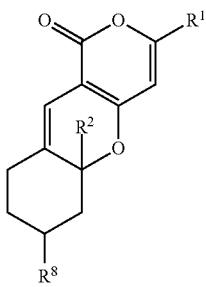

IA wherein R1 and R8 are independently optionally substituted hydrocarbyl groups; wherein R8 contains an adenine group; $R^2$ is selected from the group consisting of: H, —OH and lower alkyl; and pharmaceutically acceptable salts or esters of the foregoing, as well as isomers thereof, comprising: reacting a compound of formula:

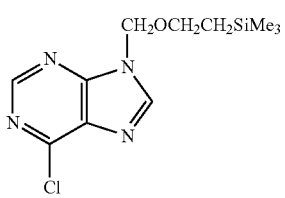

with a compound of formula

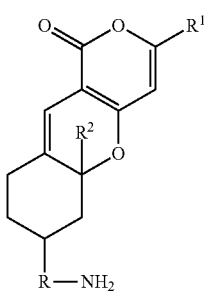

under reaction conditions, wherein R is an optionally substituted alkyl or alkenyl group having from 1 to 6 carbon atoms.

Provided are methods of inhibiting ACAT comprising: administering to a patient an effective amount of one or more compounds of formula IA or IB:

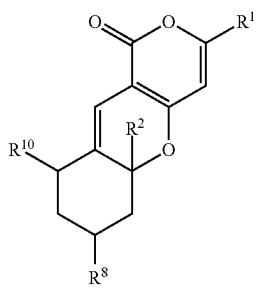

IA or

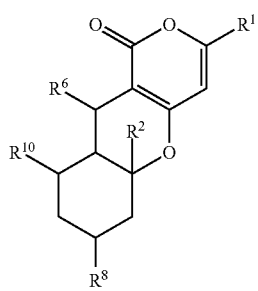

IB wherein R1 and R8 are independently optionally substituted hydrocarbyl groups; wherein (a) R1 contains a carbonyl group and a phenyl group,
(b) R8 contains an optionally substituted adenine group, or
(c) R8 contains an alkenyl group with from two to six carbon atoms;

$R^{10}$ is H, —OH, —OR or =O;

$R^6$ is selected from the group consisting of: H, OH, alkyl, alkenyl, alkynyl, an aromatic ring system, amino, sulfhydryl, sulfonyl, $NH_2$ and OCOR;

$R^2$ is selected from the group consisting of: H, —OH and lower alkyl; R is H or an optionally substituted hydrocarbyl group, and pharmaceutically acceptable salts or esters of the foregoing, as well as isomers thereof.

Also provided are methods of inhibiting CETP comprising administering to a patient an effective amount of one or more compounds of the formula IA or IB:

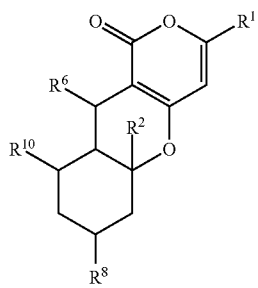

IB or

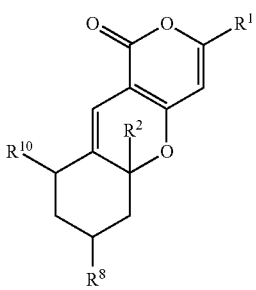

IA wherein R1 and R8 are independently optionally substituted hydrocarbyl groups; wherein
(a) R1 contains a carbonyl group and a phenyl group,
(b) R8 contains an optionally substituted adenine group, or
(c) R8 contains an alkenyl group with from two to six carbon atoms;

$R^{10}$ is H, —OH, —OR or =O;
$R^6$ is selected from the group consisting of: H, OH, alkyl, alkenyl, alkynyl, an aromatic ring system, amino, sulfhydryl, sulfonyl, $NH_2$ and OCOR;
$R^2$ is selected from the group consisting of: H, —OH and lower alkyl; R is H or an optionally substituted hydrocarbyl group, and pharmaceutically acceptable salts or esters of the foregoing, as well as isomers thereof.

Also provided are methods of protecting cells that at least partially express APP fusion protein from death comprising administering to a patient an effective amount of one or more compounds of formula IA or IB:

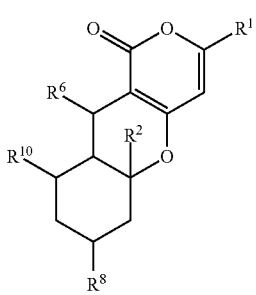

IA or

IB wherein R1 and R8 are independently optionally substituted hydrocarbyl groups; wherein
(a) R1 contains a carbonyl group and a phenyl group,
(b) R8 contains an optionally substituted adenine group, or
(c) R8 contains an alkenyl group with from two to six carbon atoms;

$R^{10}$ is H, —OH, —OR or =O;
$R^6$ is selected from the group consisting of: H, OH, alkyl, alkenyl, alkynyl, an aromatic ring system, amino, sulfhydryl, sulfonyl, $NH_2$ and OCOR;
$R^2$ is selected from the group consisting of: H, —OH and lower alkyl; R is H or an optionally substituted hydrocarbyl group, and pharmaceutically acceptable salts or esters of the foregoing, as well as isomers thereof.

Preferably the patient is a human or other mammal. Preferably the compound is selected from 101-107 or the compounds shown in Scheme 11A. Each separate compound listed herein is considered a separate class of compounds. Each separate member of each Markush group or other variable or grouping given herein is considered to form a separate class of compounds.

Provided are methods of treating a symptom or condition that results from the activity of aldose reductase comprising administering to a patient an effective amount of one or more compounds of the formula:

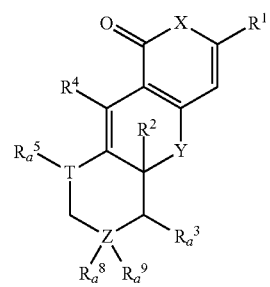

or

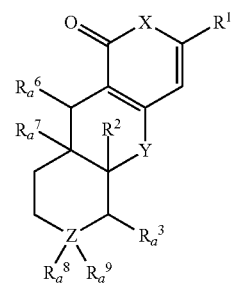

wherein:
T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

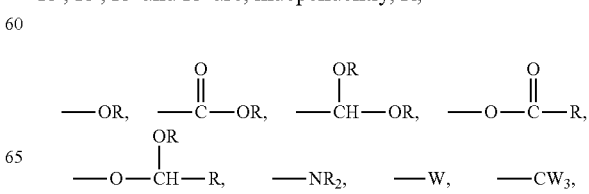

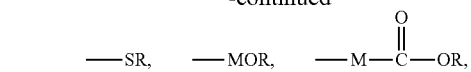

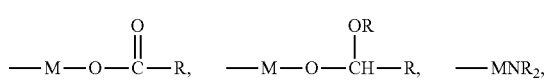

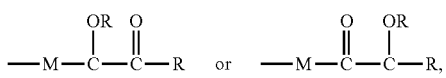

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;

$R^2$, $R^8$ and $R^9$ are independently R as defined above; and $R^6$ is independently R, $NH_2$, OH, or OCOR where R is as set forth above;

$R^7$ is independently OH or H; or $R^6$ and $R^7$ taken together are O;

and pharmaceutically acceptable salts or esters of the foregoing, as well as optical isomers thereof. Preferably, the patient is a dog or human and the compound is compound 1. Also provided are methods of inhibiting aldose reductase activity in cells, comprising contacting the cells with an effective amount of a compound of the invention. Also provided is a method for treating retinopathy comprising administering to a patient an effective amount of a compound of the invention. Also provided is a method for decreasing the loss of PKC in diabetic patients or inhibiting polyol accumulation in diabetic patients comprising administering to a patient an effective amount of a compound of the invention. Pharmaceutical compositions comprising a compound of the invention wherein the composition is useful to treat a disorder associated with the activity of aldose reductase are provided. A method of preparing a pharmaceutical composition comprising bringing a compound of formula

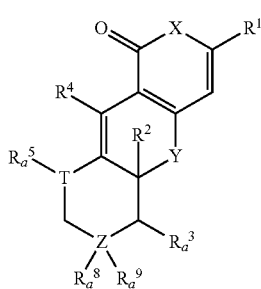

or

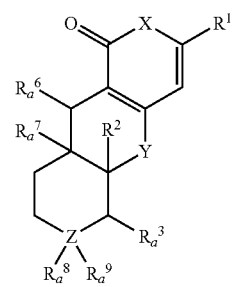

wherein:
T is independently CR, NR, N, S or O;
X is independently O, NR, N or S;
Y is independently O, NR, N or S;
Z is independently C, N, S or O;
a is 0 or 1,
$R^1$, $R^3$, $R^4$ and $R^5$ are, independently, R,

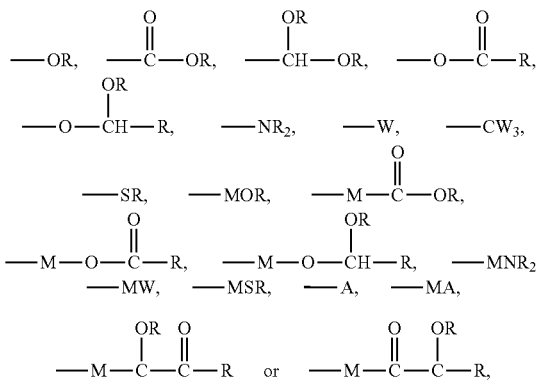

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;

$R^2$, $R^8$ and $R^9$ are independently R as defined above; and $R^6$ is independently R, $NH_2$, OH, or OCOR where R is as set forth above;

$R^7$ is independently OH or H; or $R^6$ and $R^7$ taken together are O;

and pharmaceutically acceptable salts or esters of the foregoing, as well as optical isomers thereof into association with a pharmaceutically acceptable carrier are provided. Compounds not disclosed in U.S. Pat. No. 5,958,970 and U.S. Pat. No. 6,384,045 are also provided, including

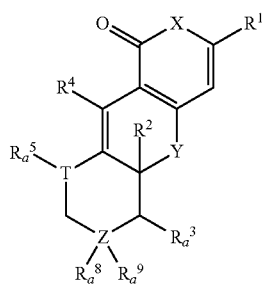

or

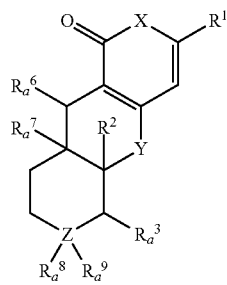

wherein:

T is independently CR, NR, N, S or O;

X is independently O, NR, N or S;

Y is independently O, NR, N or S;

Z is independently C, N, S or O;

a is 0 or 1, $R^1$, $R^3$, $R^4$ and $R^5$ are, independently, R,

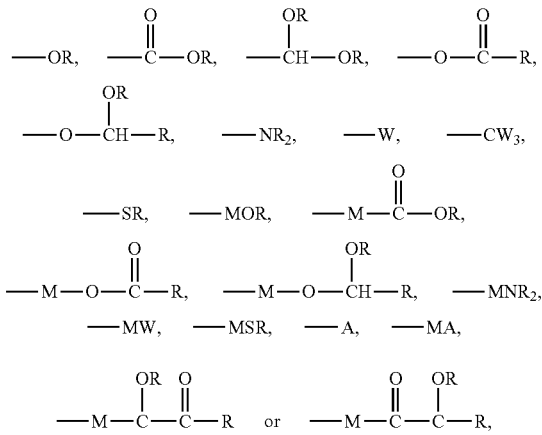

wherein R is independently H, OH, alkyl, alkenyl or alkynyl, an aromatic ring system, amino, sulfhydryl, or sulfonyl, M is a divalent alkyl, alkenyl or alkynyl, aromatic ring system, or sulfonyl, W is Cl, F, Br or OCl, and A is an aromatic ring system;

$R^2$, $R^8$ and $R^9$ are independently R as defined above; and $R^6$ is independently R, $NH_2$, OH, or OCOR where R is as set forth above;

$R^7$ is independently OH or H; or $R^6$ and $R^7$ taken together are O;

provided that either:

T is independently CR, provided that R is not H, or NR;

X is independently NR or N, provided that R is not H;

Y is independently NR, provided that R is not H; or $R^1$, $R^3$, $R^4$ and $R^5$ are, independently, —CH(OR)—OR; —O—CH(OR)—R; -M-O—CH(OR)—R; -M-C(OR)=C(=O)—R; or -M-C(=O)—C(OR)OR.

TABLE 2

Representative compounds

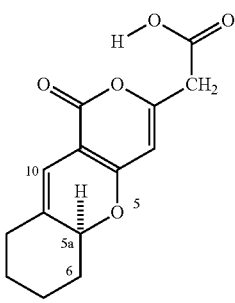

1: $IC_{50}$ = 2 nM

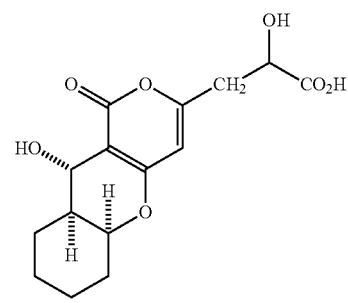

2: $IC_{50}$ = 20 nM

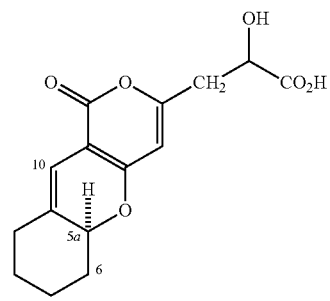

3: $IC_{50}$ = 100 nM

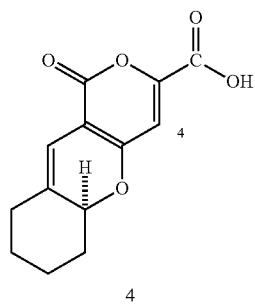

4

TABLE 2-continued
Representative compounds
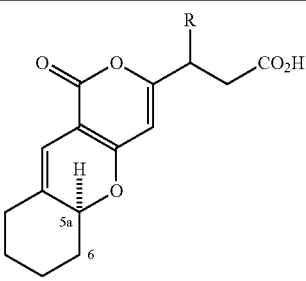
5a: R = H
5b: R = OH
5c: R = NH₂
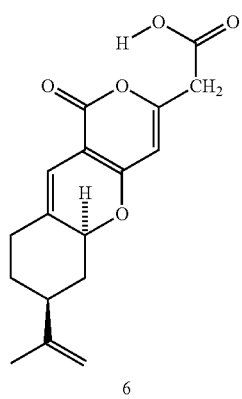
6
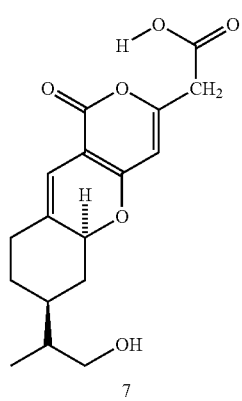
7
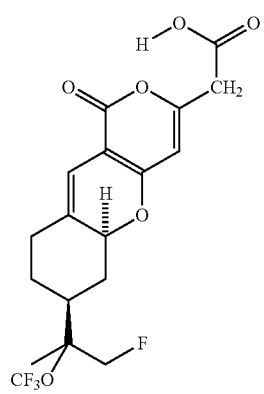
8
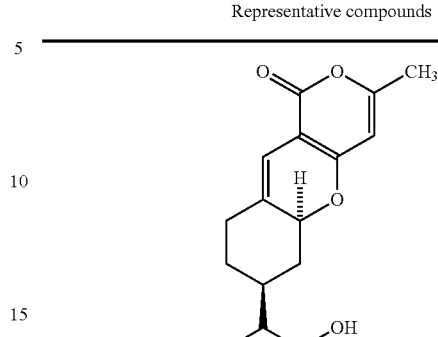
9
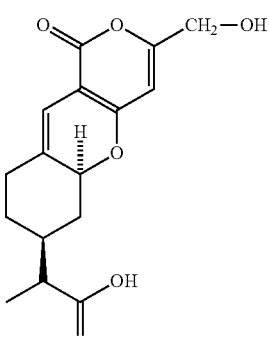
10
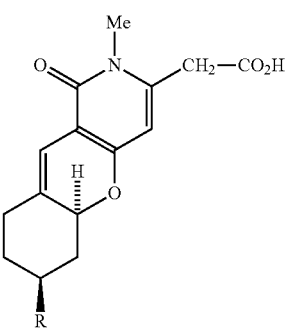
11: R = H
12: R = —CMe=CH₂

TABLE 2-continued

Representative compounds

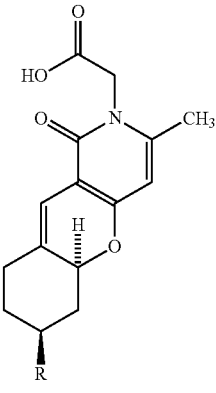

13: R = H
14: R = —CMe═CH$_2$

Preferred compounds are those specifically depicted and described in this disclosure. A class of compounds of this invention includes Compounds 2, 3, 6, 7, 8, 9, 10, 11, 12, 13 and 14. A further class of compounds of this invention includes homologs of the foregoing compounds. A preferred class of compounds includes those where T and Z are C and X and Y are O. A preferred class of compounds includes those where $R^1$ is $CH_2CO_2H$. A preferred class of compounds includes those where Z is C and $R^8$ and $R^9$ are H. A class of compounds of this invention are those that inhibit aldose reductase to the same or greater extent than currently available aldose reductase inhibitors, including Tolrestat. A class of compounds of the invention are those that are water soluble.

The methods of the invention are useful in treating the diseases and disorders described herein in patients. Patients include small mammals, humans, large mammals, livestock animals, pets and laboratory animals. Preferably, the patient is a human or dog.

This invention also provides methods for inhibiting aldose reductase in cells, particularly lens epithelial cells, comprising contacting the cells with a tricyclic compound as disclosed herein, preferably in cell-permeable, water-soluble form. Methods are also provided for reducing the effects of high glucose and protein kinase C in tissues via administration of such compounds. This invention provides such compounds in suitable pharmaceutical carriers in dosages effective to provide measurable therapeutic results in inhibiting aldose reductase and ameliorating symptoms of cataract and/or diabetic retinopathy. Preferably, the compounds used in the methods of this invention are at least as effective or more effective inhibitors of human retina aldose reductase than Tolrestat, Sorbinil or other known aldose reductase inhibitors. One or more compounds of the invention may be used in combination.

Certain compounds were disclosed in U.S. Pat. No. 5,958,970 and U.S. Pat. No. 6,384,045, incorporated herein by reference to the extent not inconsistent herewith, and specifically for their disclosures of methods of preparing the subject compounds and for analogs of the compounds disclosed herein having substituents as defined herein. Methods of using such compounds as aldose reductase inhibitors are provided herein.

Compounds of this invention may be prepared and used without undue experimentation by those skilled in the art of synthetic chemistry by methods analogous to those specifically disclosed herein or in publications and patent applications incorporated by reference. Methods of selecting those compounds which are effective for inhibiting aldose reductase in cells to a desired level are performed without undue experimentation by those skilled in the art by the methods described herein, or those methods known in the art. Methods of selecting those compounds which are effective for treatment of Alzheimer's disease, inhibition of ACAT, inhibition of CETP and protecting cells that at least partially express APP fusion protein from cell death are performed without undue experimentation by those skilled in the art by the methods described herein, or those methods known in the art.

Compounds containing any combination of substituents or members of the Markush groups specified above are within the scope of the invention. All substituents of the compounds of the invention may be the same, all substituents may be different, or any combination of substituents may be the same or different. Compounds having substituents with a specified function, for example those that impart water solubility to the compound form a special class of compounds of this invention.

The substituents included in the compounds and used in the methods of the invention may be any substituent not having structures or reactivity which would substantially interfere with the desired aldose reductase inhibition or other desired activity of the compound, as may readily be determined without undue experimentation by those skilled in the art, for example, by using the assay methods disclosed herein. Preferably the substituents do not interfere with water-solubility of the compound.

Effective dosages of the compounds of this invention may be easily determined by those skilled in the art following the teachings hereof and principles known to the art.

The compounds of these inventions may be administered in the form of pharmaceutical preparations including the compounds of these inventions in suitable pharmaceutical carriers to form solutions, lotions, creams, and other dosage forms known to the art. Combinations of such compounds with pharmaceutical carriers are also provided by this invention.

DEFINITIONS

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to Si, O, S, P and N atoms. The term hydrocarbyl includes, but is not limited to alkyl, alkenyl, alkynyl, ether, polyether, thioether, straight chain or cyclic saccharides, ascorbate, aminoalkyl, hydroxylalkyl, thioalkyl, aryl and heterocyclic aryl groups, optionally substituted tricyclic molecules, amino acid, polyalcohol, glycol, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, Si, OH, SH, $NH_2$, COH, $CO_2H$, $OR_a$, SR$_a$, NR$_a$R$_b$, CONR$_a$R$_b$, where R$_a$ and R$_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are C$_1$-C$_6$ alkyl and include among others methyl, ethyl, n-propyl, and isopropyl groups.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropanyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to Si, OH, SH, NH$_2$, COH, CO$_2$H, OR$_c$, SR$_c$, P, PO, NR$_c$R$_d$, CONR$_c$R$_d$, and halogens, particularly chlorines and bromines where R$_c$ and R$_d$, independently, are alkyl, unsaturated alkyl or aryl groups. Preferred alkyl and unsaturated alkyl groups are the lower alkyl, alkenyl or alkynyl groups having from 1 to about 3 carbon atoms.

Unless otherwise specified, all groups may be optionally substituted.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl (—C$_6$H$_5$), or naphthyl (—C$_{10}$H$_7$). Suitable substituents for aryl groups include among others, alkyl groups, unsaturated alkyl groups, halogens, Si, OH, SH, NH$_2$, COH, CO$_2$H, OR$_e$, SR$_e$, NR$_e$R$_f$, CONR$_e$R$_f$, where R$_e$ and R$_f$ independently are alkyl, unsaturated alkyl or aryl groups. Preferred substituents are OH, SH, OR$_e$, and SR$_e$ where R$_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as —CO$_2$—, —CO—, —O—, —S—, —P—, —NH—, —CH=CH— and —(CH$_2$)$_R$— where R is an integer from 1 to about 5, and particularly —CH$_2$—. Examples of aryl groups having bridging substituents include phenylbenzoate. Substituents also include moieties, such as —(CH$_2$)$_R$—, —O—(CH$_2$)$_R$— or —OCO—(CH$_2$)$_R$—, where R is an integer from about 2 to 7, as appropriate for the moiety, which bridge two ring atoms in a single aromatic ring as, for example, in a 1,2,3,4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethylpropoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethylpropoxy) methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. "Amino acid" as used herein includes amino acid residues and amino acid side chains. An "amino acid residue" is an amino acid radical —NHCH(R)C(O)—, wherein R is an amino acid side chain, except for the amino acid residues of proline and hydroxyproline which are —N(CH$_2$—CH$_2$—CH$_2$)CHC (O)— and —N(CH—CHOHCH$_2$)CHC(O)—, respectively. An amino acid side chain is a radical found on the α-carbon of an α-amino acid as defined herein, where the radical is either hydrogen (side chain of glycine), methyl (side chain of alanine), or is a radical bonded to the α-carbon by a methylene (—CH$_2$—), or phenyl group.

"Contacting" reaction components with each other refers to providing a medium and/or reaction chamber in which the reaction components are placed together so that they can react with each other. Preferably, the reaction components are suspended or dissolved in a carrier fluid which is a liquid medium. "Maintaining reaction components in contact" means keeping the components together in such a way that they can react with each other. As used herein, "reaction conditions" indicates the temperature, reactant and solvent conditions necessary for a reaction to occur. Suitable reaction conditions are easily determined by one of ordinary skill in the art without undue experimentation.

"Straight chain or cyclic saccharides" include mono-, di- and poly-, straight chain and cyclic saccharides that are optionally substituted with an amino group which is optionally acetylated. Straight chain saccharides that are useful in this invention include but are not limited to those molecules with a chain of 5 or 6 carbon atoms with one or more —OH groups attached, to and either an aldehyde or ketone group. Cyclic saccharides are saccharides that are in a ring form. Disaccharides are compounds wherein two monosaccharide groups are linked. Polysaccharides are compounds wherein more than two monosaccharide groups are linked. Specific examples of saccharides useful in this invention include glucose, ribose and glucosamine, among others.

Substituents which impart water solubility include but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers.

Tricyclic compounds include all compounds having three saturated, unsaturated or partially saturated six-membered rings, preferably as depicted herein, with substituents as defined herein.

As used herein, "aspartate substituent" is:

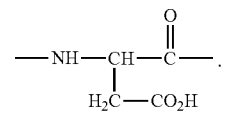

As used herein, "adenine group" is:

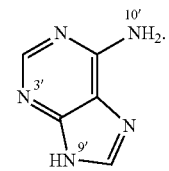

The adenine group can attach to another substituent through the 3', 9' or 10' group, and as known in the art, the valences of the nitrogens are adjusted accordingly. This is shown in the structures provided herein. "Adenine group" includes optionally substituted adenine groups, including those adenine groups substituted with one or more halogens, including radiolabeled halogens, including $^{125}$I.

This invention is also directed to pharmaceutically acceptable esters and salts of the tricyclic compounds of the various formulas and structures disclosed herein. Acid addition salts are prepared by contacting compounds having appropriate basic groups therein with an acid whose anion is generally considered suitable for human or animal consumption. Pharmacologically acceptable acid addition salts include but are not limited to the hydrochloride, hydrobromide, hydroiodide, sulfate, phosphate, acetate, propionate, lactate, maleate, malate, succinate, and tartrate salts. All of these salts can be prepared by conventional means by reacting, for example, the selected acid with the selected basic compound. Base addition salts are analogously prepared by contacting compounds having appropriate acidic groups therein with a base whose cation is generally considered to be suitable for human or animal consumption. Pharmacologically acceptable base addition salts, include but are not limited to ammonium, amine and amide salts.

Pharmaceutically acceptable esters of compounds of this invention are prepared by conventional methods, for example by reaction with selected acids. Pharmaceutically acceptable esters include but are not limited to carboxylic acid esters RCOO-D (where D is a cationic form of a compound of this invention and where R is H, alkyl or aryl groups).

This invention is also directed to prodrugs and derivatives which on being metabolized will result in any of the effective tricyclic aldose reductase inhibitors of this invention. For example, alkoxy or acetate groups can be metabolized to hydrogens. Labile substituents may be protected employing conventional and pharmaceutically acceptable protecting groups removable on metabolism. Pharmaceutically active compounds may be derivatized by conventional methods to provide for extended metabolic half-life, to enhance solubility in a given carrier, to provide for or facilitate slow-release or timed-release or enhance or affect other drug delivery properties.

Pharmaceutical compositions according to the present invention are provided which comprise one or more tricyclic compounds, salts or esters of this invention in association with a pharmaceutically acceptable carrier or excipient adapted for use in human or veterinary medicine. Such compositions may be prepared for use in conventional manner in admixture with one or more physiologically acceptable carriers or excipients. The compositions may optionally further contain one or more other therapeutic agents. The compounds, salts or esters of this invention are present in these pharmaceutical compositions in an amount or in a combined amount sufficient to elicit a measurable positive effect on a symptom or condition associated with aldose reductase, inhibition of ACAT, inhibition of CETP and protecting cells that at least partially express APP fusion protein from cell death or a measurable physiological effect. As known in the art, radiolabeled or fluorescent compounds are useful in many applications, including diagnostic applications.

The tricyclic compounds, salts and esters of this invention may be formulated for oral, buccal, parenteral, topical or rectal administration. In particular, they may be presented in unit dose form. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients, such as antimicrobial agents, or preservatives.

The invention further provides a process for preparing a pharmaceutical composition which comprises bringing a compound of the invention into association with a pharmaceutically acceptable excipient or carrier. The carrier or excipient being selected as is known in the art for compatibility with the desired means of administration, for compatibility with the selected compounds and to minimize detrimental effects to the patient.

The magnitude of a prophylactic or therapeutic dose of a particular compound will, of course, vary with the nature of the severity of the condition to be treated, the particular compound and its route of administration. It will also vary according to the age, weight and response of the individual patient, all as will be readily ascertainable to those skilled in the art.

The compounds of the present invention are preferably formulated prior to administration. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The term "unit dosage form" refers to physically discrete units suitable as unitary dosages for patients, including human subjects and other mammals, each unit containing a predetermined quantity of active material calculated to produce the desired therapeutic effect, in association with a suitable pharmaceutical carrier.

This invention is further directed to therapeutic methods employing the compounds of this invention and pharmaceutical compositions containing them in the treatment of disorders or physiological conditions involving disorders due to the activity and presence of aldose reductase. These methods comprise a step of administering to a patient having the disorder or symptoms thereof a pharmaceutical composition comprising one or a mixture of the compounds, salts or esters of this invention where the compounds, or mixtures of compounds of this invention are present in the composition at a level or a combined level sufficient to effect a positive biological response (an "effective amount"). The present invention provides compounds that can be used in place of or in combination with currently known pharmaceuticals active against disorders such as cataract and diabetic retinopathy and treatment of Alzheimer's disease. Compounds of this invention exhibit improved properties (enhanced activity and/or decreased undesired side-effects) for treatment of such disorders as compared to previously known compounds useful for such treatments.

DETAILED DESCRIPTION OF THE INVENTION

Figure 1A:
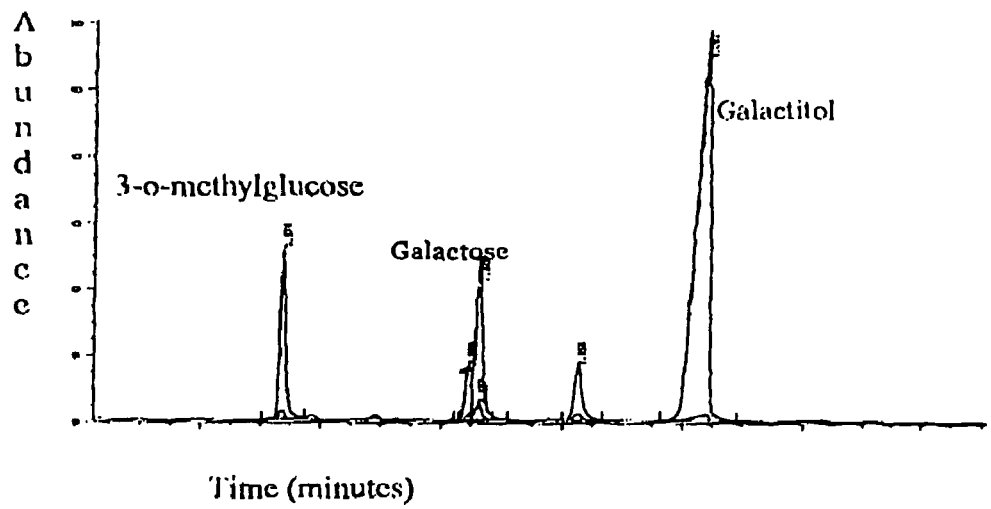
FIG. 1A shows the GC plot of polyol fraction from lens epithelial cells grown for 48 hours in 40 mM galactose [Peak 1 at 6.6 minute is 3-O-methylglucose (a standard was added for quantification of the other peaks); Peak 2 at 7.25 minute is galactose; Peak 3 at 8 minute is galactitol (the polyol)].

Applicant does not wish to be bound by any theory presented herein.

Bioactivity Assays

The activity of the drugs is tested in various ways, including tissue culture assays and assays testing aldose reductase inhibition. For the tissue culture assay, a lens epithelial cell line is grown in galactose with or without the drug. Cells are tested for polyol accumulation by GC/mass spectrometry. Levels of PKC are tested in homogenized cell pellets or in samples of lens, retina or sciatic nerves from treated patients. Tissue is homogenized and tested for PKCγ levels using Western blots. These procedures are described in more detail below.

Human aldose reductase (AR) was obtained from overexpression of the human AR gene in an *E coli* system and was purified by column chromatography using a talon metal affinity column and eluted with a gradient mixture of Tris, NaCl buffer and imidazole solution. The human AR inhibition assay was conducted as follows. In a sample cuvette, 25 mM of D-xylose (75 mg/mL) and 0.15 mM of reduced nicotinamide adenine dinucleotide phosphate (NADPH) (4 mg/mL), and various amount of the inhibitor [in PBS (phosphate buffer saline) solution; the concentration of the inhibitor was determined using UV spectroscopy based on $\epsilon_{max}$ at $\lambda_{max}$ of the drug] in 700 uL of PBS (a solution made of 1.44 g of $Na_2HPO_4$, 0.24 g $KH_2PO_4$, 0.2 g KCl, and 8 g NaCl in 1 L of distilled water) buffer (pH=6.1) solution and 200 uL of the AR enzyme (a final volume of 1 mL was obtained). The intensity of absorption of NADPH ($\lambda_{max}$=340 nm) was measured. When xylose is reduced to xylitol, NADPH is converted into NADP and the absorption at 340 nm decreases. When AR is inhibited by the drug, the absorption at 340 nm of NADPH remains unchanged. Each assay was repeated three times and an average $IC_{50}$ value was obtained. Several tricyclic pyrones were tested for the inhibition of AR along with Tolrestat (obtained from Ayerst Laboratories Research, Inc., Princeton, N.J.) and Sorbinil (obtained from the procedure given in *Structure* 1997, 5, 601-612) and the data are summarized in Table 3. Contrary to Tolrestat, compounds 1 and 2 are water soluble materials. As shown, compound 1 has greater inhibitory activity than Tolrestat and Sorbinil.

TABLE 3

Inhibition of Human Retina Aldose Reductase.

| Inhibitor | Compound 1 | Compound 2 | Tolrestat | Sorbinil |
|---|---|---|---|---|
| $IC_{50}$ | 2 nM | 20 nM | 5 nM | 2 μM |

Compounds 1 and 2 (up to 100 uM) have been added to bovine lens epithelial cells and no toxicity was found.

The enzyme assay was also performed for other compounds, as shown in Table 4.

TABLE 4

$IC_{50}$ values obtained from the enzyme assay (aldose reductase)

| Compound | $IC_{50}$ |
|---|---|
| 1 | 0.002 μM |
| 3 | >500 μM |
| 2 | 0.020 μM |
| 5c | 200 μM |
| 6 | No significant inhibition detected |
| 7 | No significant inhibition detected |

The ability of the drugs to inhibit galactitol formation from galactose was also studied in N/N 1003 lens epithelial cells. Two sets of lens cells were grown in media with (control) or without 40 mM galactose. Various concentrations of inhibitors were added initially and the cells were grown for 48 hours. The cells were lysed and galactose and galactitol were extracted out and the concentrations were determined using gas chromatography and mass spectrometry by silylating the crude extract with excess of trimethylsilyl chloride, trimethylsilyl imidazole and pyridine at 70° C. for 1 h. The results are summarized in Tables 5 and 6.

TABLE 5

% galactitol for varying concentrations of compound 1

| Concentration of 1 (uM) | % galactitol |
|---|---|
| 1 | 80 |
| 10 | 30 |

TABLE 6

% galactitol for varying concentrations of Tolrestat

| Concentration of Tolrestat (uM) | % galactitol |
|---|---|
| 0.5 | 100 |
| 1 | 90 |
| 7 | 53 |

Figure 1B:
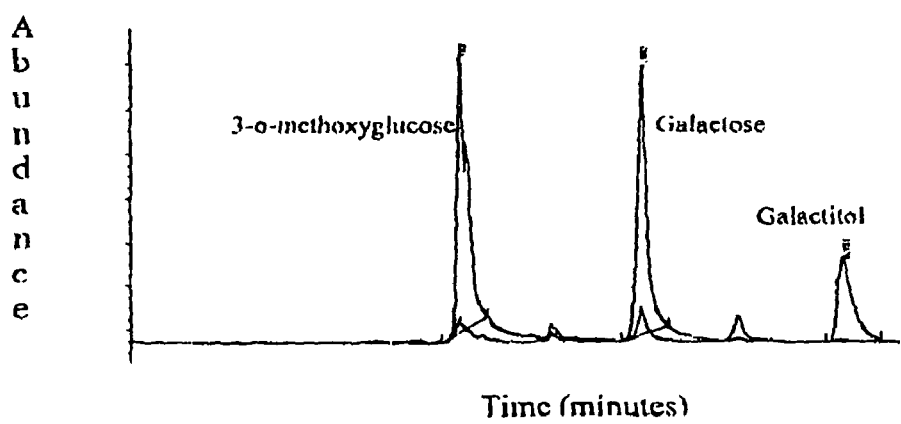
FIG. 1B shows the GC plot of polyol fraction from lens epithelial cells grown for 48 hours in 40 mM galactose and 10 uM compound 1 [Peak 1 at 6.6 minute is 3-O-methylglucose (a standard was added for quantification of the other peaks); Peak 2 at 7.25 minute is galactose; Peak 3 at 8 minute is galactitol (the polyol)]

FIG. 1A is the GC/MS data showing the relative galactose and galactitol contents for lens epithelial cells grown for 48 hours in 40 mM galactose. Peak 1 at 6.6 minute is 3-O-methylglucose (a standard was added for quantification of the other peaks); Peak 2 at 7.25 minute is galactose; Peak 3 at 8 minute is galactitol (the polyol). FIG. 1B is the GC/MS data showing the relative galactose and galactitol contents for lens epithelial cells grown for 48 hours in 40 mM galactose and 10 uM compound 1. As shown in the figures, addition of compound 1 decreases the concentration of galactitol relative to galactose.

TABLE 7

Results of tissue culture assay of inhibitors 1, 2, 3, and 5c
(the number of trials is in parenthesis)

| Inhibitor (10 uM) | % inhibition |
| --- | --- |
| 1 | 80 ± 10 (3) |
| 3 | <10 (2) |
| 2 | <10 (2) |
| 5c | 43 ± (2) |
| Tolrestat | 95 ± 4 (3) |

Table 7 shows results of tissue culture assay of inhibitors 1, 2, 3, and 5c. 40 mM galactose media was supplemented with 10 uM inhibitor and fed to lens epithelial cells for 48 hours.

The $IC_{50}$ values for compound 1 is 6 uM (in lens cells) and for Tolrestat is 8 uM. These data shows that compound 1 is a slightly better AR inhibitor than Tolrestat. Since Tolrestat is insoluble in water, in the lens cells study, the sodium salt of Tolrestat was made by treating with NaOH and used. On the other hand, compound 1 is water soluble and was used as it is.

Computational Docking Experiments

Computational docking experiments of various synthesized materials (such as 1 and 2) and other structures with aldose reductase (the X-ray structure is known: see Urzhumtsev, A. et al. A 'specificity' pocket inferred from the crystal structures of the complexes of aldose reductase with the pharmaceutically important inhibitors tolrestat and sorbinil. *Structure* 1997, 5, 601-612) were performed. A tight binding between the inhibitor and AR (binding energy, $K_i$=−77 Kcal/mol), and hydrogen bonding between the carboxylic acid group of 1 with residues H is 110 (2.81 Å) and Trp111 (2.76 Å) of AR were found (data not shown). Computer docking experiments show that other derivatives such as compounds 5-14 have similar or better binding energies than 1. Therefore, they would be expected to inhibit aldose reductase activity to a similar or greater extent as 1.

Diabetic Rat Model.

An 8 week study to determine the effects of streptozotocin diabetes on vascular leakage as measured by fluorophotometry, retinal ultrastructure as measured by electron miscoscopy, and on PKC levels as measured by Western blot has been completed. Diabetes was monitored by blood glucose levels. The fluorophotometry was measured using an instrument which is available in the Veterinary School Ophthalmology Department which has been adapted for rats. Vascular leakage was measured during the 8-week period to determine the effects of AR inhibitors. Eyes from the diabetic and normal animals were fixed and processed at the Pathology Facility and retinal ultrastructure was determined. The photoreceptors of diabetic animals are swollen, disorganized and reduced in length. The outer-nuclear layer was about one-half the distance from the RPE in the diabetic rats compared to the distance in the healthy rats. The diabetic rat photoreceptor depth was reduced by 55-60% compared to healthy photoreceptors. The RPE was also altered in structure but no change in phagosome number was noted. PKC levels were increased as shown by both enzyme assays and by Western blots.

In order to test for in vivo effects of ARI's, rats were fed a 40% galactose diet for 9 days and the accumulation of galactitol was measured in lens tissue. This tissue has high aldose reductase activity and the eye has a separate vasculature. Thus, if the ARI works in the lens this is a good indication that the drug works and can penetrate to most tissues.

The specific experimental details follow. Six-week-old Sprague Dawley Rats (250-300 g) were fed normal chow (Bioserve rodent grain base diet 50% fiber F3975), high galactose chow (Bioserve Rodent grain base diet 50% galactose F1624), normal chow with inhibitor, or high galactose chow with either the inhibitor (100 mg/Kg body weight per day) or Tolrestat (100 mg/Kg body weight per day). The rats were given food supplemented with inhibitor in the morning and then given food and water ad libitum the rest of the day. They were kept on a 12-hour on and 12-hour off light cycle. After 9 days, the rats were sacrificed with an overdose of $CO_2$ and then eyes were taken and immediately frozen on dry ice for later polyol and PKC analyses. Experiments on all rats conformed to the ARVO resolution on the Use of Animals in Research.

Polyol Content:

The lenses were removed and weighed. They were placed in 500 μL of PBS supplemented with 15 μL of 3-O-methoxyglucocse as internal standard. The lenses were then boiled for 20 minutes and 100 μL of 0.3 M zinc sulfate and 100 μL of barium sulfate were added. The mixture was centrifuged for 15 minutes at 10,000 g. The supernatant was removed and lyophilized for GC/MS analysis.

PKC Analysis of Diabetic and Galactosemic Rat Lens:

The lenses were removed from the enucleated eyes and weighed. They were put in 200 μL lysis buffer (50 mM Tris, 100 mM NaCl, M-Per Pierre Zwitterionic detergent, 5 mM NaF, 1 mM $Na_3VO_4$, 40 mM β-glycerophosphate, 6 μg/mL chymotrypsin, 10 μM3,4-dichlorocoumarin, 10 μM E-64, 1 μg/mL leupeptin, 1 μg/mL pepstatin A, 1 μg/mL aprotinin, 1 mM PMSF, and 5 mM EDTA (Sigma). The lenses were then ground using a tissue grinder until they were a uniformly white solution. They were then sonicated to make certain all the cells were disrupted. The mixture was then centrifuged for 20 minutes at 0° C. at 3 g. The supernatant was then analyzed for protein content using BSA assay (Pierce). Equal amounts of protein were loaded and separated on a 10% SDS polyacrylamide gel. The proteins were transferred to nitrocellulose (Midwest Scientific; pore size 0.45 μm). The western was blocked with a 3% milk solution, and then mouse anti-PKC γ (1:5000) or PKC α (1:1000) antisera (Transgenic Laboratories) were applied in a 3% milk solution overnight. The membrane was then washed 3 times in TDN (0.05 M NaCl, 2 mM EDTA, 0.01 M Tris) and goat anti-mouse antisera IgG (1:5000 Promega) was applied. The autoradiogram was developed using supersignal chemiluminescent substrate from Pierce.

Figure 2:
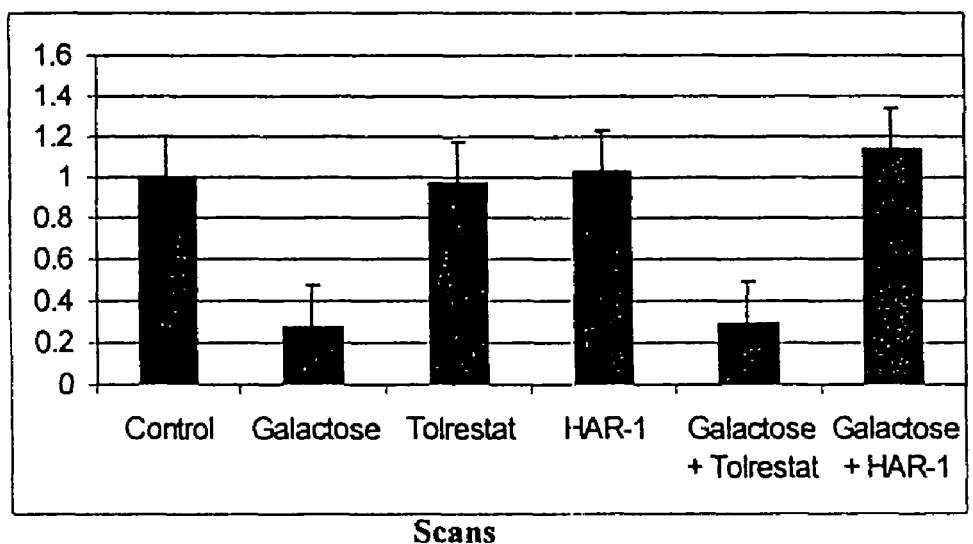
FIG. 2 shows PKC-γ content in lens epithelial cells of control, Galactose, tolrestat, compound 1 (HAR1), tolrestat/Galactose, and compound 1/galactose rats.

Lens epithelial cells exposed to 40 mM galactose exhibit a 50% decrease in PKC-γ. The effects of streptozotocin induced diabetes on PKC-γ levels in rat lens have been measured. The rat lens of diabetic animals show a 50~70% decrease in PKC-γ levels (data not shown). Rats exposed to 40% galactose for 9 days also had reduced PKC-γ levels as demonstrated by Western blots and when compared to rats fed a control diet. The galactose-fed animals were also fed with 100 mg/Kg body weight per day of compound 1 or Tolrestat. FIG. 2 shows the PKC-γ content in lens epithelial cells of control, Galactose, tolrestat, compound 1 (HAR1), tolrestat/Galactose, and compound 1/galactose rats. It is seen that the PKC-γ levels remain high when compound 1 is used.

Figure 3A:
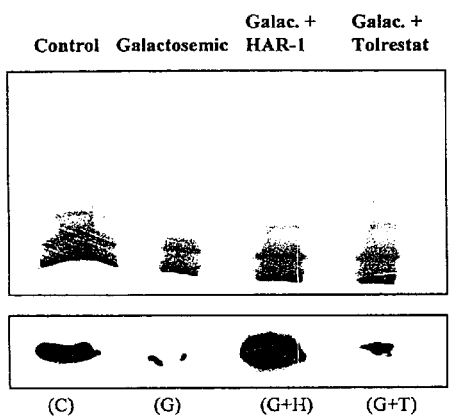
FIG. 3 shows data for lens cells (3A) and sciatic nerve cells (3B) of diabetic rats under various conditions.
Figure 3B:
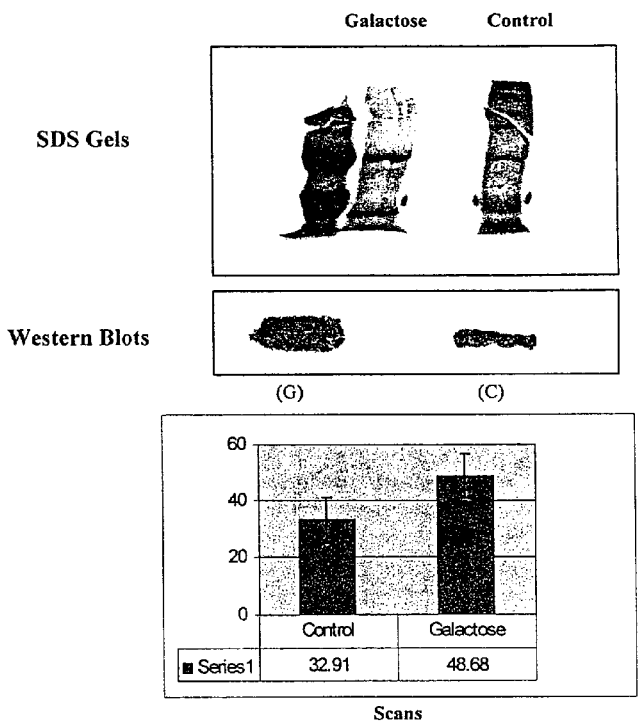

The results are shown in FIG. 3A for the lens cells which shows that when the animals were fed 40% galactose feed, the lens epithelial cell PKC-γ decreased, and when the animals were given compound 1 or Tolrestat with the high galactose feed, the PKC-γ levels remained near normal (control levels). Moreover, pathology studies indicate that the drug is not toxic to the rats. FIG. 3B shows Western blots for sciatic nerve cells which indicate that the PKC-γ levels were decreased in these animals and that this was normalized when fed with compound 1 or Tolrestat and compound 1 provided a greater level of normalization than Tolrestat. The lower graph in FIG. 3B shows the readout intensities from the upper graph.

Canine Study

Figure 4:
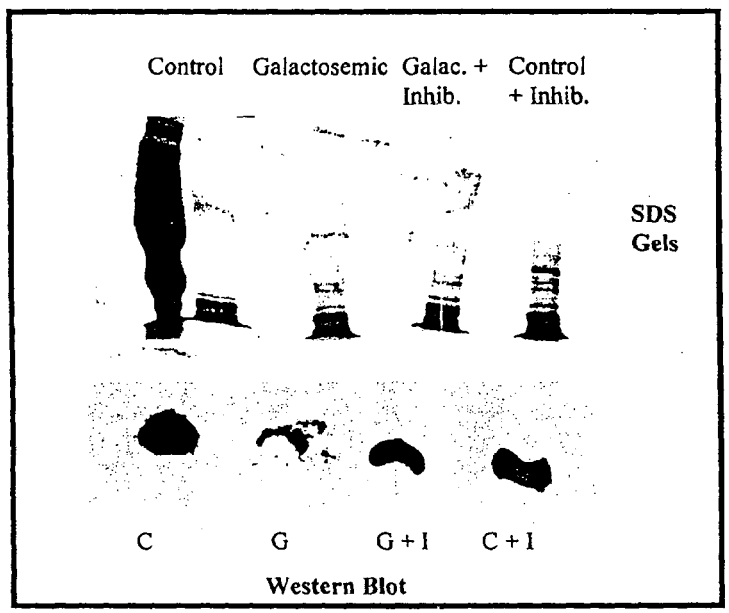
FIG. 4 shows SDS gels and Western blots illustrating the effects of compound 1 in lens cells of diabetic dogs.
Figure 5:
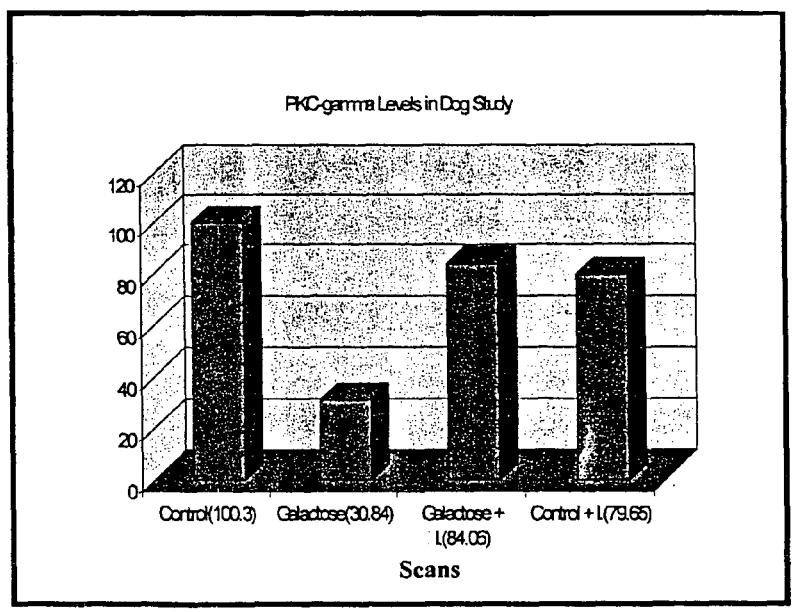
FIG. 5 shows PKC-gamma levels in the lenses of control dogs, dogs fed a galactose-rich diet, dogs fed a galactose-rich diet and treated with compound 1, and control dogs treated with compound 1.

A pilot study was conducted to determine initial toxicity and efficacy in a Beagle model. The study was conducted at the fully accredited facility at the Kansas State University Veterinary Clinic. The dogs were fed a 40% galactose diet for 6 weeks. These dogs developed cataracts. Compound 1 was administered orally at 100 mg/kg body weight/day for 6 weeks. At this dose, the polyol levels were 50% normalized (FIG. 4) and PKCγ levels were 80% normalized (FIG. 5). FIG. 4 shows the results of the Western Blot of the PKC-γ level of dog lens from control (C; normal dogs), treated with galactose (G), galactose and inhibitor 1 (G+I) and control with inhibitor 1 (C+I). As shown, the PKC-γ levels of the control, G+I and C+I are similar but levels of G are significantly decreased. FIG. 5 shows the read-out of intensities of PKC-γ levels from FIG. 4. The PkC-γ levels of dogs treated with galactose is 30.8%, G+I is 84.1% and C+I is 79.7%. The GC/MS data of the level of polyol in dog lens is shown in Table 8. Additional testing at higher doses is planned to determine optimal dose for efficacy with no or low toxicity. These experiments are well within the skill and experience of one of ordinary skill in the art and can be performed without undue experimentation.

TABLE 8

| Galactosemic | Galactose | Galactitol (polyol) |
|---|---|---|
| With inhibitor | 72.7% | 27.3% |
| Without inhibitor | 43.3% | 56.7% |

Biological Activity Results for TP Compounds

The reported procedures for the inhibitory activities of ACAT (Tomoda, H.; Nishida, H.; Masuma, R.; Cao, J.; Okuda, S.; Omura, S. J. Antibiot. 1991, 44, 136-143), CETP (Tomoda, H.; Tabata, N.; Masuma, R.; Si, S.-Y.; Omura, S. J. Antibiot. 1998, 51, 618-623; D. H. Hua et al. Tetrahedron 2003, 59, 4795-4803), L1210 tumor cells (Perchellet, E. M.; Ladesich, J. B.; Magill, M. J.; Chen, Y.; Hua, D. H.; Perchellet, J. P. Anti-Cancer Drugs 1999, 10, 489-504), and APP C99-induced cell death (Jin, L.-W.; Hua, D. H.; Shie, F.-S.; Maezawa, I.; Sopher, B.; Martin, G. M. J. Mol. Neurosci. 2002, 19, 57-61) were followed.

ACAT mediates the esterification of intracellular cholesterol and is believed to play a key role in lipoprotein metabolism and atherogenesis (for a review: Suckling, K. E.; Stange, E. F. J. Lipid Res. 1985, 26, 647-671). Studies of the inhibition of ACAT with tricyclic pyrone analogs were carried out first; the TP results are summarized in Table 9. Esters 101-103 showed activity with $IC_{50}$ values of 157, 310, and 150 μM, respectively. Under the same conditions, the $IC_{50}$ value of pyripyropene A was 0.1 μM. The inhibition of CETP with these three compounds was then studied. CETP, a hydrophobic neutral glycoprotein, mediates the transfer of cholesteryl ester from high-density lipoprotein to low-density lipoprotein (For a review: Tall, A. R. J. Lipid Res. 1993, 34, 1255-1274). The $IC_{50}$ value of compound 103 was 75 μM, while the values of compounds 101 and 102 were >100 μM. A number of amides derived from the attachment of natural amino acid at C12 of 101 and the modification at the isopropenyl side chain such as with a linkage of an adenine (Adenine containing carbocycles are reported to possess antitumor and antiviral activities: Hayashi, M.; Yaginuma, S.; Muto, N.; Tsujino, N. Nucleic Acid Res. Symp. Ser. 1980, 8, s65-s67; Yaginuma, S.; Muto, N.; Tsujino, M.; Sudata, Y.; Hayashi, M.; Otani, M. J. Antibiot. 1981, 34, 359-366; De Clercq, E. Antimicrob. Agents Chemother. 1985, 28, 84-89) moiety at C14, i.e. compounds 105-107, were synthesized and evaluated. The N-(p-nitrophenyl)aspartamide portion of 104 was attached in order to study whether 104 was a substrate of caspase 103 (For a review: VIIIa, P.; Kaufmann, S. H.; Earnshaw, W. C. Trends Biochem. Sci. 1997, 22, 388-393). The in vitro study of 104 with caspase 103 showed no release of p-nitroaniline, which indicated that 104 is not a substrate. However, compounds 104 and 106 (code named CP2) protected from death MC65 cells that conditionally expressed with a partial APP fusion protein (amino-17 residues+carboxy-99 residues (Sopher, B. L.; Fukuchi, K.; Smith, A. C.; Leppig, K. A.; Furlong, C. E.; Martin, G. M. Brain Res. Mol. Brain. Res. 1994, 26, 207-217) in the absence of tetracycline. The $EC_{50}$ (effective concentration at 50%) values of 104 and 106 were 2.0 and 0.15 μM, respectively. Surprisingly, N-9' analog 105, a regioisomer of 106, was 20-fold less active ($EC_{50}$=3.0 μM) than 106, while N-10' analog 107, another regioisomer of 106 was inactive. It is presently uncertain why 106 is the most active compound, but it may be associated with the water solubility of N3'-adenine 106, in contrast to that of the N9'- and N10' derivatives 105 and 107, or their position of substitution on the adenine ring. Adenine itself shows no activity. Compound 105 is cytotoxic to L1210 tumor cells, with $IC_{50}$=30 μM. Aggarwal et al., J. Chem. Soc., Perkin Trans I (1999) 3315-3321 is incorporated by reference to the extent not inconsistent with the disclosure herewith.

TABLE 9

Biological activities of various Tricyclic pyrones (TPs)

| Compounds | $IC_{50}$, ACAT | $IC_{50}$, CETP | $C_{50}$, L1210 Leukemic Cells | $EC_{50}$, Protection of APP C99-Induced Cell Death |
|---|---|---|---|---|
| 101 | 157 μM | >100 μM | - | - |
| 102 | 310 μM | >100 μM | - | - |
| 103 | 150 μM | 75 μM | - | - |
| 104 | 168 μM | >180 μM | - | 2.0 μM |
| 105 | - | - | 30 μM | 3.0 μM |
| 106 | >500 μM | >250 μM | - | 0.15 μM |
| 107 | - | - | - | >3.0 μM |
| 108 | 167 μM | - | - | >10 μM |
| Pyripyropene A | 0.1 μM | - | >100 μM | - |
| Adenine | - | - | - | >10 μM |

Various tricyclic pyrones containing ester and amide side chains at C3 were synthesized from a regioselective deprotonation of C3 methyl group followed by carbonylation with carbon dioxide or benzyl chloroformate. Tricyclic pyrones containing alkyl side chains at C7 possessing an adenine moiety were also synthesized by a chemoselective hydroboration of C7 isopropenyl group followed by functional group transformation. Chemical modification of the functionalized tricyclic pyrones gives a library of analogs for biological evaluation. Other compounds in this library are synthesized using the methods described herein and known to those of ordinary skill in the art without undue experimentation. Compared with the moderate ACAT and CETP activities of TP analogs possessing an ester side chain at C3 of the pyrone ring (i.e. compounds 101-103), $EC_{50}$ values of compounds 104 and 106 are 2.0 and 0.15 μM, respectively, in the protection of neuron-cell death from the toxicity of intracellular accumulation of Aβ or Aβ-containing C-terminal fragments (CTF) of APP.

Synthesis

A class of new compounds; namely, 1H,7H-5a,6,8,9-tetrahydro-1-oxopyrano[4,3-b][1]benzopyranes, has been synthesized from a one-pot condensation of 6-substituted 4-hydroxy-2-pyrones and cyclic α-enals in high yields. The chemistry has been reported in several publications (see Hua, D. H., et al. A One-Pot Condensation of Enals and Pyrones. Synthesis of Novel 1H,7H-5a,6,8,9-Tetrahydro-1-oxopyrano[4,3-b][1]benzopyrans. *J. Org. Chem.* 1997, 62, 6888-6896; Hua, D. H. et al (5aS,7S)-7-Isopropenyl-3-methyl-1H,7H-5a,6,8,9-tetrahydro-1-oxopyrano[4,3-b][1]benzopyran. *Acta Cryst.* 1997, C53, 1995-1997) For example, treatment of pyrone 20 (commercially available) with 1 equiv of cyclohexenecarboxaldehyde (21) and 0.5 equiv of L-proline in ethyl acetate at 70° C. for 12 h afforded a 76% yield of tricyclic pyrone 23 (Scheme 1). Significantly, when (S)-(−)-perillaldehyde (22; commercially available) was used, a single enantiomer, 24 (78% yield), was isolated. These compounds were identified by spectroscopic data and single-crystal X-ray crystallography (see Hua, D. H.; Chen, Y.; Robinson, P. D.; Meyers, C. Y. (5aS,7S)-7-Isopropenyl-3-methyl-1H,7H-5a,6,8,9-tetrahydro-1-oxopyrano[4,3-b][1]benzopyran. *Acta Cryst.* 1997, C53, 1995-1997). Compound 24 and all compounds that contain C-7 substituents are optically pure. It should be noted that the enantiomer of 22 had been prepared by us from the oxidation of (R)-(+)-perillyl alcohol (commercially available) with Dess-Martin periodinane (85% yield) (Dess, D. B.; Martin, J. C. Readily accessible 12-I-5 oxidant for the conversion of primary and secondary alcohols to aldehydes and ketones. *J. Org. Chem.*, 48, 4155-4156, 1983).

Hence, the enantiomer of 22 can be synthesized from the condensation reaction using (R)-(+)-perillaldehyde. The carboxylic acid group was readily introduced by treating pyrone 23 and 24 separately with lithium diisopropylamide (LDA) in THF followed by $CO_2$ gas and then HCl (Scheme 2). Compounds 1 (94% yield) and 6 (90% yield), respectively, were obtained.

Scheme 1

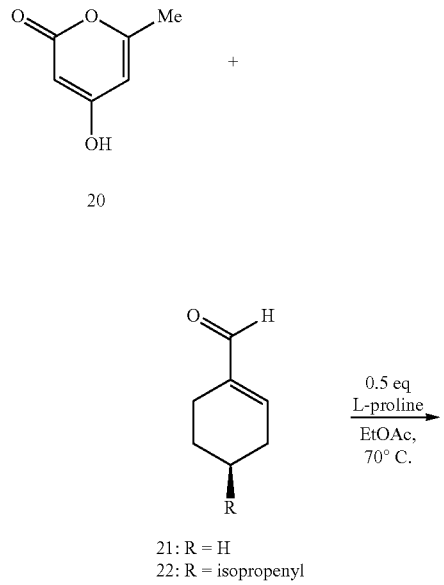

Scheme 2

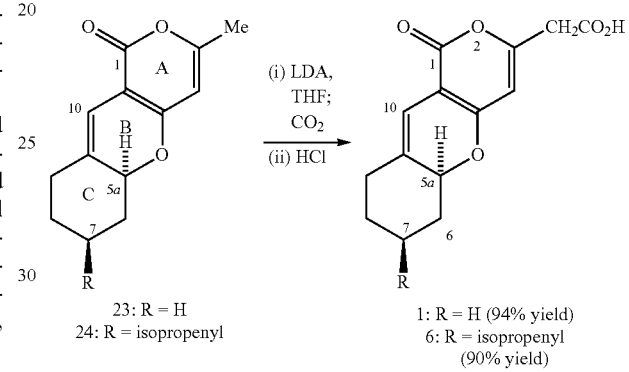

Large quantity (~2 grams) of compound 1 have been prepared for animal studies.

Compound 3 was produced from 23 by the sequence: (i) treatment with LDA followed by n-butyl glyoxylate (87% yield); and (ii) basic hydrolysis of the ester function of intermediate 25 with 1% NaOH followed by acidification with HCl (91% yield) (Scheme 3). Carboxylic acid 2 was produced by the hydroboration of the C-10 double bond of 25 with borane•THF followed by 30% $H_2O_2$ and 0.1% NaOH and then basic hydrolysis with NaOH.

Scheme 3

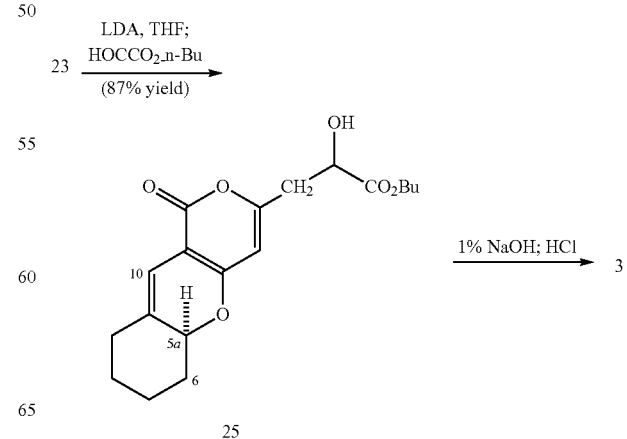

To alter the length of the tether carboxylic acid group attached at C-3 of the tricyclic pyrone, we also synthesized carboxylic acid 4 by a sequence: (i) deprotonation of pyrone 23 with LDA in THF followed by MoO₅.HMPA.pyridine (Vedejs, E.; Engler, D. A.; Telshow, J. E. *J. Org. Chem.* 1978, 43, 188); (ii) oxidation of the resulting alcohol 26 with Dess-Martin periodinane in methylene chloride; and (iii) oxidation of the resulting aldehyde 27 with silver oxide in acetonitrile (Scheme 4).

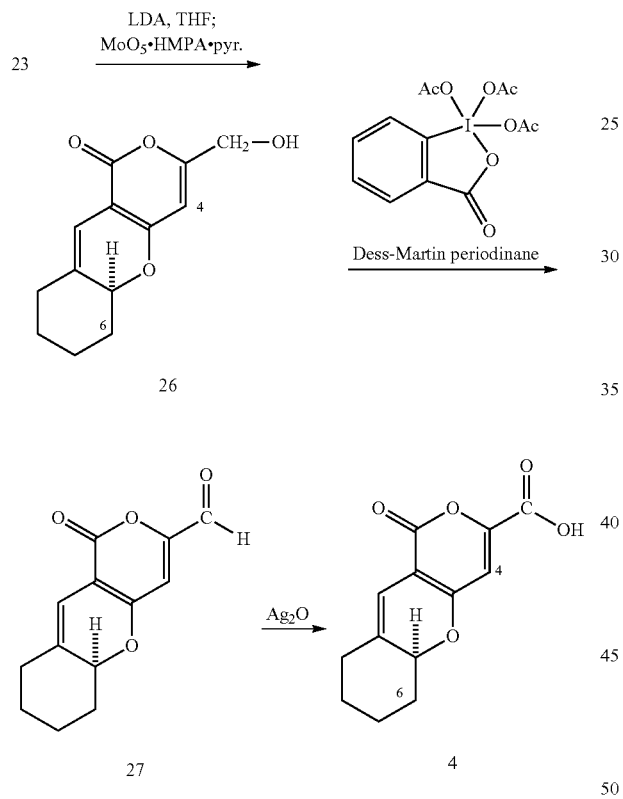

Compounds 5a, 5b, and the derivative of 5c were synthesized from alcohol 25 as outlined in Scheme 5. Hence, mesylation of alcohol 25 with methanesulfonyl chloride and triethylamine in methylene chloride followed by elimination with 1,8-diazabicyclo[5.4.0]undec-7-ene (DBU) in toluene gave a 69% yield of ene ester 28. Selective reduction of the side chain alkene of 28 with diimide followed by basic hydrolysis of the butyl ester function afforded carboxylic acid 5a. The side chain alkene of 28 was also selectively reacted with borane in THF followed by 30% hydrogen peroxide and 0.1% NaOH and the basic hydrolysis to give β-hydroxy carboxylic acid 5b. Michael-type addition of ene ester 28 with methylamine in THF at 0° C. followed by basic hydrolysis generated amino acid 29. Compounds 5a, 5b, and 29 are all water soluble materials.

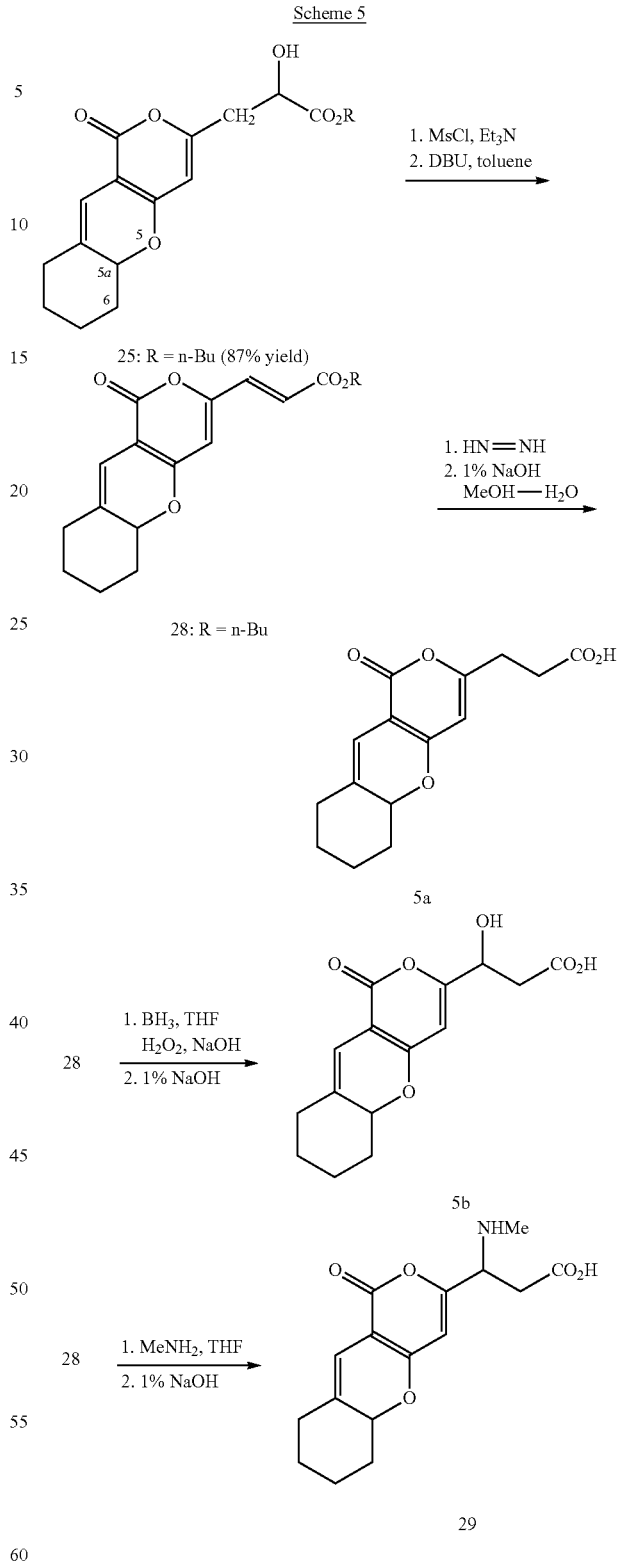

Carboxylic acid 7 was synthesized from tricyclic pyrone 24 (Scheme 6). Hence, formylation of 24 with LDA in THF at −78° C. followed by benzyl chloroformate gave an 83% yield of ester 30. Selective hydroboration of the C-11 double bond of 30 with 1 equiv of borane in THF at 0° C. followed by oxidation with 30% hydrogen peroxide and 0.1% NaOH afforded a 69% yield of alcohol 31. Basic hydrolysis of ester 31 with 1% NaOH in MeOH and water provided acid 7 (89% yield).

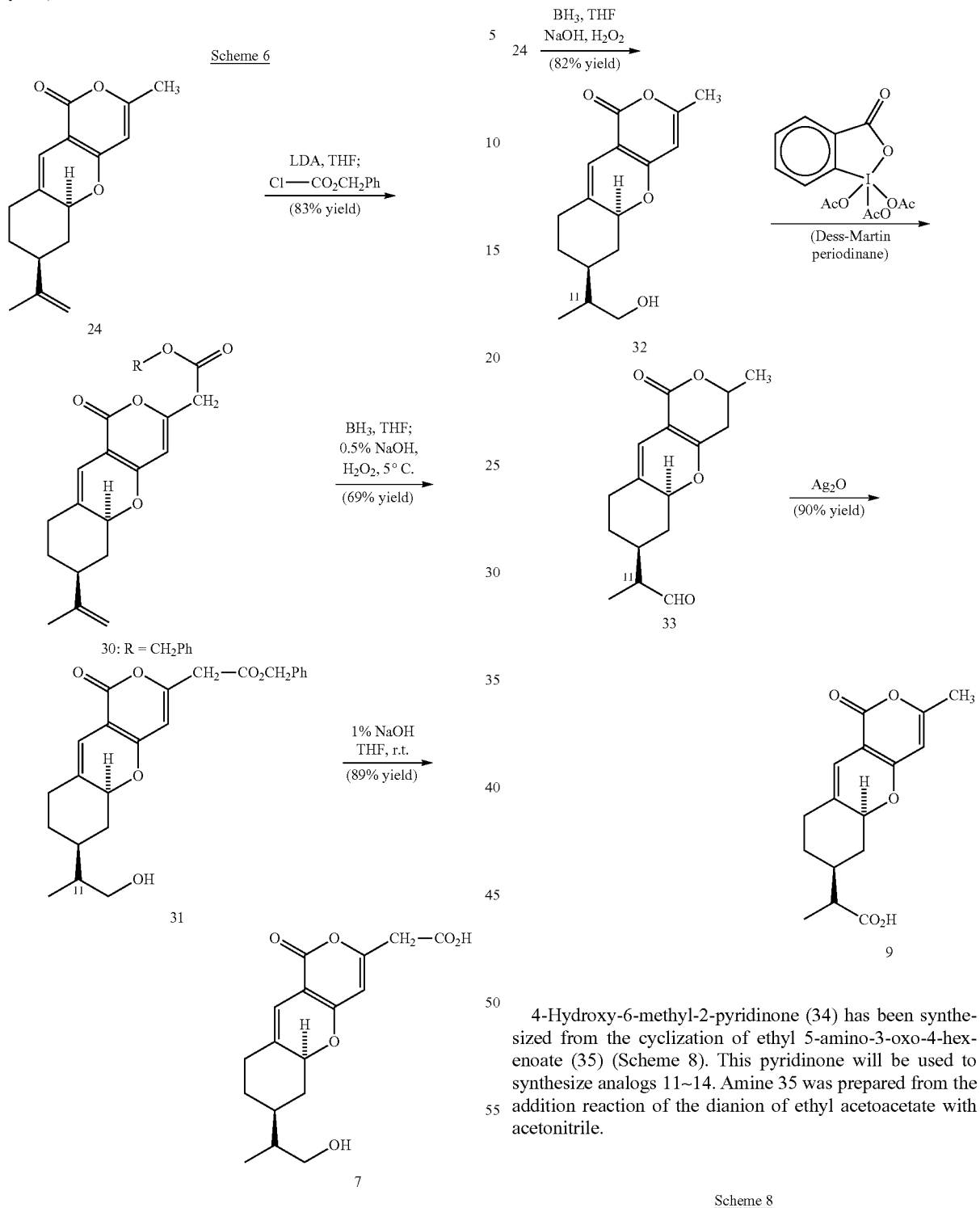

Carboxylic acid 9 has been synthesized by the selective hydroboration of tricyclic pyrone 24 with 1 equiv of borane in THF followed by 0.1% NaOH and 30% $H_2O_2$ (82% yield) to give alcohol 32. This alcohol was subjected to oxidation with the Dess-Martin periodinane reagent in methylene chloride to produce aldehyde 33 and was then oxidized further with silver oxide to give carboxylic acid 9 (Scheme 7).

4-Hydroxy-6-methyl-2-pyridinone (34) has been synthesized from the cyclization of ethyl 5-amino-3-oxo-4-hexenoate (35) (Scheme 8). This pyridinone will be used to synthesize analogs 11~14. Amine 35 was prepared from the addition reaction of the dianion of ethyl acetoacetate with acetonitrile.

Scheme 8

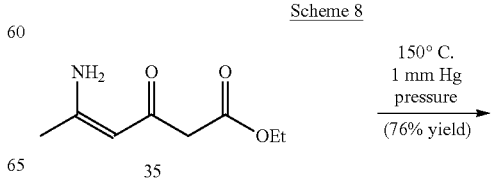

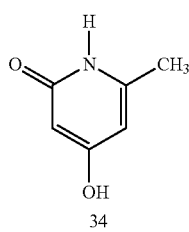

34 (19%)

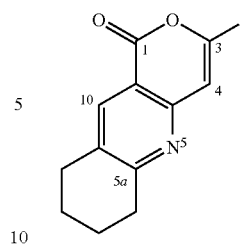

35 (48%)

Other nitrogen analogs of tricyclic pyrone 23 such as 34 and 35 were also prepared. These pyrones can be converted into the corresponding C-3 acetic acids by a similar method as that for the formation of compound 1. Hence, condensation of 4-amino-6-methylpyrone (39) (Cervera, M.; Moreno-Manas, M.; Pleixats, R. *Tetrahedron* 1990, 46, 7885-7892) with aldehyde 21 and (S)-10-camphorsulfonic acid in toluene at 85° C. gave tricyclic pyrone 34 and pyranoisoquinoline 35 (Scheme 9). Amino pyrone 39 was prepared by following the reported procedure in Cervera, M.; Moreno-Manas, M.; Pleixats, R. *Tetrahedron* 1990, 46, 7885-7892.

Similarly, analogs that modified the C-7 side chain such as compounds 41~43 were also made (Scheme 10). Mesylation of alcohol 32 with methanesulfonyl chloride and triethylamine in methylene chloride gave a 78% yield of mesylate 40. Displacement of 40 with sodium salt of adenine or 3-deazaadenine or potassium phthalimide gave good yields of adenine analog 41, 3-deazaadenine analog 42, and phthalimide analog 43, respectively.

Scheme 9

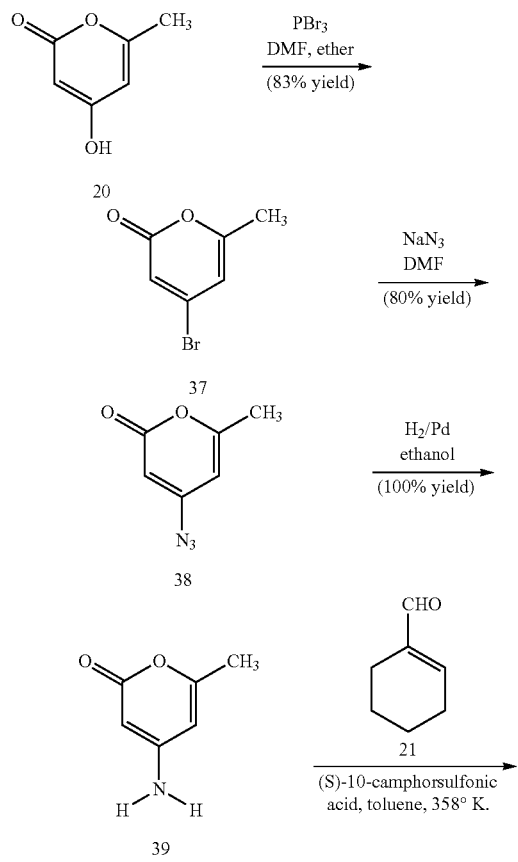

Scheme 10

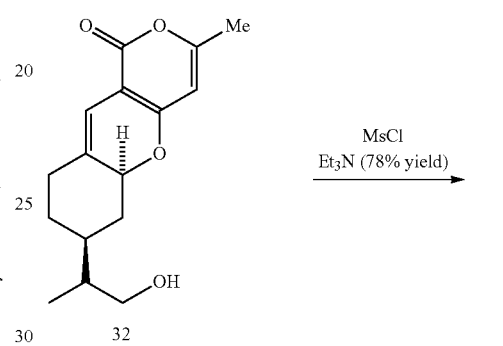

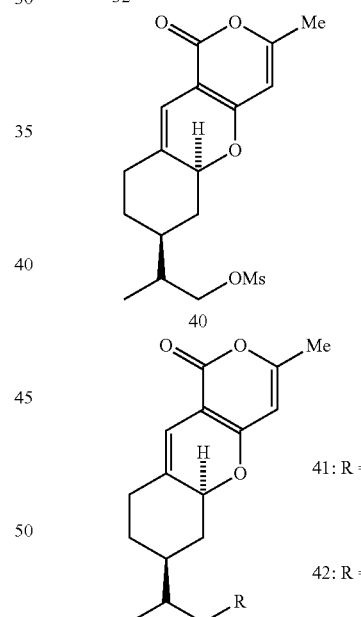

41: R = 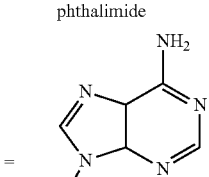

42: R = 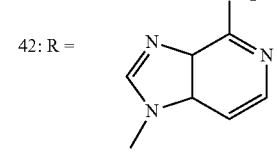

43: R = 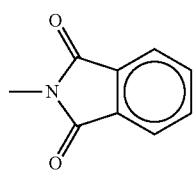

Several tricyclic pyranopyrones containing various functionalities (Scheme 12) were synthesized. A common intermediate, compound 108 (an optically pure compound) (Hua, D. H.; Chen, Y.; Sin, H.-S.; Maroto, M. J.; Robinson, P. D.; Newell, S. W.; Perchellet, E. M.; Ladesich, J. B.; Freeman, J. A.; Perchellet, J.-P.; Chiang, P. K. J. Org. Chem. 1997, 62, 6888-6896; Jin, L.-W.; Hua, D. H.; Shie, F.-S.; Maezawa, I.; Sopher, B.; Martin, G. M. J. Mol. Neurosci. 2002, 19, 57-61), was used in the synthesis of 101, 112 (Schemes 12 and 13) by selective functionalizations of C3 and C7 side chains. A regioselective deprotonation of the C3 methyl group of TP 108 can be carried out with a strong base such as lithium diisopropylamide (LDA) or n-BuLi. Hence, treatment of 108 with LDA followed by benzyl chloroformate gave a 46% yield (based on reacted 108) of 101 with 37% recovery of 108 (Scheme 12). Apparently, the anion of 108 deprotonates α-CH of the benzyl ester function of product 101 to give 108 and anion of 101. However, in the reaction with carbon dioxide (vide infra), this deprotonation by the anion of 108 is precluded by its faster reaction with the carbon dioxide. Chemo-selective hydroboration of 101 with 1 equiv. of $BH_3$·THF at –25° C. for 14 h followed by oxidation with 0.5% NaOH/30% $H_2O_2$ at 0° C. gave a 69% yield (based on reacted 101) of alcohols 102 along with 26% recovery of 101. The less hindered C13 double bond was selectively reacted in the presence of C9a double bond. Based on the $^{13}$C NMR spectrum of 102, two diastereomers at C13 were formed in a ratio of 1:1 and were inseparable by silica gel column chromatography and HPLC (normal phase; 102, 103, 105, and 106). Hence, mixtures of these diastereomers were used for biological evaluation. A dihydroxylation was resulted when the hydroboration reaction was carried out at 0° C. Yields of 32% of 103 and 14% of 102 were isolated. Again, column chromatography afforded only an inseparable mixture of two C13 diastereomers, 103. No other stereoisomers at C9a and C10 of 103 were detected. The C9a,10 stereochemistry of 103 was tentatively assigned assuming that borane approaches the C9a-C10 double bond of 102 from the less hindered a face (same side as C5a-H). Amide 104 was synthesized in 90% overall yield from pyrone 108 by (1) treatment with LDA in THF followed by carboxylation with carbon dioxide to give acid 109 (92% yield), and (2) coupling of 109 with amine 110 in a solution of N,N'-dicyclohexylcarbodiimide (DCC) in dichloromethane followed by basic hydrolysis with aqueous NaOH. Amine 110 was prepared in 85% overall yield from the coupling of N-(t-butyloxycarbonyl)-L-aspartic acid 4-benzyl ester (111) with p-nitroaniline in a solution of DCC in dichloromethane followed by acidic hydrolysis of the t-butoxycarbonyl protecting group with HCl.

Scheme 12

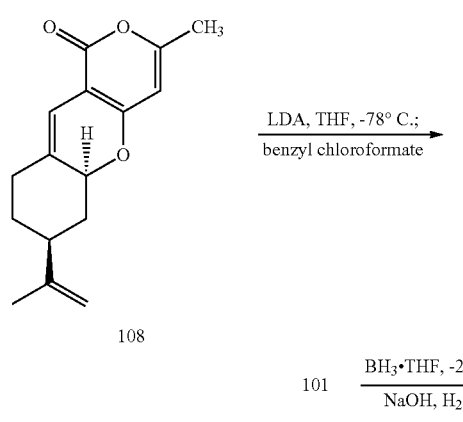

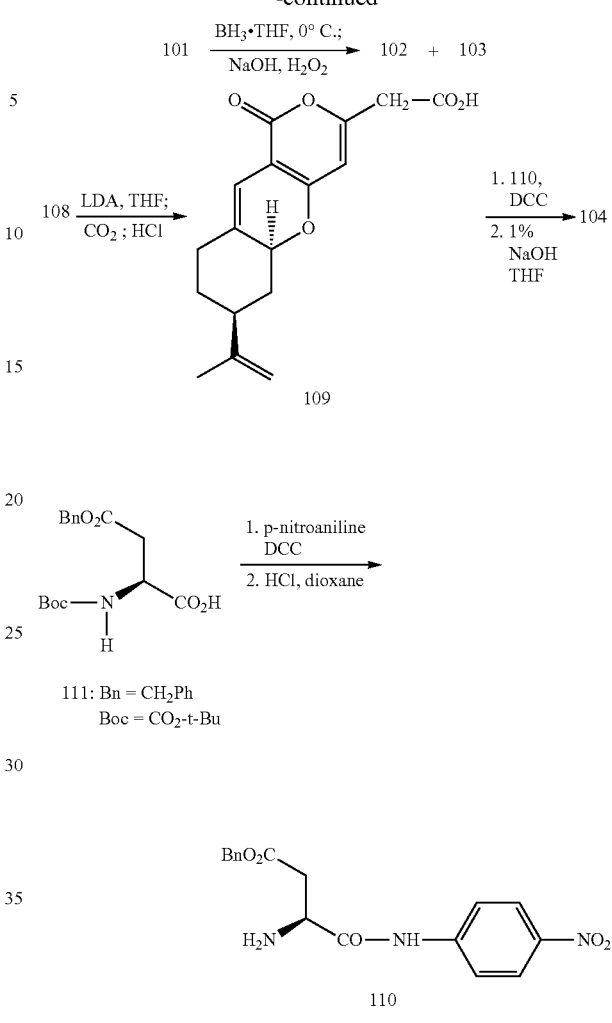

Since the isopropenyl group of TPs can be selectively hydroxylated (vide supra), functional group transformation of the resulting hydroxyl group provides a number of TP analogs. Hence, treatment of 108 with 1 equiv. of $BH_3$·THF at –25° C. followed by oxidation with NaOH and H2O2 gave an 82% yield (based on reacted 108) of an inseparable mixture of two C-12 diastereomers, 112, and a 26% recovery of 108 (Scheme 13). $^{13}$C NMR spectrum of 112 revealed the two diastereomers to be present in equal amounts. Mesylation of 112 with triethylamine and methanesulfonyl chloride gave mesylate 113 in a 94% yield. Treatment of mesylate 113 with adenine and sodium hydride in DMF at 80° C. for 20 h produced 105 and 106 in a ratio of 4:1. Compounds 105 and 106 were separated by silica gel column chromatography. The corresponding N7'-analog was not detected under these reaction conditions. The regiochemistry of these two isomeric products was assigned based on the comparison of the $^1$H NMR resonances of C2'H and C8'H of the adenine moiety with the corresponding values reported (Barbuch, R.; Curran, T. T.; Hay, D. A.; Vaz, R. J. Tetrahedron 1997, 53, 7181-7190; Magnin, G. C.; Dauvergne, J.; Burger, A.; Biellman, J. F. Tetrahedron Lett. 1996, 37, 7833-7836). Moreover, 2D NOESY experiments showed a correlation between C8'-H (δ 7.78 ppm) and $CH_2N$ (δ 4.01 ppm) of 105 and between C8'-H (δ 7.98 ppm) and $CH_2N$ (δ 4.08 ppm) of 106.

49

Scheme 13

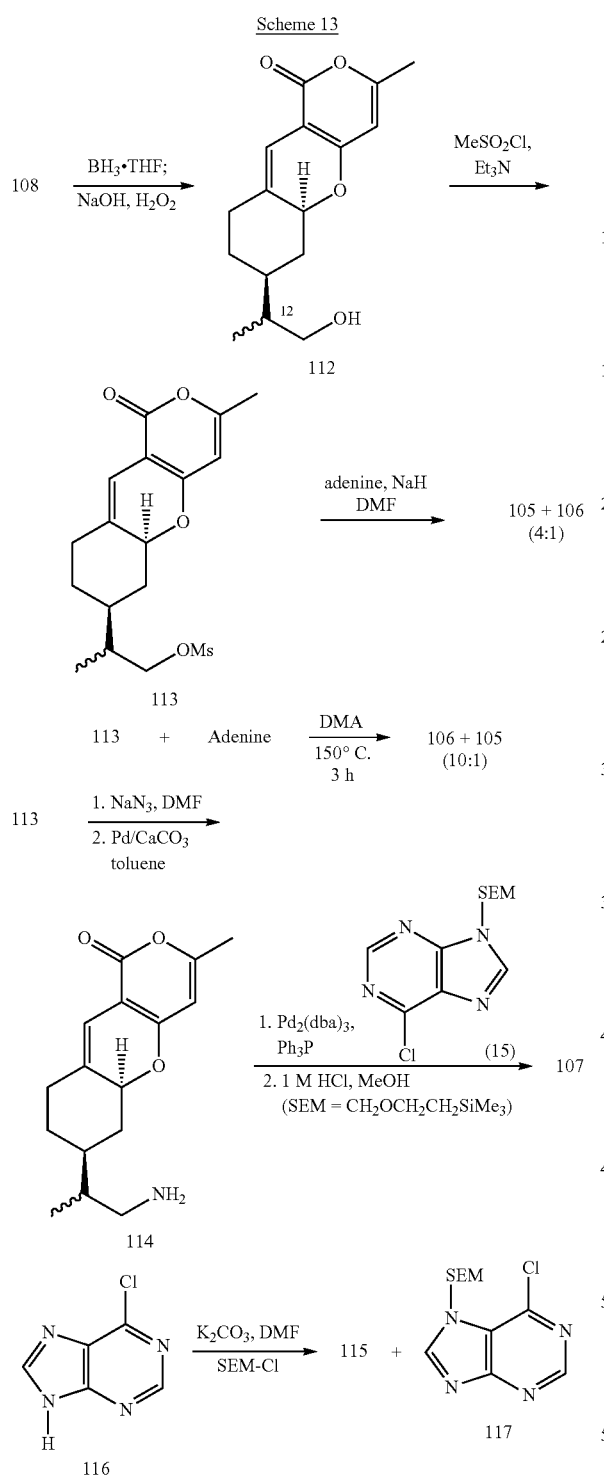

Initially, identification of the structure of 106 was difficult since it is a previously unreported compound, and reports in the literature do not mention N-3 alkylation under basic conditions (Borcherding, D. R.; Scholtz, S. A.; Borchardt, R. T. J. Org. Chem. 1987, 52, 5457-5461). To verify its structure, a different method to prepare it was sought, and an adenine-tricyclic pyrone isomer, 107, was also synthesized to compare the spectroscopic data and as well as the bioactivity data. A method has been reported for N3-alkylation of adenine (Le-

50 onard, N. J.; Fujii, T. J. Am. Chem. Soc. 1963, 85, 3719). Treatment of mesylate 113 with adenine in N,N-dimethylacetamide (DMA) at 150° C. without base provided compound 106 (43% yield) as the major product along with a small amount of 105 (4% yield).

The synthesis of N10'-adenine derivative 107 was achieved from a palladium-mediated displacement reaction of amine 114 with chloropurine (although compound 115 has been reported, spectral data is not available, moreover, the formation of N7-SEM derivative, the minor isomer, was not mentioned: Chida, N.; Suzuki, T.; Tanaka, S.; Yamada, I. Tetrahedron Lett. 1999, 40, 2573-2576; Gundersoen, L.; Bakkestuen, A. K.; Aasen, A. J.; Overas, H.; Rise, F. Tetrahedron 1994, 50, 9743-9756). Amine 114 was prepared from the displacement of mesylate 113 with sodium azide in DMF at 60° C. (83% yield) followed by hydrogenation with 10% Pd/CaCO₃ in toluene under 1 atm of hydrogen at 25° C. (78% yield). N-10' Adenine derivative 107 was synthesized via palladium-mediated displacement of 6-chloro-9[2-(trimethylsilyl) ethoxy] methyl-1H-purine (115) and amine 114 in the presence of 0.1 equiv. of Pd₂(dba)₃, 0.4 equiv. of triphenylphosphine and 1.5 equiv. of potassium carbonate in toluene under reflux (25% yield) followed by removal of the protecting group by treatment with 1 M HCl in methanol at 50° C. (100% yield). Purine 115 (61% yield) was prepared from the alkylation of 6-chloro-1H-purine (116) with potassium carbonate and 1-chloromethoxy-2-trimethylsilylethane (SEM-Cl) in DMF at 25° C., which also provided 6-chloro-7-[2-(trimethylsilyl) ethoxy]methyl-1H-purine (117; 14% yield). The regiochemistry of purine 115 and its C-7 isomer 117 were determined from 2D NOESY experiments in which their C8-H (δ 8.24 and 8.36 ppm, respectively) show correlation with their CH₂N (δ 5.62 and 5.80 ppm, respectively).

Schemes 14-17 show synthesis of additional compounds of the invention.

Scheme 14

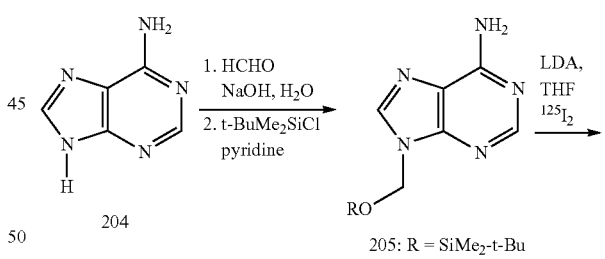

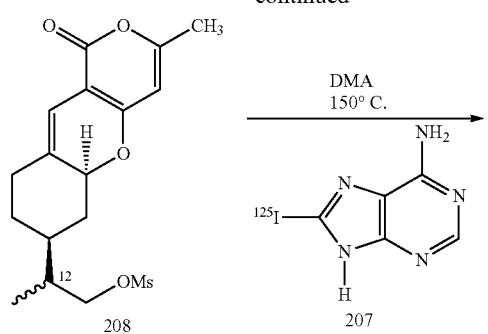
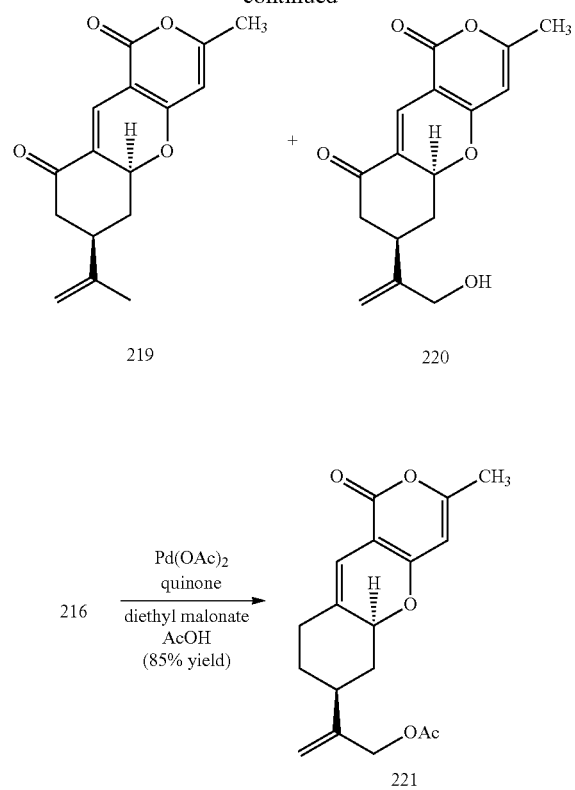
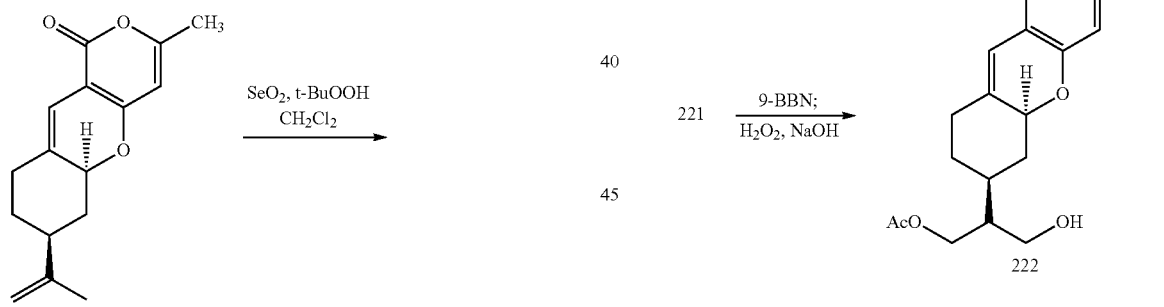
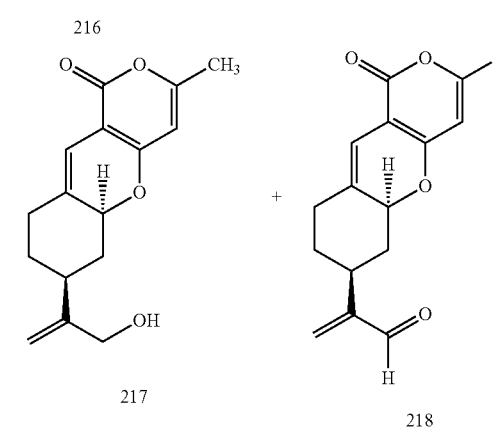
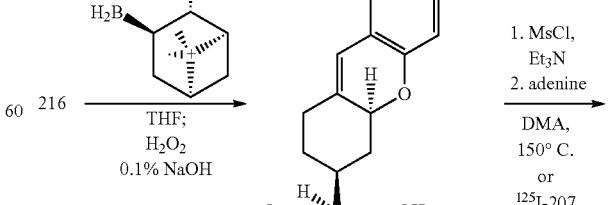

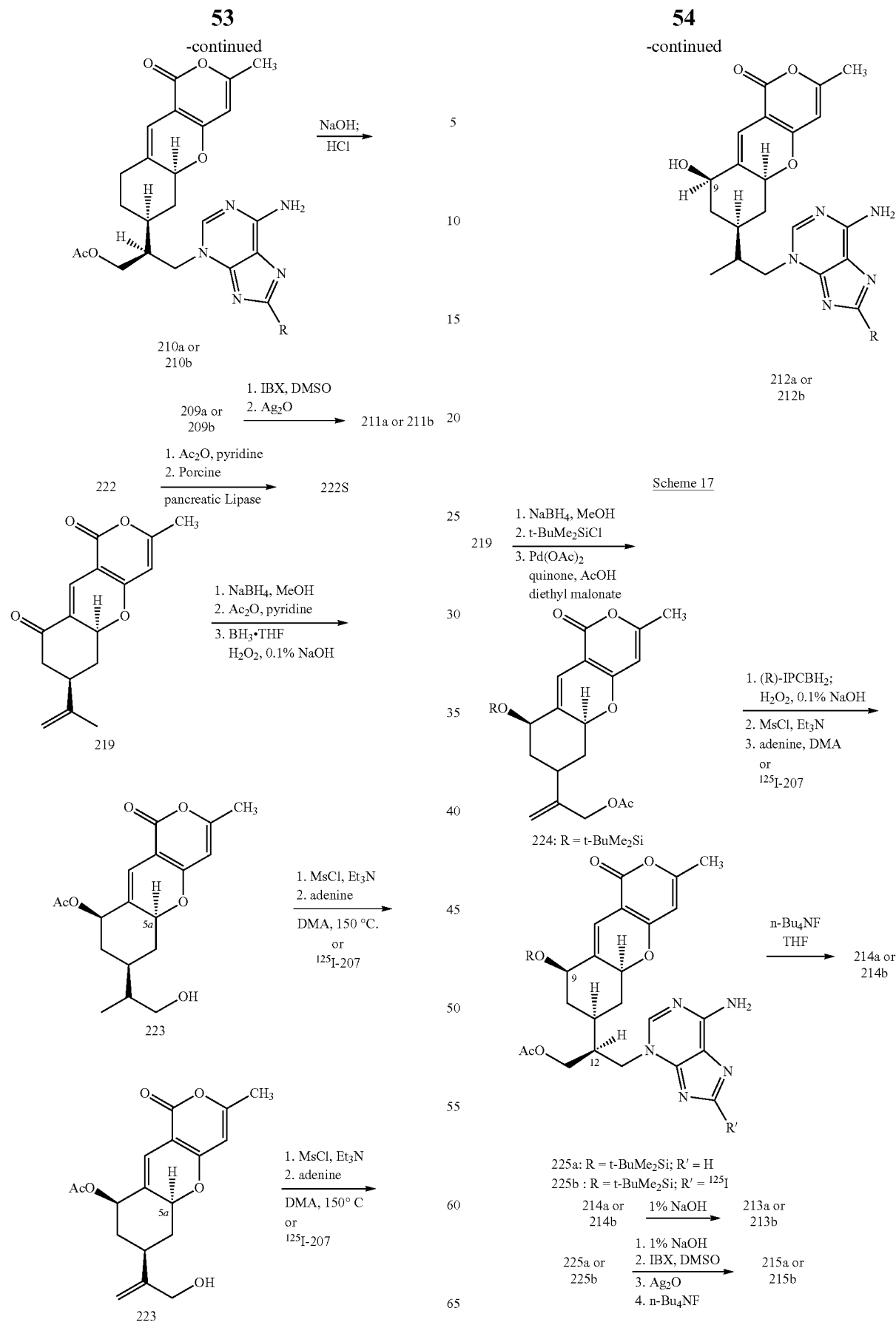

Experimental Section

General Methods. Nuclear magnetic resonance spectra were obtained at 400 MHz for $^1$H and 100 MHz $^{13}$C for in deuteriochloroform, unless otherwise indicated. Infrared spectra are reported in wavenumbers (cm$^{-1}$). Mass spectra were taken from a Hewlett Packard 5890 Series II, GC-HPLC-MS and a Bruker Esquire 3000 Plus electrospray ionization mass spectrometer. FAB spectra were taken by using Xe beam (8 KV) and m-nitrobenzyl alcohol as matrix. High-resolution Mass spectra were taken from an IonSpec HiResMALDI mass spectrometer using 2,5-dihydroxybenzoic acid as a matrix. Silica gel, grade 643 (200~425 mesh), was used for the flash chromatographic separation. THF and diethyl ether were distilled over sodium and benzophenone before used. Methylene chloride was distilled over CaH$_2$ and toluene and benzene were distilled over LiAlH$_4$. Ethyl acetate was dried over CaCl$_2$ and filtered and distilled under argon atmosphere. (5aS,7S)-{7-Isopropenyl-3-methyl-1H,7H-5a,6,8,9-tetrahydro-1-oxopyrano[4,3-b][1]benzopyran (108), an optically pure compound, was prepared as described (Hua, D. H.; Chen, Y.; Sin, H.-S.; Maroto, M. J.; Robinson, P. D.; Newell, S. W.; Perchellet, E. M.; Ladesich, J. B.; Freeman, J. A.; Perchellet, J.-P.; Chiang, P. K. J. Org. Chem. 1997, 62, 6888-6896). Pd$_2$(dba)$_3$ was prepared from palladium chloride, trans,trans-1,5-diphenyl-1,4-pentadien-3-one (dibenzylidene acetone), and sodium acetate in methanol (Ukai, T.; Kawazura, H.; Ishii, Y.; Bonnet, J. J.; Ibers, J. A. J. Organomet. Chem. 1974, 65, 253-266). N-(t-Butyloxycarbonyl)-L-aspartic acid 4-benzyl ester, adenine, 6-chloro-1H-purine, and 1-(chloromethoxy)-2-(trimethylsilyl)ethane (SEM-Cl) were purchased from Aldrich Chem. Co.

1. 3-Methyl-1H,7H-5a,6,8,9-tetrahydro-1-oxopyrano[4,3-b][1]-benzopyran (23)

A mixture of 100 mg (0.91 mmol) of 1-cyclohexenecarboxaldehyde (21), 115 mg (0.91 mmol) of 4-hydroxy-6-methyl-2-pyrone (20), and 52 mg (0.46 mmol) of L-proline in 5 mL of ethyl acetate was stirred at 70° C. under argon atmosphere for 24 h. The mixture was cooled to room temperature, diluted with 100 mL of methylene chloride, washed with saturated aqueous NaHCO$_3$ solution twice (30 mL each), with water (60 mL), and then with brine (60 mL), dried (MgSO$_4$), filtered, and concentrated to give 200 mg of crude product. Column chromatography on silica gel of the crude product using a gradient mixture of hexane and diethyl ether as eluant gave 0.150 g (76% yield; 80% based on recovered starting pyrone) of 23 and 6 mg (5% recovery) of 20. Compound 23: mp 110~112° C.; single crystal X-ray diffraction analysis was carried out on a single crystal obtained from the recrystallization from ether-hexane. IR (Nujol) v 1710 (s, C=O), 1630 (C=C), 1560. $^1$H NMR δ 6.07 (s, 1H, C10H), 5.7 (s, 1H, C4H), 5.02 (dd, J=11, 5 Hz, 1H, C5a H), 2.41 (m, 1H, C9H), 2.18 (s, 3H, Me), 2.13 (m, 1H, C5a H), 2.02~1.88 (m, 2H), 1.8~1.7 (m, 2H), 1.5~1.4 (m, 2H); $^{13}$C NMR δ 174 (s, C=O), 163.24 (s, C3), 161.38 (s, C4a), 133.06 (s, C10a), 109.17 (d, C10), 99.76 (d, C4), 97.33 (s, C9a), 79.69 (s, C5a), 35.15 (t, C9), 33.14 (t, C6), 26.89 (t, C7), 24.52 (t, C8), 20.06 (q, Me); MS (CI) m/z 219 (M+1). Analysis Calculated for C$_{13}$H$_{14}$O$_3$: C, 71.54; H, 6.47. Found: C, 71.39; H, 6.53.

2. (5aS, 7S)-7-Isopropenyl-3-methyl-1H,7H-5a,6,8,9-tetrahydro-1-oxopyrano-[4,3-b][1]benzopyran (24)

From 1.000 g (7.93 mmol) of pyrone 20 and 1.191 g (7.93 mmol) of S-perilaldehyde (22), 1.596 g (78% yield) of 24 was obtained after column chromatographic separation: yellow solid, mp 140~141° C.; [α]$^{22}_D$=+31.9° (c 0.75, CHCl$_3$); $^1$H NMR δ 6.1 (s, 1H, C10H), 5.72 (s, 1H, C4H), 5.1 (dd, J=11 Hz, 5 Hz, 1H, C5a H), 4.75 (m, 1H, =CH), 4.73 (m, 1H, =CH), 2.48 (ddd, J=14 Hz, 4 Hz, 2.4 Hz, 1H), 2.22-2.02 (series of m, 3H), 2.19 (s 3H, C4-Me), 1.88-1.72 (series of m, 2H), 1.74 (s, 3H, MeC=), 1.31 (ddd, J=25 Hz, 12.8 Hz, 4 Hz, 1H); $^{13}$C NMR δ 163.4 (s, C=O), 162.6 (s, C3), 161.7 (s, C4a), 147.9 (s, C10a), 132.3 (s, =C), 109.8 (d, C10), 109.6 (t, =CH$_2$), 99.9 (d, C4), 97.5 (s, C9a), 79.4 (s, C5a), 43.6 (d, C7), 40.0 (t), 32.5 (t), 32.1 (t), 20.9 (q, Me), 20.3 (q, Me); MS FAB, m/z 259 (M+1, 70%), 258, 257, 215, 189, 139 (100). Anal. Calcd for C$_{16}$H$_{18}$O$_3$: C, 74.4; H, 7.02. Found: C, 74.17; H, 7.33.

3. 3-Methoxycarbonylmethyl-1H,7H-5a,6,8,9-tetrahydro-1-oxopyrano[4,3-b][1]-benzopyran To a cold (−10° C.) solution of 0.31 mL (2.20 mmol) of diisopropylamine in 10 mL of diethyl ether under argon was added 1.40 mL (2.20 mmol; 1.6 M solution in hexanes) of n-butyllithium via syringe and the solution was stirred for 1 hour. In another flask, 0.400 g (1.83 mmol) of 23 in 10 mL THF under argon atmosphere was prepared and cooled to −78° C. The freshly prepared LDA was added to the above pyrone solution via cannula, and then, 0.32 mL (1.83 mmol) of HMPA was added via syringe. The solution was allowed to react at −78° C. for 3 hours. Finally, 0.14 mL (1.83 mmol) of methyl chloroformate was added to the resulting anion solution at −78° C., stirred at this temperature for 2 hours, then diluted with 30 mL of distilled water, and extracted with diethyl ether (50 mL×3). The combined ether was washed with brine (50 mL, dried over MgSO$_4$, concentrated, and column chromatographed on silica gel using a gradient mixture of hexane and ether as eluent to give 0.215 g (72% yield based on recovered starting material 23) of the title compound and 0.165 g (40% recovery) of 23. $^1$H NMR 86.09 (s, 1H, C4H), 6.05 (s, 1H, C10H), 5.07 (dd, J=11.2 Hz, 5.6 Hz, 1H, C5a H), 3.80 (s, 5H, OMe and CH$_2$—CO), 2.44 (m, 1H, C9H), 2.14 (dd, J=12.0 Hz, 3.6 Hz, 1H), 2.03~1.72 (m, 4H), 1.55~1.31 (m, 2H); $^{13}$C NMR δ 165.2 (s, C=O), 162.3 (s, C=O), 161.4 (s, C3), 153.8 (s, C4a), 134.7 (s, C10a), 108.9 (d, C4), 102.6 (d, C10), 99.5 (s, C9a), 80.1 (d, C5a), 56.0 (q, OMe), 53.6 (t), 35.3 (t), 33.3 (t), 26.9 (t), 24.5 (t).

4. {1H,7H-5a,6,8,9-Tetrahydro-1-oxopyrano[4,3-b][1]benzopyran-3-yl}acetic acid (1)

To a cold (−10° C.) solution of 1.67 mL (12.0 mmol) of diisopropylamine in 20 mL of diethyl ether under argon was added 7.50 mL (12.00 mmol; 1.6 M solution in hexanes) of n-butyllithium via syringe and the solution was stirred for 1 hour at this temperature. In another flask, 1.300 g (6.00 mmol) of pyrone 23 in 20 mL THF under argon atmosphere was prepared and cooled to −78° C. The freshly prepared LDA was added to the above pyrone solution via cannula. The solution was allowed to react at −78° C. for 2 hours. Carbon dioxide was then flushed through the reaction solution via a balloon of CO$_2$ while the reaction flask was inserted with a needle to release the gas. The color of the blue anion soon changed to brownish color. The reaction mixture was stirred for 30 minutes, quenched with 20 mL saturated aqueous NaHCO$_3$, and 20 mL distilled water, and extracted with diethyl ether (30 mL×3). The aqueous layer was acidified with 6 N HCl, and extracted with methylene chloride (50 mL×3). The combined methylene chloride was washed with 50 mL water, 50 mL brine, dried over MgSO$_4$, and concentrated to give 1.480 g pure product. $^1$H NMR δ 6.15 (s, 1H, C4H), 5.92 (s, 1H, C10H), 5.16 (dd, J=10.8 Hz, 4.8 Hz, 1H, C5a H), 3.53 (s, 2H, CH$_2$—CO), 2.41 (d, J=14.4, 1 H), 2.10~1.96 (m, 2H), 1.83~1.63 (m, 3H), 1.46 (m, 1H), 1.29~1.23 (m, 1H); $^{13}$C NMR (DMSO-d6) δ 169.4 (s, enol =COH), 162.4 (s, C=O), 160.9 (s, C3), 158.2 (s, C4a), 134.4 (s, C10a), 108.2 (d, C10), 100.8 (d, C4), 99.3 (s, C9a), 79.1 (d, C5a), 97.2 (d, enol C=), 34.8 (t, CH$_2$), 32.4 (t, CH$_2$), 26.5 (t, CH$_2$), 23.9 (t, CH$_2$).

Compound 1 was also prepared from the basic hydrolysis of 3-(methoxycarbonylmethyl)-1H,7H-5a,6,8,9-tetrahydro-1-oxopyrano[4,3-b][1]-benzopyran. To a solution of 0.80 g (0.29 mmol) of 3-(methoxycarbonylmethyl)-1H,7H-5a,6,8, 9-tetrahydro-1-oxopyrano[4,3-b][1]-benzopyran in a solution of 4 mL of THF and water (1:3) was added 0.033 g (0.58 mmol) of KOH at room temperature. The mixture was heated to 40° C. for 14 h. It was cooled to room temperature, 30 mL of distilled water was then added, and was extracted three times with methylene chloride (40 mL each). The combined methylene chloride layer was washed with 30 mL of distilled water, and 30 mL of brine, and concentrated to give 0.021 g of starting material (26% recovery). The aqueous layer was acidified with 10 mL of 1 N HCl solution and extracted three times with methylene chloride (50 mL each). The combined organic layer was washed twice with distilled water (40 mL each), 40 mL of brine, dried over MgSO$_4$, concentrated to give 0.33 g of 1 (58% yield, based on recovered starting material).

5. {(5aS,7S)-7-Isopropenyl-1H,7H-5a,6,8,9-tetrahydro-1-oxopyrano[4,3-b][1]-benzopyran-3-yl}acetic acid (6)

To a cold (−10° C.) solution of 0.27 mL (1.90 mmol) of diisopropylamine in 5 mL of diethyl ether under argon was added 1.20 mL (1.90 mmol; 1.6 M solution in hexanes) of n-butyllithium via syringe and the solution was stirred for 1 hour at this temperature. In another flask, 0.250 g (0.97 mmol) of 24 in 5 mL THF under argon atmosphere was prepared and cooled to −78° C. The freshly prepared LDA was added to the above solution via cannula. The solution was allowed to react at −78° C. for 2 hours. Carbon dioxide was then flushed into the solution through a balloon and insertion of a needle to allow the gas to flush out from the reaction mixture. The color of the blue anion soon changed to brownish color. The reaction mixture was stirred for 30 minutes, quenched with 10 mL saturated aqueous NaHCO$_3$, and 10 mL distilled water, and extracted with ether (15 mL×3). The aqueous layer was acidified with 6 N HCl and extracted with methylene chloride (30 mL×3). The combined methylene chloride was washed with 30 mL water, and 30 mL brine, dried over MgSO$_4$, and concentrated to give 0.271 g pure product. $^1$H NMR δ 6.09 (s, 1H, C4H), 5.95 (s, 1H, C10H), 5.14 (dd, J=11.2, 4.8 Hz, 1H, C5aH), 4.76 (s, =CH), 4.73 (s, =CH), 3.51 (s, 2H, CH$_2$), 2.50 (d, J=14 Hz, 1H), 2.22~2.02 (a series of m, 3H), 1.88~1.74 (m, 2H), 1.75 (s, 3H, Me), 1.31 (m, 1H).

This acid was also prepared from the basic hydrolysis of benzyl ester 30.

To a 0.122 g (0.31 mmol) of benzyl ester 30 in 4 mL THF solution was added 1.5 mL of 1% NaOH aqueous solution at room temperature. The reaction mixture was stirred at room temperature for 2 hours, and acidified with 0.1 mL of 4 N HCl in dioxane. The solvent was removed via vacuum, the residue was then dissolved in 20 mL methylene chloride and filtered. The filtrate was then concentrated and column chromatographed to give 0.093 g of 6 (100% yield).

6. 2-{1H,7H-5a,6,8,9-Tetrahydro-1-oxopyrano[4,3-b][1]benzopyran-7-yl}-propanal (33)

A solution of 0.070 g (0.25 mmol) of 32 and 0.160 g (0.38 mmol) of Dess Martin periodinane in 4 mL of methylene chloride was stirred at room temperature for 48 hours. The reaction mixture was filtered through Celite, and the filter cake was washed with 50 mL methylene chloride. The organic layer was concentrated and column chromatographed on silica gel using a gradient mixture of hexane and ether as eluent to give 0.060 g of 33 (87% yield). $^1$H NMR δ 9.67 (d, J=0.4 Hz, 1H, CHO), 6.09 (s, 1H, C10H), 5.71 (s, 1H, C4H), 5.10 (m, 1H, C5a H), 2.50~2.46 (m, 1H), 2.36~2.31 (m, 1H), 2.19 (s, 3H, Me), 2.17~2.01 (m, 2H), 1.79~1.57 (m, 3H), 1.30~1.17 (m, 1H), 1.11 (d, J=7.2 Hz, 3H, Me); $^{13}$C NMR δ 204.1 (d, CHO), 163.3 (s, C=O), 162.5 (s, C3), 161.8 (s, C4a), 131.7 (s, C 10a), 109.8 (d, C4), 99.8 (d, C10), 97.4 (s, C9a), 79.0 (d, C5a), 50.7 (d), 39.2 (d), 37.3 (t), 36.3 (t), 32.1 (t), 20.2 (q, Me), 10.1 (q, Me).

7. n-Butyl 2-hydroxy-3-{1H,7H-5a,6,8,9-tetrahydro-1-oxopyrano[4,3-b][1]benzo-pyran-3-yl}-propanoate (25)

To a cold (−10° C.) solution of 0.13 mL (0.92 mmol) of diisopropylamine in 5 mL of diethyl ether under argon was added 0.56 mL (0.92 mmol; 1.6 M solution in hexanes) of n-butyllithium via syringe, and the solution was stirred for 1 hour. In another flask, a solution of 0.100 g (0.46 mmol) of 23 in 5 mL of THF under argon was cooled to −78° C. The freshly prepared LDA solution was added to the above solution at −78° C. via cannula, then, 0.08 mL (0.46 mmol) of HMPA was added to the reaction mixture via syringe and stirred at −78° C. for 3 hours. To the reaction solution, a solution of 0.060 g (0.46 mmol) of n-butyl glyoxalate in 3 mL THF was subsequently added to the anion solution at −78° C. via cannula, and stirred for 1 hour at this temperature. The solution was diluted with 20 mL of distilled water, and extracted three times with ethyl ether (50 mL each). The combined organic layer was washed with 30 mL of distilled water, 30 mL of brine, dried over MgSO$_4$, concentrated, and column chromatographed over silica gel to give 0.132 g of 1.112 (86% yield). $^1$H NMR δ 6.03 (s, 1H, C10H), 5.87 (s, 1H, C4H), 5.03 (m, 1H, C5a), 4.53 (t, J=4 Hz, 1H, CH—OH), 4.22~4.18 (m, 2H, OCH$_2$), 2.94 (d, J=14.8 Hz, 1H, CH$_2$CHOH), 2.75 (dd, J=14.8 Hz, 8 Hz, 1H, CH$_2$CHOH), 2.41 (d, J=14 Hz, 1H), 2.12 (d, J=8 Hz, 1H), 2.02~1.28 (m, 12H), 0.94 (t, J=7.2 Hz, 3H, Me); $^{13}$C NMR δ 173.5 (s, C=O), 162.9 (s, C1), 162.2 (s, C3), 159.7 (C4a), 133.6 (s, C10a), 109.0 (d, C4), 101.7 (d, C10), 98.2 (s, C9a), 79.7 (d, C5a), 67.9 (t, CHOH), 65.9 (d, CH$_2$O), (38.8 (t), 35.2 (t), 33.2 (t), 30.5 (t), 26.9 (t), 24.5 (t), 19.0 (t), 13.6 (q, Me).

8. 2-Hydroxy-3-{1H,7H-5a,6,8,9-tetrahydro-1-oxopyrano[4,3-b][1]benzopyran-3-yl}-propanoic acid (3)

To 0.030 g (0.09 mmol) of 25 in 2 mL THF was added 0.5 mL of 1% aqueous NaOH solution at room temperature. The reaction mixture was stirred for 1 hour, diluted with 20 mL of distilled water, acidified with a few drops of 1 N HCl solution, extracted three times with methylene chloride (40 mL each). The combined organic layer was washed with 20 mL brine, dried over MgSO$_4$, concentrated to give 0.018 g of 3 (72% yield). $^1$H NMR δ 6.01 (s, 1H, C10 H), 5.92 (s, 1H, C4H), 5.05 (dd, J=11.2 Hz, 4.8 Hz, 1H, C5a H), 4.58 (dd, J=7.2 Hz, 4 Hz, 1H, CH—OH), 3.02 (dd, J=14.8 Hz, 4 Hz, 1H, C H₂—CHOH), 2.85 (dd, J=14.8 Hz, 7.2 Hz, 1H, CH₂—CHOH), 2.41 (d, J=14 Hz, 1H), 2.13 (m, 1H), 2.01~1.70 (m, 4H), 1.48~1.22 (m, 2H).

9. n-Butyl 2-Hydroxy-3-{1H,7H-5a,6,8,9,10,11-hexahydro-10-hydroxy-1-oxo-pyrano[4,3-b][1]-benzopyran-3-yl}-propanoate (25A)

A solution of 0.100 g (0.29 mmol) of 1.112 and 0.57 mL (0.57 mmol) of BH₃.THF (1.0 M in THF) in 5 mL THF was stirred under argon at 0° C. for 2 hours. The reaction solution was warmed to room temperature and stirred for overnight. Subsequently, 2 mL of 1% aqueous of NaOH and 3 mL of 30% hydrogen peroxide was added, stirred at room temperature for 4 hours, diluted with 30 mL of distilled water, and extracted four times with methylene chloride (40 mL each). The combined organic layer was washed with 20 mL brine, dried over MgSO₄, and concentrated to give 0.033 g of 25A (32% yield). Compound 25A: $^1$H NMR δ 5.97 (s, 1H, C4H), 4.54 (s, 1H, C5a), 4.42 (s, 1H, C10H), 4.37 (s, 1H, CH—OH), 2.99 (dd, J=10.8 Hz, 4 Hz, 1H, CH₂—CHOH), 2.76 (dd, J=8.4 Hz, 6.4 Hz, 1H, CH₂—CHOH), 2.17~1.22 (m, 14H), 0.95 (t, J=7.2 Hz, 3H, Me).

10. 2-Hydroxy-3-{1H,7H-5a,6,8,9,10,11-hexahydro-10-hydroxy-1-oxopyrano[4,3-b][1]benzopyran-3-yl}-propanoic acid (2)

A solution of 0.026 g (0.07 mmol) of 25A and 1.5 mL of 1% aqueous NaOH solution in 2 mL THF was stirred at room temperature for 1 hour. The reaction mixture was then acidified with a few drops of 1 N HCl solution. The solvent was removed using rotary evaporator. The residue was dissolved in 10 mL of ethanol, and filtered through a 1 inch long of silica gel packed in a pipette column. The filtrate was concentrated to give 0.016 g of 2 (73% yield). $^1$H NMR δ 6.19 (s, 1H, C4H), 4.63 (dd, J=7.6 Hz, 4.8 Hz, 1H, C5a H), 4.46 (m, 1H, CH—OH), 3.07 (dd, J=15.2 Hz, 4 Hz, 1H), 2.93 (m, 2H), 2.24~1.25 (m, 8H).

11. n-Butyl 2-(Methanesulfonyloxy)-3-{1H,7H-5a,6,8,9-tetrahydro-1-oxopyrano[4,3-b][1]benzopyran-3-yl}-propanoate (25B)

A solution of 0.200 g (0.29 mmol) of 25, 0.24 mL (0.87 mmol) of triethylamine, and 0.06 mL (0.87 mmol) of methanesulfonyl chloride in 5 mL methylene chloride was stirred at 0° C. for 1 hour, and at room temperature for 2 hours. The reaction mixture was diluted with 30 mL of saturated aqueous NaHCO₃, and extracted three times with methylene chloride (30 mL each). The combined organic layer was washed with 30 mL of distilled water, 30 mL brine, dried over MgSO₄, concentrated, and purified through silica gel column chromatography to give 0.193 g of 25B (90% yield, based on recovered starting material 25) and 0.240 g of 25 (13% recovery). Compound 1.116: $^1$H NMR δ 6.01 (s, 1H, C4H), 5.88 (s, 1H, C10H), 5.31 (dd, J=8.4 Hz, 4.4 Hz, 1H, CH-OMs), 5.07 (d, J=8 Hz, 1H C5a), 4.26~4.21 (m, 2H, OCH₂), 3.12 (s, 3H, Me), 3.09~2.96 (m, 2H, CH₂—COMs), 2.42 (d, J=14.0 Hz, 1H), 2.16~1.28 (m, 11H), 0.94 (t, J=7.2 Hz, 3H, Me); $^{13}$C NMR δ 167.6 (s, C=O), 162.4 (s, C1), 161.4 (s, C3), 156.9 (s, C4a), 134.2 (s, C10a), 108.7 (d, C4), 102.2 (s, C9a), 98.5 (d, C10), 79.8 (d, C5a), 74.3 (d, CH-OMs), 66.3 (t, OCH2), 38.8 (t), 36.3 (t), 35.1 (t), 35.0 (t, stereoisomer), 33.1 (t), 31.6 (t, stereoisomer), 30.2 (t), 26.7 (t), 24.3 (t), 18.9 (q), 13.5 (q, Me).

12. n-Butyl 3-{1H,7H-5a,6,8,9-tetrahydro-1-oxopyrano[4,3-b][1]benzopyran-3-yl}-acrylate (28)

The solution of 0.072 g (0.17 mmol) of 25B and 0.07 mL (0.50 mmol) of DBU in 5 mL of toluene under argon was stirred at room temperature for 10 minutes. The reaction mixture was diluted with 30 mL of distilled water, and extracted three times with diethyl ether (50 mL each). The combined ether layer was washed with 30 mL of brine, dried over MgSO₄, and concentrated to give 0.054 g of 28 (100% yield). Compound 28: $^1$H NMR δ 7.04 (d, J=15.6 Hz, 1H, CH=), 6.66 (d, J=15.6 Hz, 1H, =CH), 6.11 (s, 1H, C4H), 6.06 (s, 1H, C10H), 5.09 (dd, J=11.2 Hz, 4.8 Hz, 1H, C5a H), 4.19 (t, J=6.8 Hz, 2H, OCH₂), 2.45 (d, J=14 Hz, 1H), 2.18~1.25 (m, 11H), 0.94 (t, J=4.8 Hz, 3H, Me); $^{13}$C NMR δ 166.2 (s, C=O), 161.6 (s, C1), 160.8 (s, C3), 154.8 (d, CH=), 136.1 (s, C4a), 123.7 (d, =CH), 109.5 (d, C4), 105.7 (d, C10), 102.2 (s, C9a), 80.2 (d, C5a), 65.0 (t, OCH₂), 35.4 (t), 33.5 (t), 30.8 (t), 27.0 (t), 24.6 (t), 19.3 (t), 13.8 (q, Me).

13. 3-{1H,7H-5a,6,8,9-Tetrahydro-1-oxopyrano[4,3-b][1]benzopyran-3-yl}-propenoic acid (5)

A solution of 0.014 g (0.04 mmol) of 28 and 1 mL of 1% aqueous NaOH solution in 2 mL of THF at room temperature was stirred at room temperature for 12 h. The reaction mixture was subsequently acidified with a few drops of 1 N HCl, diluted with 15 mL of distilled water, and extracted three times with methylene chloride (30 mL each). The combined organic layer was washed with 20 mL of brine, dried over MgSO₄, concentrated, and purified through silica gel column chromatography to give 0.120 g of 5 (100% yield). Compound 5: $^1$H NMR δ 7.19 (d, J=15.6 Hz, 1H, CH), 6.48 (d, J=15.6 Hz, 1H=CH), 6.45 (s, 1H, C4H), 6.02 (s, 1H, C10 H), 5.20 (dd, J=11.2 Hz, 4.8 Hz, 1H, C5a H), 2.12~1.28 (m, 8H).

14. n-Butyl 3-(N-Methylamino)-3-{1H,7H-5a,6,8,9-tetrahydro-1-oxopyrano[4,3-b][1]benzopyran-3-yl}-propanoate (28A)

A solution of 0.050 g (0.15 mmol) of 28 and 0.047 g (1.5 mmol) of methylamine in 2 mL of THF was stirred at 0° C. for 4 hours. The reaction mixture was then stirred at room temperature for 2 hours. The solvent was removed through rotary evaporation. The residue was purified through silica gel column chromatography to give 0.011 g of 28A (63% yield, based on recovered starting material 28), and 0.034 g of 28 (68% recovery). Compound 28A: $^1$H NMR δ 6.06 (s, 1H, C10H), 5.78 (s, 1H, C4H), 5.04 (d, J=5.2 Hz, 1H, C5a H), 4.14 (t, J=6.4 Hz, 2H, OCH₂), 3.59 (t, J=6.4 Hz, 1H, CH—N), 2.8 (s, 3H, MeN), 2.79~2.67 (m, 2H), 2.15~1.31 (m, 12H), 0.93 (t, J=7.6 Hz, 3H, Me).

15. 3-(N-Methylamino)-3-{1H,7H-5a,6,8,9-tetrahydro-1-oxopyrano[4,3-b][1]benzo-pyran-3-yl}-propanoic acid (29).

A solution of 0.013 g (0.04 mmol) of 28A and 1 mL of 1% aqueous NaOH solution in 2 mL THF was stirred at room temperature for 2 hours and neutralized with HCl. The solvents were then removed through rotary evaporation to give 0.006 g of 29 (55% yield). Compound 29: $^1$H NMR δ 6.17 (s, 1H, C4H), 5.95 (s, 1H, C10H), 5.22 (m, 1H, C5a H), 3.95 (m, 1H, CH—N), 3.20~3.17 (m, 2H), 2.80 (s, 3H, Me-N), 2.50~1.26 (m, 8H).

16. (5aS,7S)-3-(Benzyloxycarbonyl)methyl-7-isopropenyl-1H,7H-5a,6,8,9-tetrahydro-1-oxopyrano[4,3-b][1]benzopyran (30)

To a cold (−10° C.) solution of 0.43 mL (3.10 mmol) of diisopropylamine in 20 mL of diethyl ether under argon was added 3.00 mL (3.10 mmol; 1.6 M solution in hexanes) of n-Butyl Lithium via syringe and the solution was stirred for 1 hour. In another flask, 0.400 g (1.55 mmol) of 24 in 20 mL of THF under argon was cooled to −78° C. The freshly prepared LDA solution was added to the above solution at −78° C. via cannula, then, HMPA was added to the reaction mixture via syringe and stirred at −78° C. for 3 hours. To the reaction solution, 0.44 mL (3.1 mmol) of benzyl chloroformate in 20 mL THF was subsequently added to the anion solution at −78° C. via cannula, and stirred for 2 more hours at this temperature. The reaction was diluted with 40 mL of distilled water and extracted three times with methylene chloride (40 mL each). The combined organic layer was washed with 40 mL of brine, dried over $MgSO_4$, concentrated, and column chromatographed through silica gel using a gradient mixture of hexane and ether to give 0.140 g of 30 (95% yield based on recovered starting material 24) and 0.308 g (77% recovery) of 24. $^1$H NMR δ 7.38~7.31 (m, 5H, Ar), 6.08 (s, 1H, C4H), 5.91 (s, 1H, C10H), 5.28 (s, 2H, $CH_2OC$=O), 5.12 (dd, J=5.2 Hz, 1.2 Hz, 1H, C5aH), 4.75 (s, 1H, =$CH_2$), 4.72 (s, 1H, =$CH_2$), 3.50 (s, 2H, $CH_2C$=O), 2.49~2.45 (m, 1H), 2.21~2.01 (m, 3H), 1.86~1.70 (m, 2H), 1.73 (s, 3H, Me), 1.34~1.25 (m, 1H); $^{13}$C NMR δ 167.5 (s, C=O of ester), 162.6 (s, C=O), 161.9 (s, C3), 156.2 (s, C4a), 147.8 (s, C10a), 135.2 (s, Ar), 133.2 (s, C=), 128.7 (d, Ar), 128.6 (d, Ar), 128.4 (d, Ar), 109.8 (d, C10), 109.3 (t, =$CH_2$), 102.2 (d, C4), 98.8 (s, C9a), 79.5 (d, C5a), 67.5 (t, $OCH_2Ar$), 43.4 (t, $CH_2$), 39.9 (d, CH), 39.4 (t, $CH_2$), 32.4 (t, $CH_2$), 31.9 (t, $CH_2$), 20.8 (q, Me).

17. (5aS,7S)-3-(Benzyloxycarbonyl)methyl-7-(2-hydroxy-1-methyl)ethyl-1H,7H-5a,6,8,9-tetrahydro-1-oxopyrano[4,3-b][1]benzopyran (31)

A solution of 0.115 g (0.29 mmol) of 30 and 0.15 mL (0.15 mmol) of $BH_3$.THF complex (1.0 M in THF) in 5 mL THF was stirred for 1 h and then stored at −25° C. for overnight. The reaction mixture was allowed to warm up to 0° C., then, 2 mL of 0.5% NaOH aqueous solution and 2 mL of 30% hydrogen peroxide solution were added to the reaction mixture at 0° C., and stirred for 6 hours. The reaction mixture was then neutralized with a few drops of 6 N HCl, diluted with 30 mL of distilled water, and extracted three times with methylene chloride (30 mL each). The combined methylene chloride was washed with 30 mL brine, dried over $MgSO_4$, concentrated, separated through silica gel column chromatography to give 0.061 g of 31 (69% yield based on recovered starting material 30) and 0.030 g of 30 (26% recovery). $^1$H NMR dδ 7.39~7.31 (m, 5H, Ar), 6.06 (s, 1H, C10H), 5.91 (s, 1H, C4H), 5.17 (s, 2H, $OCH_2Ar$), 5.10 (dd, J=10.8 Hz, 5.6 Hz, 1H, C5a H), 3.61~3.52 (m, 2H, $CH_2OH$), 3.50 (s, 2H, $CH_2C$=O), 2.46 (dd, J=14.0 Hz, 1.2 Hz, 1H), 2.13~1.96 (m, 2H), 1.73~1.11 (m, 5H), 0.91 (d, J=2 Hz, 3H, Me); $^{13}$C NMR δ 167.6 (s, C=O), 162.7 (s, C=O), 162.1 (s, C3), 156.2 (s, C4a), 135.2 (C10a), 133.8 (s, Ar), 128.8 (d, Ar), 128.6 (d, Ar), 128.5 (d, Ar), 109.0 (d, C10), 102.3 (d, C4), 98.9 (s, C9a), 79.9 (s, C5a), 67.6 (t, $OCH_2Ar$), 40.1 (t, $CH_2$), 39.5 (t), 37.3 (t), 32.5 (t), 31.2 (t) 30.5 (t), 28.7 (t), 13.3 (q, Me).

18. (5aS,7S)-7-(1-Hydroxymethyl-1-ethyl)-3-methyl-1H,7H-5a,6,8,9-tetrahydro-1-oxopyrano[4,3-b][1]benzopyran (32)

To a cold solution (−25° C.) of 0.500 g (1.94 mmol) of 24 in 10 mL THF under argon was added 1.94 mL (1.94 mmol) of $BH_3$.THF complex (1.0 M in THF). The reaction mixture was stirred at −25° C. for overnight. To it, 4 mL of 0.5% NaOH aqueous solution and 4 mL of 30% hydrogen peroxide solution were added to the reaction mixture at 0° C., and stirred for 4 hours. The reaction mixture was then diluted with 50 mL of distilled water and extracted three times with methylene chloride (50 mL each). The combined methylene chloride was washed with 40 mL of brine, dried over $MgSO_4$, concentrated, and column chromatographed on silica gel to give 0.326 g of 32 (82% yield, based on 26% recovered starting material 24) and 0.130 g of 24 (26% recovery). $^1$H NMR, δ 6.08 (s, 1H, C10H), 5.71 (s, 1H, C4H), 5.07 (t, J=5.2 Hz, 1H, C5a H), 3.62-3.52 (m, 2H, $CH_2OH$), 2.46 (m, 1H), 2.19 (s, 3H, Me), 2.13~1.99 (m, 2H), 1.73~1.51 (m, 3H), 1.19~1.12 (m, 2H), 0.92 (d, J=1 Hz, 3H, Me).

19. 4-Bromo-6-methyl-2H-pyrone (37)

To a 10 mL DMF solution at 0° C. was added dropwise a solution of 8.734 g (32 mmol) $PBr_3$ in 18 mL of distilled diethyl ether. Then, 1.009 g (8.0 mmol) pyrone solution in 8 mL DMF was transferred to the $PBr_3$ solution via cannula. The resulting mixture was heated to 60° C. for overnight. The reaction mixture was subsequently cooled to 0° C., then quenched with 40 mL of distilled water, extracted with 20 mL×6 of ethyl ether, combined ethyl layer was washed with 50 mL of distilled water, dried over $MgSO_4$, and concentrated to give 1.251 g of 37 (83% yield). $^1$H NMR δ 6.47 (s, C3), 6.20 (s, C5), 2.25 (s, Me); $^{13}$C NMR δ 161.9 (s, C2), 159.5 (s, C6), 140.5 (s, C4), 113.7 (d, C3), 107.6 (s, C5).

20. 4-Azido-6-methyl-2H-pyrone (38)

A mixture of 1.250 g (6.61 mmol) of 1.85 and 0.645 g (9.92 mmol) of sodium azide in 25 mL DMF was stirred for 1 hour under argon atmosphere. The reaction mixture was then poured into 65 mL of ice water, stirred for 10 minutes, extracted with diethyl ether (50 mL×6), the combined ether layer was washed with 50 mL×3 of distilled water, dried over sodium sulfate, and concentrated to give 0.788 g of 38 (80% yield). $^1$H NMR δ 5.76 (d, J=2 Hz, 1H, C3H), 5.64 (dd, J=2 Hz, 0.4 Hz, 1H, C5H), 2.18 (d, J=0.4 Hz, Me); $^{13}$C NMR δ 163.7 (s, C2), 162.3 (s, C6), 156.2 (s, C4), 98.9 (d), 96.7 (d), 19.8 (q, Me).

21. 4-Amino-6-methyl-2H-pyrone (39)

To a 0.310 g (2.05 mmol) of 38 and 0.031 g of 10% Pd/C in 10 mL of ethanol was maintained under 1 atm (a ballonn) of hydrogen gas for 1 hour. The reaction mixture was then filtered through Celite, and ethanol of the filtrate was removed through rotary evaporation to give 0.260 g of 39 (100% yield). $^1$H NMR δ 5.56 (s, 1H, C3H), 5.12 (s, 1H, C5H), 4.45 (s, 2H, $NH_2$), 2.20 (s, Me); $^{13}$C NMR δ 163.6 (s, C2), 161.3 (s), 98.6 (d, C5), 80.4 (d, C3), 19.5 (q, Me).

22. 3-Methyl-1H-6,7,8,9-tetrahydro-1-oxopyrano[4,3-b]quinoline (34) and 3-Methyl-1H-7,8,9,10-tetrahydro-1-oxopyrano[4,3-e]iosquinoline (35)

A mixture of 0.250 g (2.28 mmol) of 1-cyclohexenecarboxaldehyde (21), 0.190 g (1.52 mmol) of 4-amino-6-methyl-2-pyrone (36), and 0.035 g (0.15 mmol) of (S)-(+)-10-camphorsulfonic acid in 12 mL of toluene was heated at 85° C. under argon atmosphere for 3 days. The mixture was cooled to room temperature, filtered, and washed with 20 mL of ethyl acetate. The filtrate was diluted with 100 mL of methylene chloride, washed with 50 mL of water, and 50 mL of brine, dried over $MgSO_4$, concentrated, and column chromatographed on silica gel using ethyl acetate:hexane (2:1) as eluant to give 13.3 mg of 34. (19% yield based on recovered starting material), 33 mg (48% yield based on recovered starting material) of 35 and 150 mg (79% recovery) of pyrone 36.

Compound 34: white solid, mp 71~72° C.; $^1$H NMR (CDCl$_3$) δ 8.15 (s, 1H, C10H), 6.44 (s, 1H, C4H), 3.01 (t, J=7 Hz, 2H, CH$_2$), 2.88 (t, J=7 Hz, 2H, CH$_2$), 2.31 (s, 3H, Me), 1.95 (m, 2H, CH$_2$), 1.86 (m, 2H, CH$_2$); $^{13}$C NMR (CDCl$_3$) δ 168 (s, C1), 165.71 (s), 157.69 (s), 152.22 (s, C3), 137.2 (d, C10), 132.34 (s), 114.0 (s), 105.48 (d), 33.34 (t, CH$_2$), 28.69 (t, CH$_2$), 22.59 (t, CH$_2$), 22.32 (t, CH$_2$), 19.89 (q, Me); MS FAB 216 (M+1).

Compound 35: white solid, mp 73-74° C.; $^1$H NMR (CDCl$_3$) δ 8.50 (s, 1H, C6H), 6.43 (s, 1H, C4H), 3.35 (t, J=6 Hz, 2H, CH$_2$), 2.82 (t, J=6 Hz, 2H, CH$_2$), 2.29 (s, 3H, Me), 1.90-1.80 (m, 4H, CH$_2$); $^{13}$C NMR (CDCl$_3$) δ 162.5 (s, C1), 157.4 (s), 156.4 (s), 154.4 (s), 151.4 (s), 132.7 (s), 114.6 (s), 106.5 (d, C4), 28.6 (t, CH$_2$), 27.6 (t, CH$_2$), 22.6 (t, CH$_2$), 21.7 (t, CH$_2$), 19.9 (q, Me); MS FAB 216 (M+1), 215, 188, 154, 136.

23. (5aS,7S)-7-{[(1-Methylsulfonyloxy)methyl]ethyl}-3-methyl-4H,7H-5a,6,8,9-tetra-hydro-1-oxopyrano[4,3-b][1]benzopyran (40)

To a solution of 0.500 g (0.18 mmol) of 32 in 5 mL methylene chloride under argon was added 0.08 mL (0.54 mmol) of triethylamine and 0.02 mL (0.27 mmol) of methanesulfonyl chloride at 0° C. The resulting mixture was stirred at this temperature for 3 hours, diluted with 30 mL of distilled water, and extracted three times with methylene chloride (30 mL each). The combined methylene chloride was washed with 20 mL of saturated aqueous sodium bicarbonate, 20 mL brine, dried over MgSO$_4$, concentrated, and column chromatographed to give 0.060 g of 40 (94% yield). $^1$H NMR δ 6.08 (s, 1H, C10H), 5.71 (s, 1H, C4H), 5.06 (m, 1H, C5aH), 4.18~4.08 (m, 2H, CH$_2$O), 3.03 (s, 3H, MeS), 2.49 (d, J=2.8 Hz, 1H), 2.19 (s, 3H, Me), 2.14~1.11 (m, 7H), 0.98 (d, J=6.8 Hz, 3H, Me); $^{13}$C NMR (contains stereoisomer at C1') δ 161.8 (s, C=O), 132.4, 109.6, 105.2, 99.8, 79.2, 72.3, 38.9, 37.5, 37.2, 36.9, 32.2, 30.8, 28.6, 20.2, 13.3, 13.2.

24. (5aS,7S)-7-[1-(9-Adenylmethyl)-ethyl]-3-methyl-1H,7H-5a,6,8,9-tetrahydro-1-oxopyrano[4,3-b][1]benzopyran (41)

To a solution of 0.022 g (0.47 mmol) of NaH in 3 mL DMF was added 0.046 g (0.34 mmol) of adenine. The reaction mixture was allowed at room temperature for 2 hours. The above anion was then added to 0.110 g (0.3 mmol) of 40 in 3 mL DMF. The reaction mixture was stirred 70° C. for overnight. After the reaction was cooled to r.t. DMF was removed via vacuum. The residue was subjected to silica gel column chromatography using mixture of methylene chloride and methanol as eluent to obtain 0.100 g of 41 (85% yield).

25. (5aS,7S)-7-{1-[9-(3-Deazaadenyl)methyl]-ethyl}-3-methyl-1H,7H-5a,6,8,9-tetrahydro-1-oxopyrano[4,3-b][1]benzopyran (42)

To a solution of 0.005 g (0.47 mmol) of NaH in 2 mL DMF under argon was added 0.019 g (0.14 mmol) of 3-deazaadenine at room temperature. The reaction was stirred at room temperature for 2 hours. The above anion solution was then added to 0.050 g (0.14 mmol) of 40 in 1 mL DMF. The reaction mixture was then stirred at 70° C. for overnight. The solvent was removed via vacuum and the residue was subjected to silica gel column chromatography using mixture of methylene chloride and methanol as eluent to obtain 0.044 g of 42 (80% yield).

26. (5aS,7S)-7-[(1-Azidomethyl)-ethyl]-3-methyl-1H,7H-5a,6,8,9-tetrahydro-1-oxo-pyrano[4,3-b][1]benzopyran (43)

To a solution of 0.120 g (0.34 mmol) of 40 in 5 mL under argon was added 0.088 g (1.36 mmol) of sodium azide at room temperature. The reaction mixture was then stirred at 70° C. for overnight, cooled to room temperature, diluted with 20 mL of distilled water, and extracted three times with methylene chloride (30 mL each). The combined methylene chloride was washed with 20 mL brine, dried over MgSO$_4$, concentrated, and purified through silica gel column chromatography using mixture of hexane and ether as eluent to give 0.071 g of 43 (70% yield).

$^1$H NMR δ 6.07 (s, 1H, C10H), 5.72 (s, 1H, C4H), 5.06 (m, 1H, C5a H), 3.32~3.20 (m, 2H, CH$_2$N$_3$), 2.49~2.44 (m, 1H), 2.19 (s, 3H, Me), 2.10~1.99 (m, 2H), 1.74~1.51 (m, 3H), 1.26~1.22 (m, 2H), 0.95 (d, J=6.8 Hz, 3H, Me); $^{13}$C NMR δ 163.3 (s, C=O), 163.3 (s), 162.5 (s), 132.3 (s), 109.4 (d), 99.8 (d), 97.4 (s), 79.4 (d, C5a), 55.4 (t, CH$_2$N$_3$), 39.0 (d), 38.0 (d), 37.6 (t), 36.8 (t), 32.2 (t), 30.8 (t), 28.5 (q), 20.2 (q, Me).

27. (5aS,7S)-7-[1-(N-Phthalimidylmethyl)-ethyl]-3-methyl-1H,7H-5a,6,8,9-tetra-hydro-1-oxopyrano[4,3-b][1]benzopyran (44)

To a solution of 0.120 g (0.34 mmol) of 40 in 5 mL under argon was added 0.126 g (0.68 mmol) of potassium phthalimide at room temperature. The reaction mixture was stirred at 70° C. for overnight, cooled down to room temperature, diluted with 20 mL of distilled water, and extracted three times with methylene chloride (30 mL each). The combined methylene chloride was washed with 20 mL brine, dried over MgSO$_4$, concentrated, and purified through silica gel column chromatography using a gradient mixture of hexane and ether as eluent to give 0.136 g of 44 (99% yield). $^1$H NMR δ 7.89~7.72 (m, 4H, Ar), 6.08 (s, 1H, C10H), 5.72 (s, 1H, C4H), 5.04 (m, 1H, C5a H), 3.69~3.53 (m, 2H, CH$_2$—N), 2.48 (t, J=15.6 Hz, 1H), 2.08 (s, 3H, Me), 2.12~1.92 (m, 2H), 1.76~1.54 (m, 3H), 1.34~1.18 (m, 2H), 0.90 (d, J=6.8 Hz, 3H, Me); $^{13}$C NMR δ 168.8 (s, C=O), 163.4 (s, C=O), 163.3 (s, C3), 161.6 (s, C4a), 134.2 (d, Ar), 132.5 (s, C10a), 132.1 (s, Ar), 109.5 (d, C4), 99.9 (d, C10), 97.5 (s, C9a), 79.6 (d, C5a), 42.0 (t, CH$_2$N), 38.4 (d), 36.9 (d), 32.4 (t), 31.1 (t), 30.5 (t), 27.8 (q), 20.2 (q, Me).

28. 3-(Hydroxymethyl)-1H,7H-5a,6,8,9-tetrahydro-1-oxopyrano[4,3-b][1]benzopyran (26)

To a cold (−10° C.) solution of 0.3 mL (2 mmol) of diisopropylamine in 5 mL of diethyl ether under argon was added 2.6 mL (2 mmol; 1.6 M solution in hexanes) of n-butyllithium via syringe and the solution was stirred for 1 hour at this temperature. In another flask, 0.222 g (1 mmol) of 23 in 9 mL THF under argon atmosphere was prepared and cooled to −78° C. The freshly prepared LDA was added to the above solution via cannula. The solution was allowed to react at −78° C. for 3 hours. In a separated flask, 1.3125 g of MoO$_5$.HMPA.pyridine (3 mmol) was added, vacuum dried, dissolved in 10 mL of THF, and cooled to −40° C. The above anion solution was cannulated into the MoOPH solution. After the reaction was stirred for 1.5 h, 2 mL of HCl (4 M in dioxane) and 40 mL of saturated aqueous Na$_2$SO$_3$ were added, and the mixture was extracted four times with ethyl acetate (80 mL each). The combined organic layer was washed with 10 mL of 1 N HCl, dried over MgSO$_4$, concentrated, and column chromatographed on silica gel using a gradient mixture of hexane and ethyl acetate as eluant to give 35.2 mg (20.7% yield) of alcohol 26 and 63.4 mg (29% recovery) of 23. $^1$H NMR δ 6.03 (bs, 2H, C4&10 Hs), 5.02 (m, 1H, C5a H), 4.38 (s, 2H, CH$_2$OH), 2.42~1.2 (a series of m, 8H); $^{13}$C NMR δ 163.4 (s, C=O), 136 (s), 134.1 (s), 128.4 (s), 125.7 (d), 109.1 (d), 98.8 (s), 80 (d), 61.3 (t), 35.3 (t), 33.3 (t), 27.0 (t), 24.6 (t).

29. 3-(Formyl)-1H,7H-5a,6,8,9-tetrahydro-1-oxopyrano[4,3-b][1]benzopyran (27)

To a solution of 33.4 mg (0.142 mmol) of alcohol 26 in 6 mL of methylene chloride under argon was added 0.1093 g (0.26 mmol) of Dess-Martin periodinane. The reaction mixture was stirred at room temperature for 45 h, filtered through Celite, rinsed with 50 mL of methylene chloride, and the filtrate was concentrated to dryness to give 38.5 mg. This residue was column chromatographed on silica gel using a gradient mixture of hexane and ether as eluant to give 16 mg (53.3% yield) of aldehyde 27 and 3.1 mg of recovered 26. $^1$H NMR δ 9.47 (s, 1H, CHO), 6.64 (s, 1H, C4H), 6.14 (s, 1, C10H), 5.16 (m, 1H, C5a H), 2.5~1.2 (a series of m, 8H); $^{13}$C NMR δ 182.52 (s, CHO), 160.1 (s, C1), 138.4 (s), 130.9 (s), 128.8 (s), 125.5 (s), 109.2 (d), 107.7 (d), 35.2 (t), 33.4 (t), 26.8 (t), 24.4 (t).

30. Benzyl (5aS,7S)-{7-isopropenyl-1H,7H-5a,6,8,9-tetrahydro-1-oxopyrano[4,3-b][1]benzopyran-3-yl}acetate (101)

To a cold (−10° C.) solution of 0.68 mL (4.8 mmol) of diisopropylamine in 20 mL of diethyl ether under argon was added 3.00 mL (4.8 mmol; 1.6 M solution in hexanes) of n-butyllithium via syringe, and the solution was stirred for 1 h. In another flask, a solution of 0.50 g (1.9 mmol) of 108 in 20 mL of THF under argon was cooled to −78° C. The LDA solution was added to the pyrone solution at −78° C. via cannula, followed by 0.67 mL (3.9 mmol) of HMPA. After 3 h of stirring, a cold (−78° C.) solution of 0.55 mL (3.9 mmol) of benzyl chloroformate in 20 mL of THF was added via cannula, and stirred for 2 h. The reaction solution was diluted with 40 mL of aqueous NaHCO$_3$, and extracted three times with dichloromethane. The combined organic layer was washed with 40 mL of brine, dried (MgSO$_4$), concentrated, and column chromatographed on silica gel using a gradient mixture of hexane and ether as eluant to give 0.22 g (46% yield; based on reacted 108) of 101 and 0.19 g (38% recovery) of 108. Mp 114-116° C.; [α]$_D$=−28° (c 1.5, CHCl$_3$); $^1$H NMR δ 7.38-7.31 (m, 5H, Ar), 6.08 (s, 1H, C10-H), 5.91 (s, 1H, C4-H), 5.28 (s, 2H, CH$_2$O), 5.12 (dd, J=1.2, 5.2 Hz, 1H, C5a-H), 4.75 (s, 1H, =CH$_2$), 4.72 (s, 1H, =CH$_2$), 3.50 (s, 2H, CH$_2$CO), 2.49-2.45 (m, 1H), 2.21-2.01 (m, 3H), 1.86-1.70 (m, 2H), 1.73 (s, 3H, Me), 1.34-1.25 (m, 1H); $^{13}$C NMR δ 167.5, 162.6, 161.9, 156.2, 147.8, 135.2, 133.2, 128.7, 128.6, 128.4, 109.8, 109.3, 102.2, 98.8, 79.5, 67.5, 43.4, 39.9, 39.4, 32.4, 31.9, 20.8. Anal. calcd for C$_{24}$H$_{24}$O$_5$: C, 73.45; H, 6.16. Found: C, 73.74; H, 6.50.

31. Benzyl (5aS,7S)-{7-[(1R)- and (1S)-2-hydroxy-1-methylethyl]-1H,7H-5a,6,8,9-tetrahydro-1-oxopyrano[4,3-b][1]benzopyran-3-yl}acetate (102)

A solution of 0.115 g (0.29 mmol) of 101 and 0.30 mL (0.30 mmol) of BH$_3$.THF complex (1.0 M in THF) in 5 mL of THF was kept at −25° C. for 14 h. The solution was warmed to 0° C., 2 mL (0.3 mmol) of 0.5% aqueous NaOH solution and 2 mL (17.6 mmol) of 30% hydrogen peroxide were added, and the mixture was stirred at 0° C. for 6 h. The mixture was then neutralized with 6N HCl, diluted with 30 mL of water, and extracted three times with dichloromethane. The combined extract was washed with brine, dried (MgSO$_4$), concentrated, and column chromatographed on silica gel using a gradient mixture of hexane and diethyl ether as eluant to give 0.061 g (69% yield; based on reacted 101) of 102 as a mixture of two diastereomers at C13, 2R and 2S, and 0.030 g (26% recovery) of 101. Mp 108-110° C.; $^1$H NMR δ 7.39~7.31 (m, 5H, Ar), 6.06 (s, 1H), 5.91 (s, 1H), 5.17 (s, 2H, OCH$_2$), 5.10 (dd, J=10.8, 5.6 Hz, 1H, C5a-H), 3.61-3.52 (m, 2H, CH$_2$OH), 3.50 (s, 2H, CH$_2$CO), 2.46 (dd, J=14.0, 1.2 Hz, 1H), 2.13-1.96 (m, 2H), 1.73-1.11 (m, 5H), 0.91 (d, J=2 Hz, 3H, Me); $^{13}$C NMR δ 167.6, 162.7, 162.1, 156.2, 135.2, 133.8, 128.8, 128.6, 128.5, 109.0, 102.3, 98.9, 79.9, 79.8, 67.6, 65.8, 40.1, 40.0, 39.5, 39.4, 37.4, 37.3, 37.1, 32.6, 32.4, 31.2, 30.5, 28.7, 13.3 (Me for a diastereomer), 13.2 (Me for another diastereomer). Anal. calcd for C$_{24}$H$_{26}$O$_6$.0.5H$_2$O: C, 68.65; H, 6.49. Found: C, 69.22; H, 6.54.

32. Benzyl (5aS,7S,9aS,10S)-{10-hydroxy-7-[(1R) and (1S)-2-hydroxy-1-methylethyl]-1H,7H-5a,6,8,9-tetrahydro-1-oxopyrano[4,3-b][1]benzopyran-3-yl}acetate (103)

A solution of 0.10 g (0.26 mmol) of 101 and 0.26 mL (0.26 mmol) of BH$_3$.THF complex (1.0 M in THF) in 3 mL of THF was kept at −20° C. for 3 h and then at 0° C. for 12 h. To it, 2 mL of 0.5% aqueous NaOH solution and 2 mL of 30% hydrogen peroxide were added, and the mixture was stirred at 0° C. for 4 h. The mixture was then neutralized with 6N HCl, diluted with 10 mL of water, and extracted three times with dichloromethane. The combined extract was washed with brine, dried (MgSO$_4$), concentrated, and column chromatographed on silica gel using a gradient mixture of hexane and diethyl ether as eluant to give 15 mg (14% yield) of 102 and 36 mg (32% yield) of 103. $^1$H NMR 7.36 (m, 5H, Ar), 5.99 (s, C4H), 5.18 (s, CH$_2$O), 4.66 (dd, J=8.8, 3.2 Hz, 1H, C10H), 4.46 (m, 1H, C5aH), 4.26 (bs, 1H, OH), 3.58 (m, 2H, CH$_2$O), 3.53 (s, 2H, CH$_2$CO), 2.21 (m, 1H), 2.14 (bs, 1H, OH), 1.78-1.33 (a series of m, 8H), 0.93 (d, J=7 Hz, 3H, Me of a diastereomer), 0.90 (d, J=7 Hz, 3H, Me of another diasteromer). $^{13}$C NMR (2 diastereomers at C13) δ 167.3, 164.6, 163.4, 156.6, 135.0, 128.7 (2C, Ar), 128.4 (2C, Ar), 103.0, 100.9, 94.0, 67.5, 65.9, 59.5, 39.5, 39.1, 37.9, 31.6, 29.6, 24.0, 22.3, 13.7, 13.5. Anal. calcd for C$_{24}$H$_{28}$O$_7$.0.5H$_2$O: C, 65.89; H, 6.68. Found: C, 66.17; H, 7.26.

33. (5aS,7S)-{7-Isopropenyl-1H,7H-5a,6,8,9-tetrahydro-1-oxopyrano[4,3-b][1]-benzopyran-3-yl}acetic acid (109)

To a cold (−10° C.) solution of 0.27 mL (1.90 mmol) of diisopropylamine in 5 mL of diethyl ether under argon was added 1.20 mL (1.90 mmol; 1.6 M solution in hexanes) of n-butyllithium via syringe, and the solution was stirred for 1 h. In another flask, a solution of 0.25 g (0.97 mmol) of 108 in 5 mL of THF under argon was cooled to −78° C. To it, the LDA solution was added via cannula, stirred for 2 h, and carbon dioxide gas was then introduced. The color of the blue anion changed to brownish color. The reaction mixture was stirred for 30 min, 20 mL of aqueous NaHCO$_3$ was added, and extracted with diethyl ether three times. The aqueous layer was acidified with 6N HCl, extracted three times with dichloromethane. The combined dichloromethane layers were washed with water, brine, dried (MgSO$_4$), and concentrated to give 0.271 g (92% yield) of 109. This material was used in the next step without further purification. Compound 109 undergoes decarboxylation when subjected to silica gel column chromatography to give 108. $[\alpha]D=+22°$ (c 1.0, $CHCl_3$); MS, EI m/z 258 (M-$CO_2$), 189, 176; $^1$H NMR δ 6.09 (s, 1H), 5.95 (s, 1H), 5.13 (m, 1H), 4.75 (s, 1H, =$CH_2$), 4.72 (s, 1H, =$CH_2$), 3.51 (s, 2H, $CH_2CO$), 2.51-1.21 (a series of m, 7H), 1.73 (s, 3H, Me); $^{13}$C NMR δ 171.0, 163.2, 162.8, 156.5, 147.8, 133.6, 110.0, 109.2, 102.6, 98.9, 79.8, 43.5, 40.0, 39.3, 32.6, 32.1, 20.9. HRMS calcd for $C_{17}H_{19}O_5$(M+1) 303.1457, found 303.1400.

34. (3S)-3-{[(5a'S,7'S)-7-Isopropenyl-1H,7H-5a,6,8,9-tetrahydro-1-oxopyran[4,3-b][1]benzopyran-3-yl]methylcarbamoyl}-4-oxo-4-(4-nitrophenylamino)-butanoic acid (104)

A mixture of 35 mg (0.12 mmol) of 109, 44 mg (0.12 mmol) of 110, and 36 mg (0.18 mmol) of DCC in 5 mL of dichloromethane under argon was stirred at 25° C. for 20 h. The reaction mixture was filtered, and the filtrate was concentrated, and column chromatographed on silica gel using a gradient mixture of hexane, dichloromethane and methanol as eluant to give 72 mg (90% yield) of the benzyl ester protected amide. A solution of 40 mg (0.06 mmol) of the above amide and 1 mL of 1% aqueous NaOH in 2 mL of THF was stirred at 25° C. for 1 h. The solution was neutralized with 4N HCl, concentrated, and the resulting solid was washed with dichloromethane (to remove benzyl alcohol) and dried under vacuum to give 34 mg (100% yield) of 104. Mp 234-236° C.; $[\alpha]^{23}_D$=+23.1° (c 1.2, $CHCl_3$); MS (electrospray); m/z 537 (M$^+$), 535 (M-22), 518 (100%, M-1-$H_2O$). $^1$H NMR (DMSO-$d_6$) δ 8.19 (d, J=9.6 Hz, 1H, Ar), 7.85 (d, J=9.6 Hz, 1H, Ar), 6.11 (s, 1H, C4H), 5.94 (s, 1H, C 10H), 4.75 (s, 1H, =$CH_2$), 4.72 (s, 1H, =$CH_2$), 4.05 (m, 1H, CHN), 3.24 (s, 2H, $CH_2CO$), 2.10 (m, 2H, $CH_2CO$), 1.90-1.02 (a series of m, 7H), 1.70 (s, 3H, Me); $^{13}$C NMR (DMSO-$d_6$) δ 173.9, 170.8, 169.8, 165.4, 162.0, 157.0, 148.1, 145.6, 141.9, 133.1, 128.2, 124.9, 118.8, 109.9, 100.6, 90.3, 67.9, 55.8, 49.9, 34.7, 31.5, 29.0, 25.4, 20.6, 17.2. HRMS calcd for $C_{27}H_{27}N_3O_9$ 537.1748, found 537.1742.

35. Benzyl (S)-3-amino-4-oxo-4-(4-nitrophenylamino)-butanoate (110)

To a solution of 0.214 g (1.55 mmol) of p-nitroaniline and 0.50 g (1.55 mmol) of N-(t-butyloxycarbonyl)-L-aspartic acid 4-benzyl ester (111) in 10 mL of dichloromethane at 25° C. under argon, was added a solution of 0.383 g (1.86 mmol) of DCC in 20 mL of dichloromethane via cannula. The reaction mixture was stirred for 24 h, filtered, concentrated, and column chromatographed on silica gel using a mixture of hexane, methanol, and dichloromethane (40:4:1) as eluant to give 0.45 g of the amide (85% yield; based on reacted p-nitroaniline) and 0.05 g (23% recovery) of p-nitroaniline. Mp 47-50° C.; $[\alpha]^{20}_D$=-36.5° (c 1.3, $CHCl_3$); $^1$H NMR δ 9.18 (s, 1H, NH), 8.20 (d, J=7 Hz, 2H, Ar), 7.66 (d, J=7 Hz, 2H, Ar), 7.36 (s, 5H, Ar), 5.86 (s, 1H, NH), 5.20 (d, J=12.4 Hz, 1H, $OCH_2$), 5.16 (d, J=12.4 Hz, 1H, $OCH_2$), 4.67 (m, 1H, CHN), 3.09 (dd, J=17, 4 Hz, 1H, $CH_2CO$), 2.82 (dd, J=17, 6 Hz, 1H, $CH_2CO$), 1.49 (s, 9H, t-Bu); $^{13}$C NMR δ 171.6, 169.4, 153.1, 143.4, 135.2, 128.6, 128.5, 128.47, 128.2, 125.0, 119.2, 67.1, 65.8, 51.6, 35.4, 28.2. A solution of 0.15 g (0.34 mmol) of the above amide and 0.85 mL (3.39 mmol) of 4 M HCl in dioxane was stirred at 25° C. for 2 h, neutralized with 10 mL of aqueous $NaHCO_3$, and extracted three times with dichloromethane. The combined organic layer was washed with brine, dried ($MgSO_4$), and concentrated to give 0.122 g of 110 (100% yield): $[\alpha]^{22}_D$=-19° (c, 0.15, $CHCl_3$; $^1$H NMR δ 10.00 (s, 1H, CONH), 8.22 (d, J=7 Hz, 2H, Ar), 7.75 (d, J=7 Hz, 2H, Ar), 7.34 (s, 5H, Ar), 5.18 (d, J=12.4 Hz 1H, $OCH_2$), 5.14 (d, J=12.4 Hz, 1H, $OCH_2$), 3.83 (dd, J=6.8, 4.4 Hz, 1H, CHN), 3.02 (dd, J=17, 4.4 Hz, 1H, $CH_2$), 2.96 (dd, J=17, 6.8 Hz, 1H, CH2); $^{13}$C NMR δ, 174.4, 172.0, 143.4, 135.1, 128.7, 128.5, 128.4, 128.3, 125.1, 118.9, 66.9, 52.4, 38.9. HRMS calcd for $C_{17}H_{18}N_3O_5$ (M+1) 344.1169, found 344.1150.

36. (5aS,7 S)-7-[(1R) and (1S)-2-Hydroxy-1-methylethyl]-3-methyl-1H,7H-5a,6,8,9-tetrahydro-1-oxopyrano[4,3-b][1]benzopyran (112)

To a cold solution (-225° C.) of 0.50 g (1.94 mmol) of 108 in 10 mL of THF under argon, was added 1.94 mL (1.94 mmol) of $BH_3$.THF complex (1.0 M in THF). After stirring the solution at -25° C. for 10 h, 14 mL (2.1 mmol) of 0.5% aqueous NaOH and 4 mL of 30% hydrogen peroxide were added at 0° C. The solution was stirred for 4 h, diluted with 50 mL of water, and extracted three times with dichloromethane. The combined organic layer was washed with 40 mL of brine, dried ($MgSO_4$), concentrated, and column chromatographed on silica gel using a gradient mixture of hexane and diethyl ether as eluants to give 0.326 g (82% yield; based on reacted 108) of 112 as a mixture of two diastereomers at C12 (1:1; based on $^{13}$C NMR spectrum) and 0.130 g (26% recovery) of 108. $^1$H NMR δ 6.08 (s, 1H, C4H), 5.71 (s, 1H, C10H), 5.07 (t, J=5.2 Hz, 1H, C5aH), 3.62-3.52 (m, 2H, $CH_2O$), 2.46 (m, 1H), 2.19 (s, 3H, Me), 2.13-1.99 (m, 2H), 1.73-1.51 (m, 3H), 1.19-1.12 (m, 2H), 0.92 (d, J=7 Hz, 3H, Me); $^{13}$C NMR (two diastereomers) δ163.5, 162.8, 161.6, 133.0, 109.0, 100.0, 97.4, 79.7, 79.6, 65.6, 39.9, 39.8, 39.4, 37.2, 37.1, 36.9, 32.4, 32.3, 31.1, 30.4, 28.5, 20.1, 13.2 (Me for a diastereomer), 13.1 (Me for another diastereomer). Anal. calcd for $C_{16}H_{20}O_4$: C, 69.55; H, 7.29. Found: C, 69.26; H, 7.03.

37. (5aS,7S)-3-Methyl-7-[(1R) and (1S)-2-(methanesulfonyloxy)-1-methylethyl]-1H,7H-5a,6,8,9-tetrahydro-1-oxopyrano[4,3-b][1]benzopyran (113)

To a cold (0° C.) solution of 50 mg (0.18 mmol) of 112 in 5 mL of dichloromethane under argon, were added 0.08 mL (0.54 mmol) of triethylamine and 0.02 mL (0.27 mmol) of methanesulfonyl chloride. The solution was stirred for 3 h, diluted with 30 mL of water, and extracted three times with dichloromethane. The combined dichloromethane layer was washed with saturated aqueous $NaHCO_3$, and brine, dried ($MgSO_4$), concentrated, and column chromatographed on silica gel using a gradient mixture of hexane and ether as eluants to give 60 mg (94% yield) of 113 as a mixture of two diastereomers (1:1; based on $^{13}$C NMR spectrum). NMR δ 6.08 (s, 1H, C4H), 5.71 (s, 1H, C 10H), 5.06 (m, 1H, CHO), 4.18-4.08 (m, 2H, $CH_2O$), 3.03 (s, 3H, MeS), 2.49 (d, J=2.8 Hz, 1H), 2.19 (s, 3H, Me), 2.14-1.11 (m, 7H), 0.98 (d, J=6.8 Hz, 3H, Me); $^{13}$C NMR δ 163.2, 162.4, 161.7, 132.1, 109.6, 105.2, 99.8, 79.2, 79.1, 72.3, 38.9, 37.5, 37.4, 37.3, 37.2, 36.9, 32.2, 32.1, 30.8, 28.6, 20.2, 13.3 (Me for a diastereomer), 13.2 (Me for another diastereomer). Anal. calcd for $C_{17}H_{22}O_6S$: C, 57.61; H, 6.26. Found: C, 57.65; H, 6.43.

38. (5aS,7S)-7-[(1R) and (1S)-2-(N-9-Adenyl)-1-methylethyl]-3-methyl-1H,7H-5a,6,8,9-tetrahydro-1-oxopyrano[4,3-b][1]benzopyran (105) and (5aS,7S)-7-[(1R) and (1S)-2-(N-3-adenyl)-1-methylethyl]-3-methyl-1H,7H-5a,6,8,9-tetrahydro-1-oxopyrano[4,3-b][1]benzopyran (106).

To a solution of 0.008 g (0.34 mmol) of NaH in 3 mL of DMF under argon was added 0.046 g (0.34 mmol) of adenine at 25° C., and the solution was stirred for 1 h. This solution was then added to a solution of 0.110 g (0.30 mmol) of 113 in 3 mL of DMF via cannula. The reaction solution was stirred at 80° C. for 20 h. The solvent, DMF, was removed under vacuum at 50° C., 10 mL of dichloromethane was added to the residue, and the dichloromethane was removed via a pipette (to remove trace of DMF and tricyclic pyrone by-product 112). To the resulting solids, 20 mL of ethanol was added, filtered, and the filtrate was concentrated, and column chromatographed on silica gel using a gradient mixture of dichloromethane and methanol as eluant to give 0.026 g (21% yield) of 105 (less polar) and 0.006 g (5% yield) of 106 (more polar). Compound 105 (less polar; two diastereomers at C12): mp 228-230° C.; MS, electrospray, m/z 394 (M+1; 100%), 259 (M-adenine), 136 (adenine); $^1$H NMR δ 8.36 (s, 1H, C2'H), 7.78 (s, 1H, C8'H), 6.09 (s, 1H, C4H), 5.89 (bs, 2H, NH$_2$; disappeared when 1 drop of D$_2$O was added), 5.72 (s, 1H, C10H), 5.01 (m, 1H, C5aH), 4.24 (dd, J=14, 7 Hz, 1H, CHN), 4.01 (dd, J=14, 7 Hz, 1H, CHN), 2.5-1.2 (a series of m, 8H), 2.19 (s, 3H, Me), 0.90 (d, J=7 Hz, 3H, Me); $^{13}$C NMR δ 163.4, 162.7, 161.9, 155.6 (adenine moiety), 153.5 (adenine moiety), 150.6 (adenine moiety), 140.9 (adenine moiety), 132.1, 119.8 (adenine moiety), 109.9, 99.9, 97.5, 79.4, 79.2, 47.9, 39.3, 38.4, 38.3, 38.1, 38.0, 36.2, 32.3, 32.1, 31.1, 27.8, 20.3, 13.8. Anal. calcd for C$_{21}$H$_{23}$N$_5$O$_3$: C, 64.11; H, 5.89. Found: C, 63.80; H, 5.93.

Compound 106 (more polar; 2 diastereomers at C12): MS, electrospray, m/z 394 (M+1, 100%), 259 (M-adenine), 136 (adenine); $^1$H NMR δ 8.07 (s, C8'H of adenine), 7.98 and 7.97 (2 s, 1H, C2'H of adenine; 2 diastereomers), 6.10 (s, 1H, C10H), 5.72 and 5.71 (2s, 1H, C4H), 5.02 (m, 1H, C5aH), 4.50 (dd, J=14, 7 Hz, 1H, CHN), 4.08 (2dd, J=14, 8 Hz, 1H, CHN; 2 diastereomers), 2.46 (m, 2H), 2.20 and 2.19 (2s, 3H, Me; 2 diastereomers), 2.10-1.22 (a series of m, 6H), 0.91 (d, J=7.0 Hz, 3H, Me). $^{13}$C NMR (2 diastereomers) δ 163.2 and 163.1, 162.4, 161.7, 154.4, 154.0, 150.7, 142.3, 131.7 and 131.6; 121.0, 199.8, 99.7, 97.3, 79.0, 78.8, 54.5 and 54.4, 38.9, 38.1 and 38.0, 37.1 and 36.9, 36.1, 32.0 and 31.9, 30.7, 27.6, 20.1, 13.3 and 13.2. HRMS calcd for C$_{21}$H$_{24}$N$_5$O$_3$ (M+H) 394.1881, found 394.1875. Anal. calcd for C$_{21}$H$_{23}$N$_5$O$_3$.2H$_2$O: C, 58.73; H, 6.34. Found: C, 59.20; H, 6.18.

39. Synthesis of Compound 106 from Adenine in DMA

A solution of 0.21 g (0.59 mmol) of mesylate 113 and 80 mg (0.59 mmol) of adenine in 3 mL of DMA (freshly distilled from CaCl$_2$ under reduced pressure) was heated at 150° C. for 3 h. DMA was removed under reduced pressure (70° C./0.5 mm Hg), and the residue of the distillation was triturated with 5 mL of dichloromethane. To the residue, 50 mg (0.59 mmol) of NaHCO$_3$ and 3 mL of ethanol were added, and the mixture was subjected to a silica gel column chromatography using a gradient mixture of dichloromethane and ethanol as eluant to give 0.10 g (43% yield) of 106 and 0.01 g (4% yield) of 105.

40. (5aS,7S)-7-[(1R) and (1S)-2-Azido-1-methylethyl]-3-methyl-1H,7H-5a,6,8,9-tetrahydro-1-oxopyrano[4,3-b][1]benzopyran (118)

A solution of 0.70 g (2.0 mmol) of mesylate 113 and 0.26 g (4.0 mmol) of sodium azide in 20 mL of DMF under argon was stirred at 60° C. for 16 h. The solution was cooled, diluted with ether, washed twice with water, and brine, dried (MgSO$_4$), concentrated, and column chromatographed on silica gel using a gradient mixture of hexane and ethyl acetate to give 0.50 g (83% yield) of 118 and 60 mg (9% recovery) of 113. Compound 118 (2 diastereomers at C12): mp 87-88° C.; MS, m/z 301 (M$^+$); $^1$H NMR δ 6.09 (s, 1H, C4H), 5.71 (s, 11-1, C10H), 5.10 (m, 1H, C5aH), 3.30 (dd, J=13, 6 Hz, 1H, CHN), 3.23 (dd, J=13, 7 Hz, 1H, CHN), 2.48 (d, J=14 Hz, 1H), 2.19 (s, 3H, Me), 2.10-1.95 (m, 2H), 1.7-1.5 (m, 4H), 1.27-1.08 (m, 1H), 0.95 (d, J=7 Hz, 3H, Me); $^{13}$C NMR δ 163.4, 162.7, 161.8, 132.4, 109.6, 99.9, 97.5, 79.5 and 79.4 (C5a, 2 isomers), δ5.5, 39.2, 38.2 and 38.15 (2 isomers), δ7.8 and 37.78 (2 isomers), δ7.0, 32.3 and 32.2 (2 isomers), δ0.9, 28.6, 20.3, 14.5. Anal. calcd for C$_{16}$H$_{19}$N$_3$O$_3$: C, 63.77; H, 6.35. Found: C, 63.99; H, 6.51.

41. (5aS,7S)-7-[(1R) and (1S)-2-Amino-1-methylethyl)-3-methyl-1H,7H-5a,6,8,9-tetrahydro-1-oxopyrano[4,3-b][1]benzopyran (114)

A solution of 0.42 g (1.4 mmol) of azide 118 and 1.0 g of 10% Pd/CaCO$_3$ in toluene was stirred under 1 atm. of hydrogen at 25° C. for 14 h. The mixture was filtered through a short silica gel column using ethyl acetate, CHCl$_3$/CH$_3$OH (2:1), and then CHCl$_3$/CH$_3$OH/NH$_4$OH (2:1:0.01) as eluants to give 0.30 g (78% yield) of amine 114 (2 diastereomers at C12). $^1$H NMR δ 6.07 (s, 1H, C4H), 5.71 (s, 1H, C10H), 5.07 (m, 1H, C5aH), 2.73 (m, 1H, 2 isomer, CHN), 2.58 (m, 1H, 2 isomers, CHN), 2.46 (d, J=13 Hz, 1H), 2.19 (s, 3H, Me), 2.15-1.10 (m, 7H), 0.91 (d, J=7 Hz, 3H, Me); $^{13}$C NMR δ 163.4, 162.7, 161.7, 132.9, 109.3, 100.0, 97.5, 79.8 and 79.7 (2 isomers), 66.0, 46.0 and 45.9 (2 isomers), δ0.9, 39.1, 38.5 and 38.4 (2 isomers), 37.1, 32.6 and 32.4 (2 isomers), δ1.3, 31.2, 28.6, 20.3, 15.5, 14.3. HRMS calcd for C$_{17}$H$_{22}$NO$_3$ (M+1) 276.1601, found 276.1610.

42. 6-Chloro-9-[(2-trimethylsilylethoxy)methyl]-1H-purine (115)

A solution of 0.31 g (2.0 mmol) of 6-chloro-1H-purine and 0.83 g (6.0 mmol) of potassium carbonate in 15 mL of DMF was stirred at 25° C. for 20 min. under argon. To it, 0.53 mL (3.0 mmol) of 1-(chloromethoxy)-2-(trimethylsilyl)ethane (SEM-Cl) was added via syringe, the solution was stirred for 9 h, filtered through Celite, and the filtrate was diluted with diethyl ether, washed with water, and brine, dried (MgSO$_4$), concentrated, and column chromatographed on silica gel using a gradient mixture of hexane and ethyl acetate to give 0.35 g (61% yield) of 115 and 0.08 g (14% yield) of 6-chloro-3-[(2-trimethylsilylethoxy) methyl]-1H-purine (117). Compound 115: mp 33-34° C.; NMR δ 8.70 (s, 1H), 8.24 (s, 1H), 5.62 (s, 2H, NCH2O), 3.60 (t, J=8 Hz, 2H, CH$_2$O), 0.94 (t, J=8 Hz, 2H, CH$_2$Si), −0.12 (s, 9H, MeSi); $^{13}$C NMR δ 152.4, 152.2, 151.3, 145.4, 131.5, 72.7 (CN), 67.8 (CO), 17.8, 21.4 (CSi).

43. 6-Chloro-7-[(2-trimethylsilylethoxy)methyl]-1H-purine (117).

Mp 80-81° C.; $^1$H NMR δ 8.93 (s, 1H), 8.36 (s, 1H), 5.80 (s, 2H, NCH$_2$O), 3.61 (t, J=8 Hz, 2H, CH$_2$O), 0.94 (t, J=8 Hz, 2H, CH$_2$Si), 20.02 (s, 9H, MeSi); $^{13}$C NMR δ162.5, 153.0, 149.3, 143.7, 122.5, 75.9 (CN), 67.2 (CO), 17.9, 21.3 (CSi). Anal. calcd for C$_{11}$H$_{17}$ClN$_4$OSi: C, 46.39; H, 6.02. Found: C, 46.52; H, 6.08.

44. (5aS,7S)-3-Methyl-7-{(1R) and (1S)-2-[(N-9-trimethylsilylethoxymethyl)-N10-adenyl]-1-methylethyl}-1H,7H-5a,6,8,9-tetrahydro-1-oxopyrano[4,3-b][1]benzopyran (119)

A mixture of 56 mg (0.20 mmol) of amine 114, 114 mg (0.40 mmol) of purine 115, 18 mg (0.02 mmol) of Pd$_2$(dba)$_3$, 21 mg (0.08 mmol) of Ph$_3$P, and 41 mg (0.30 mmol) of K$_2$CO$_3$ in 5 mL of toluene was heated in a sealed tube at 140° C. After stirring for 5 h, the mixture was cooled to 25° C., diluted with water, and extracted three times with diethyl ether. The combined ether layer was washed with water, and brine, dried (MgSO$_4$), concentrated, and column chromatographed on silica gel using a gradient mixture of dichloromethane and ethyl acetate as eluant to give 17 mg (16% yield) of 119 (2 diastereomers at C12). $^1$H NMR δ 8.40 (s, 1H), 7.89 (s, 1H), 6.07 (s, 1H, C4H), 5.81 (bs, 1H, NH), 5.70 (s, 1H, C10H), 5.56 (s, 2H, NCH$_2$O), 5.03 (m, 1H, C5aH), 3.64 (m, 1H, CHN), 3.60 (t, J=8 Hz, 2H, CH$_2$O), 3.50 (m, 1H, CHN), 2.46 (d, J=12 Hz, 1H), 2.18 (s, 3H, Me), 2.10-1.2 (a serious of m, 7H), 0.93 (d, J=7 Hz, 3H, Me; 2 diastereomers as indicated by 2 sets of doublet), 0.92 (t, J=8 Hz, 2H, CH$_2$Si, 2 diastereomers as indicated by 2 sets of triplet), 20.05 (s, 9H, MeSi); $^{13}$C NMR δ 163.5, 162.7, 161.8, 155.3, 153.8, 140.1, 132.6, 109.5, 100.0, 97.6, 79.7 and 79.5 (C5a; 2 diastereomers), 72.2, 67.4, 39.5, 38.4 and 38.3 (2 diastereomers), 38.1, 36.7, 32.5 and 32.3 (2 diastereomers), 31.3, 28.3, 20.3, 17.9, 14.3 and 14.2 (2 diastereomers), 21.2. HRMS calcd for C$_{27}$H$_{38}$N$_5$O$_4$Si$^+$ (M+H$^+$) 524.2695, found 524.2292.

45. (5aS,7S)-7-[(1R) and (1S)-2-(N10-Adenyl)-1-methylethyl]-3-methyl-1H,7H-5a,6,8,9-tetrahydro-1-oxopyrano[4,3-b][1]benzopyran (107)

A solution of 4 mg (0.008 mmol) of SEM-adenine 119 in 1 mL each of 1 N HCl and methanol was heated at 50° C. for 6 h and cooled to 25° C. The solution was neutralized with saturated aqueous NaHCO$_3$, extracted with ethyl acetate, and the organic layer was washed with brine, dried (MgSO$_4$), concentrated, and column chromatographed on silica gel column using a mixture of CHCl$_3$/MeOH (10:1) as eluant to give 3.0 mg (97% yield) of 107. $^1$H NMR δ 8.44 (s, 1H), 8.00 (s, 1H), 6.3 (bs, 1H, NH), 6.08 (s, 1H, C4H), 5.72 (s, 1H, C10H), 5.05 (m, 1H, C5aH), 3.75 (m, 1H, CHN), 3.57 (m, 1H, CHN), 2.47 (d, J=14 Hz, 1H), 2.19 (s, 3H, Me), 2.10-1.2 (a series of m, 7H), 1.01 (d, J=7 Hz, 3H, Me); $^{13}$C NMR δ 163.5, 162.8, 161.8, 152.8, 138.3 (2 C), 133.7, 132.6, 131.6, 109.5, 100.0, 97.6, 79.7 and 79.5 (2 isomers at C12), 39.5, 38.5, 38.3, 38.1, 36.7, 32.3, 31.3, 29.9, 28.4, 20.3, 14.3 and 14.2 (2 isomers). Anal. calcd for C$_{21}$H$_{23}$N$_5$O$_3$: C, 64.11; H, 5.89. Found: C, 64.35; H, 6.10.

Although the description above contains many specificities, these should not be construed to limit the scope of the invention, but as merely providing illustrations of some of the presently-preferred embodiments of this invention. For example, particular selection of effective dosages is well known in the art without undue experimentation. Also, the particular selection of compounds that have the desired effect is well known to one with ordinary skill in the art. Thus, the scope of the invention should be determined by the appended claims and their legal equivalents, rather than by the examples given. All references cited herein are hereby incorporated by reference to the extent not inconsistent with the disclosure herein.

I claim:

1. A compound of formula:

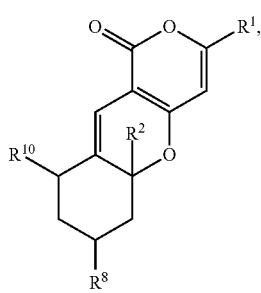

IA wherein R1 is —CH$_3$; and R8 is

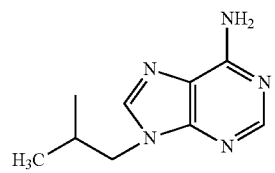

or

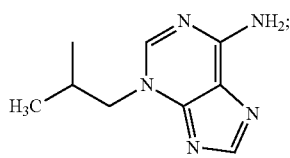

R10 is H; R2 is H.

2. A compound of formula:

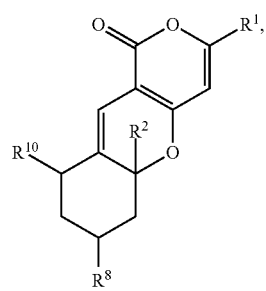

IA wherein R1 is —CH$_3$; and R8 is

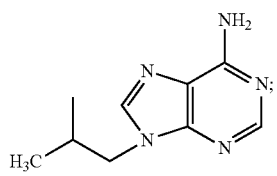

R10 is H; R2 is H.

3. The compound of claim 1, wherein R1 is —CH$_3$; R8 is

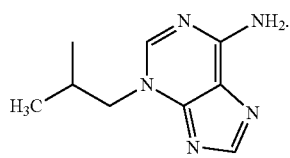

* * * * *